United States Patent
Olefsky et al.

(10) Patent No.: US 7,749,720 B2
(45) Date of Patent: Jul. 6, 2010

(54) METHODS OF IDENTIFYING COMPOUNDS FOR PRODUCING INSULIN SENSITIZATION

(75) Inventors: Jerrold M. Olefsky, Solana Beach, CA (US); Isao Usui, Toyama (JP); Takeshi Imamura, San Diego, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 11/570,864

(22) PCT Filed: Jun. 17, 2005

(86) PCT No.: PCT/US2005/021560

§ 371 (c)(1),
(2), (4) Date: May 22, 2007

(87) PCT Pub. No.: WO2006/009890

PCT Pub. Date: Jan. 26, 2006

(65) Prior Publication Data

US 2007/0292409 A1 Dec. 20, 2007

Related U.S. Application Data

(60) Provisional application No. 60/580,975, filed on Jun. 17, 2004.

(51) Int. Cl.
*G01N 33/53* (2006.01)
*G01N 33/00* (2006.01)
(52) U.S. Cl. .......................... 435/7.8; 435/7.1; 435/7.6; 435/7.72; 435/7.92
(58) Field of Classification Search ........................ None
See application file for complete search history.

(56) References Cited

U.S. PATENT DOCUMENTS

2002/0028772 A1* 3/2002 Ben-Sasson ................. 514/12
2002/0094544 A1* 7/2002 Fang et al. ................... 435/7.9

OTHER PUBLICATIONS

Ruiz-Gomez et al. 1997. J. Biol Chem 272:9601-9604.*
UniProtKB/Swiss_Prot. www.uniprot.org/uniprot/P21146, downloaded Oct. 17, 2008.*
Sterne-Marr et al. 2003. J. Biol. Chem. 278:6050-6058.*
Tseng et al., "Role of GPCR kinases in Glucose-dependent insulinotropic polypeptide receptor signaling," Endocrinology, 2000, vol. 141, No. 3, pp. 947-952, p. 948, 2nd column, 2nd paragraph.
Usui et al., "GRK2 is an endogenous protein inhibitor of the insulin signaling pathway for glucose transport stimulation," EMBO Journal, 2004, 23:2821-2829, entire document, especially p. 2822.
Anis, Y, et al., "Antidiabetic effect of novel modulating peptides of G-protein-coupled kinase in experimental models of diabetes," Diabetologia (2004), 41(7), 1232-1244.

* cited by examiner

*Primary Examiner*—Gary B Nickol
*Assistant Examiner*—Shulamith H Shafer
(74) *Attorney, Agent, or Firm*—Spencer Fane Britt & Browne LLP

(57) ABSTRACT

The invention herein provides a mode of treating metabolic syndrome, which includes Type 2 diabetes mellitus and insulin resistance in human and other subjects by identifying and administering an insulin sensitizing compound which modulates GRK2 function in the insulin signaling pathway. The invention also provides polynucleotides, polypeptides, vectors, cells, tissues and organisms useful in the identification and treatment of metabolic syndrome. A number of desirable insulin sensitizing aspects are achieved by various embodiments of the present invention.

8 Claims, 16 Drawing Sheets

SEQUENCE LISTING

```
<160> NUMBER OF SEQ ID NOS: 9

<210> SEQ ID NO 1
<211> LENGTH: 3332
<212> TYPE: DNA
<213> ORGANISM: Mus Musculus

<400> SEQUENCE: 1
caaggccacg ccggccgcgc gcgccagcaa gaagatcctg ctgccagagc ccaggggacc      60
tcccatccta cagcagatgg accatgctgc cacctctcta caagacaact gatgtcatcg     120
cacctgcatc cgcagcgtca tgcagaagta tctggaggac cgaggagaag tgacctttga     180
aaagatcttt tcgcagaagt tagggtacct gcttttccgg gacttctgcc tgaaccatct     240
ggaagaggcc aagcccttgg tggagttcta cgaagagatc aagaaatatg agaagctgga     300
gacagaggag gaacgtgtgg tccgcagccg agagatcttt gactcctata ttatgaaaga     360
actgctggcc tgctcacatc ccttttcaaa gaatgctacg gagcatgtcc agggccacct     420
ggtgaagaag caggtgcctc cagatctctt ccagccatac attgaggaga tttgtcagaa     480
cctccgaggg gacgtgttcc agaagttcat agagagtgaa aagttcacac ggttctgcca     540
gtggaagaat gttgagctca acatccacct gaccatgaat gacttcagtg tgcatcgaat     600
catcgggcgt gggggcttcg gtgaggtcta tgggtgccgg aaagcagaca caggcaagat     660
gtacgccatg aagtgtctgg acaagaaacg catcaagatg aagcagggag agaccctggc     720
tctgaacgag cggatcatgc tttccctcgt cagcaccggg gactgcccct tcatcgtgtg     780
catgtcatat gcattccaca caccagacaa gctcagcttc atcctggacc tcatgaacgg     840 tgggacctg cactaccacc tgtctcagca tggagtcttc tctgaagccg acatgcgctt     900
ctacgccgct gagatcatcc tgggccttga acacatgcac aatcgctttg tagtctacag     960
ggacctgaag ccagccaaca ttctcctgga tgaacatggc catgtgagaa tctcggacct    1020
gggcctagcc tgtgacttct ccaagaagag gcctcatgcc agtgtgggca cacacggta    1080 catggcccc gaagtcctac agaagggcgt ggcctatgac agcagtgcag actggttctc    1140
cctgggctgc atgctcttca agttgttgcg gggacacagc cccttccggc agcacaagac    1200
caaagacaag catgagattg accgcatgac gttgacgatg gctgtagagc tgcctgactc    1260
cttctcccct gaactccgat ccctgctgga aggtttgttg cagagggacg tcaatcggag    1320
```

```
actaggctgt ctgggccgtg gggctcagga ggtaaaagaa agtcctttct ttcgttccct    1380
ggactggcag atggtcttct tacagaagta ccctcctcca ctgatccccc cacgtgggga    1440
ggtgaatgca gctgacgctt tcgacattgg ctcctttgat gaggaggaca caaaaggaat    1500
caagttactg gacagtgacc aggaactgta ccgcaacttc cctctcacca tctctgagcg    1560
gtggcaacag gaggtggcag agactgtctt tgataccatc aatgctgaaa cagaccggct    1620
ggaggcacga aagaaggcca aaaacaaaca gctgggccac gaggaggact atgccctggg    1680
taaggactgc atcgtgcatg gctacatgtc caagatgggc aaccccttcc tgacccagtg    1740
gcagcggcga tacttctact tgttccccaa ccggctcgag tggaggggtg aaggcgaggc    1800
tccgcagagc ctcctgacca tggaggagat ccagtcagtg aagagacac agatcaagga    1860 acgcaagtgt ctcctgctta agatccgagg tggcaagcag tttgtcctgc agtgtgatag    1920
tgatccagag ctggtgcaat ggaaaaagga gctgcgtgat gcctaccgcg aggcccagca    1980
gctggtacag cgagtaccca agatgaagaa caagccacgc tcgcctgtgg tggagctgag    2040
caaggtgccg ctgatccagc gtggcagtgc caacggcctc tgatccaccc atgtgctgcc    2100
cgcctgccca cccgcctttt ataaacctct aatttatttt gttgaatttt tattatttgt    2160
tttcccgcaa agcggaaaat gtttttatttt gtaattattg tgatctcctg tggccccagc    2220
ctggcccagc cccagggag gggcccgctt gcctcagctc ctgctgccac caacccagcc    2280
actgtctagc accctccccc tgtccccact cccaccccct agggtccttg ctcccagtat    2340
cttcctacag ggaagaagag caaccctcag cagccctctt gcccctccat ggggtgaagc    2400
cacactcagt gggtgtgtca cttcaggctc tgtgggctgt gctcagtctg tggcccagca    2460 ccctgccct agaaagggc aacacagggt actacttgaa ctttcctatc acagctccca    2520
tgccacagag ggacagaccc ctgctgtcct gccctcttgc cactggtgag agaaggccct    2580
tgtctcctca gactaggagg tctcccacag tgacagctcc tgggtccttg ttcaggaaaa    2640
gcctgtgtgt taccactgcc tcatcaggag gctgccattg gcagtggctg ctgctggcct    2700
ccctgcaagt cccctcttct tcctgttgcg tgcctggact caggagcata gaaaagacaa    2760
ttgtggattg gccacactg gcctagcctg aacctagatc cctaaccctg gctgggtga    2820 ggctcacctg cccaggacca cagtgggaca gcctgggcag gtgggtggca cagcataaga    2880
acccagctgg ggccagccct ccctgtcctg gctggtcagt gtgccccac ccacactgtc    2940 cagccccta gccatgtca tgtcagtggc cactgcccac aggtgccacc ttgcccaccg    3000 catgaccccct tgtgccagtc gcgcagctgt gtgtggtgtc gcgccctctc ccttgggg    3060 ctgggtgggc acccctccc ctcttgtcta ctcactccta gggcgtttct ttgccgattt    3120
ttgaatgtga tttttaaagag tggaaaatga gactatgcgt ttttataaaa aatggtgcct    3180
gaaaaaaaaa aaaaaaaaaa aaaaaaaaaa aaaaaaaaaa aaaaaaaaaa aaaaaaaaaa    3240
aaaaaaaaaa aaaaaaaaaa aaaaaaaaaa aaaaaaaaaa aaaaaaaaaa aaaaaaaaaa    3300
aaaaaaaaaa aaaaaaaaaa aaaaaaaaaa aa                                 3332

<210> SEQ ID NO 2
<211> LENGTH: 2067
<212> TYPE: DNA
<213> ORGANISM: Homo sapiens

<400> SEQUENCE: 2
atggcggacc tggaggccgt gctggccgat gtcagttacc tgatggccat ggagaagagc      60
```

-continued

| | |
|---|---|
| aaggcgaccc cggccgcccg cgccagcaag aggatcgtcc tgccggagcc cagtatccgg | 120 |
| agtgtgatgc agaagtacct tgcagagaga atgaaataa cctttgacaa gattttcaat | 180 |
| cagaaaattg gtttcttgct atttaaagat ttttgtttga atgaaattaa tgaagctgta | 240 |
| cctcaggtga agtttatga agagataaag gaatatgaaa aacttgataa tgaggaagac | 300 |
| cgcctttgca gaagtcgaca aatttatgat gcctacatca tgaaggaact tctttcctgt | 360 |
| tcacatcctt tctcaaagca agctgtagaa cacgtacaaa gtcatttatc caagaaacaa | 420 |
| gtgacatcaa ctctttttca gccatacata gaagaaattt gtgaaagcct tcgaggtgac | 480 |
| atttttcaaa aatttatgga aagtgacaag ttcactagat tttgtcagtg gaaaaacgtt | 540 |
| gaattaaata tccatttgac catgaatgag ttcagtgtgc ataggattat tggacgagga | 600 |
| ggattcgggg aagtttatgg ttgcaggaaa gcagacactg gaaaaatgta tgcaatgaaa | 660 |
| tgcttagata agaagaggat caaaatgaaa caaggagaaa cattagcttt aaatgaaaga | 720 |
| atcatgttgt ctcttgtcag cacaggagac tgtcctttca ttgtatgtat gacctatgcc | 780 |
| ttccataccc cagataaact ctgcttcatc ctggatctga tgaacggggg cgatttgcac | 840 |
| taccaccttt cacaacacgg tgtgttctct gagaaggaga tgcggtttta tgccactgaa | 900 |
| atcattctgg gtctggaaca cgtgcacaat cggtttgttg tctacagaga tttgaagcca | 960 |
| gcaaatattc tcttggatga acatggacac gcaagaatat cagatcttgg tcttgcctgc | 1020 |
| gattttttcca aaagaagcc tcatgcgagt gttggcaccc atgggtacat ggctcccgag | 1080 |
| gtgctgcaga aggggacggc ctatgacagc agtgccgact ggttctccct gggctgcatg | 1140 |
| cttttcaaac ttctgagagg tcacagccct ttcagacaac ataaaaccaa agacaagcat | 1200 |
| gaaattgacc gaatgacact caccgtgaat gtggaacttc cagacacctt ctctcctgaa | 1260 |
| ctgaagtccc ttttggaggg cttgcttcag cgagacgtta gcaagcggct gggctgtcac | 1320 |
| ggaggcggct cacaggaagt aaaagagcac agcttttca aggtgttga ctggcagcat | 1380 |
| gtctacttac aaaagtaccc accacccttg attcctcccc ggggagaagt caatgctgct | 1440 |
| gatgcctttg atattggctc atttgatgaa gaggatacca aagggattaa gctacttgat | 1500 |
| tgcgaccaag aactctacaa gaacttccct ttggtcatct ctgaacgctg gcagcaagaa | 1560 |
| gtaacggaaa cagtttatga agcagtaaat gcagacacag ataaaatcga ggccaggaag | 1620 |
| agagctaaaa ataagcaact tggccacgaa gaagattacg ctctggggaa ggactgtatt | 1680 |
| atgcacgggt acatgctgaa actgggaaac ccatttctga ctcagtggca gcgtcgctat | 1740 |
| ttttacctct ttccaaatag acttgaatgg agaggagagg gagagtcccg gcaaaattta | 1800 |
| ctgacaatgg aacagattct ctctgtggaa gaaactcaaa ttaaagacaa aaaatgcatt | 1860 |
| ttgttcagaa taaaggagg gaaacaattt gtcttgcaat gtgagagtga tccagagttt | 1920 |
| gtgcagtgga gaaagagtt gaacgaaacc ttcaaggagg cccagcggct attgcgtcgt | 1980 |
| gccccgaagt tcctcaacaa acctcggtca ggtactgtgg agctcccaaa gccatccctc | 2040 |
| tgtcacagga acagcaacgg cctctga | 2067 |

<210> SEQ ID NO 3
<211> LENGTH: 688
<212> TYPE: PRT
<213> ORGANISM: Homo sapiens

<400> SEQUENCE: 3

Met Ala Asp Leu Glu Ala Val Leu Ala Asp Val Ser Tyr Leu Met Ala
1               5                   10                  15

```
Met Glu Lys Ser Lys Ala Thr Pro Ala Ala Arg Ala Ser Lys Arg Ile
             20                  25                  30

Val Leu Pro Glu Pro Ser Ile Arg Ser Val Met Gln Lys Tyr Leu Ala
         35                  40                  45

Glu Arg Asn Glu Ile Thr Phe Asp Lys Ile Phe Asn Gln Lys Ile Gly
     50                  55                  60

Phe Leu Leu Phe Lys Asp Phe Cys Leu Asn Glu Ile Asn Glu Ala Val
 65                  70                  75                  80

Pro Gln Val Lys Phe Tyr Glu Ile Lys Glu Tyr Glu Lys Leu Asp
                 85                  90                  95

Asn Glu Glu Asp Arg Leu Cys Arg Ser Arg Gln Ile Tyr Asp Ala Tyr
                100                 105                 110

Ile Met Lys Glu Leu Leu Ser Cys Ser His Pro Phe Ser Lys Gln Ala
                115                 120                 125

Val Glu His Val Gln Ser His Leu Ser Lys Lys Gln Val Thr Ser Thr
            130                 135                 140

Leu Phe Gln Pro Tyr Ile Glu Glu Ile Cys Glu Ser Leu Arg Gly Asp
145                 150                 155                 160

Ile Phe Gln Lys Phe Met Glu Ser Asp Lys Phe Thr Arg Phe Cys Gln
                165                 170                 175

Trp Lys Asn Val Glu Leu Asn Ile His Leu Thr Met Asn Glu Phe Ser
                180                 185                 190

Val His Arg Ile Ile Gly Arg Gly Gly Phe Gly Glu Val Tyr Gly Cys
            195                 200                 205

Arg Lys Ala Asp Thr Gly Lys Met Tyr Ala Met Lys Cys Leu Asp Lys
            210                 215                 220

Lys Arg Ile Lys Met Lys Gln Gly Glu Thr Leu Ala Leu Asn Glu Arg
225                 230                 235                 240

Ile Met Leu Ser Leu Val Ser Thr Gly Asp Cys Pro Phe Ile Val Cys
                245                 250                 255

Met Thr Tyr Ala Phe His Thr Pro Asp Lys Leu Cys Phe Ile Leu Asp
                260                 265                 270

Leu Met Asn Gly Gly Asp Leu His Tyr His Leu Ser Gln His Gly Val
            275                 280                 285

Phe Ser Glu Lys Glu Met Arg Phe Tyr Ala Thr Glu Ile Ile Leu Gly
        290                 295                 300

Leu Glu His Val His Asn Arg Phe Val Val Tyr Arg Asp Leu Lys Pro
305                 310                 315                 320

Ala Asn Ile Leu Leu Asp Glu His Gly His Ala Arg Ile Ser Asp Leu
                325                 330                 335

Gly Leu Ala Cys Asp Phe Ser Lys Lys Pro His Ala Ser Val Gly
            340                 345                 350

Thr His Gly Tyr Met Ala Pro Glu Val Leu Gln Lys Gly Thr Ala Tyr
        355                 360                 365

Asp Ser Ser Ala Asp Trp Phe Ser Leu Gly Cys Met Leu Phe Lys Leu
    370                 375                 380

Leu Arg Gly His Ser Pro Phe Arg Gln His Lys Thr Lys Asp Lys His
385                 390                 395                 400

Glu Ile Asp Arg Met Thr Leu Thr Val Asn Val Glu Leu Pro Asp Thr
                405                 410                 415

Phe Ser Pro Glu Leu Lys Ser Leu Leu Glu Gly Leu Leu Gln Arg Asp
                420                 425                 430

Val Ser Lys Arg Leu Gly Cys His Gly Gly Gly Ser Gln Glu Val Lys
```

```
                435               440               445
Glu His Ser Phe Phe Lys Gly Val Asp Trp Gln His Val Tyr Leu Gln
            450               455               460
Lys Tyr Pro Pro Pro Leu Ile Pro Pro Arg Gly Glu Val Asn Ala Ala
465               470               475               480
Asp Ala Phe Asp Ile Gly Ser Phe Asp Glu Asp Thr Lys Gly Ile
                485               490               495
Lys Leu Leu Asp Cys Asp Gln Glu Leu Tyr Lys Asn Phe Pro Leu Val
            500               505               510
Ile Ser Glu Arg Trp Gln Gln Val Thr Glu Thr Val Tyr Glu Ala
            515               520               525
Val Asn Ala Asp Thr Asp Lys Ile Glu Ala Arg Lys Arg Ala Lys Asn
530               535               540
Lys Gln Leu Gly His Glu Asp Tyr Ala Leu Gly Lys Asp Cys Ile
545               550               555               560
Met His Gly Tyr Met Leu Lys Leu Gly Asn Pro Phe Leu Thr Gln Trp
                565               570               575
Gln Arg Arg Tyr Phe Tyr Leu Phe Pro Asn Arg Leu Glu Trp Arg Gly
            580               585               590
Glu Gly Glu Ser Arg Gln Asn Leu Leu Thr Met Glu Gln Ile Leu Ser
            595               600               605
Val Glu Glu Thr Gln Ile Lys Asp Lys Lys Cys Ile Leu Phe Arg Ile
            610               615               620
Lys Gly Gly Lys Gln Phe Val Leu Gln Cys Glu Ser Asp Pro Glu Phe
625               630               635               640
Val Gln Trp Lys Lys Glu Leu Asn Glu Thr Phe Lys Glu Ala Gln Arg
                645               650               655
Leu Leu Arg Arg Ala Pro Lys Phe Leu Asn Lys Pro Arg Ser Gly Thr
            660               665               670
Val Glu Leu Pro Lys Pro Ser Leu Cys His Arg Asn Ser Asn Gly Leu
            675               680               685

<210> SEQ ID NO 4
<211> LENGTH: 1080
<212> TYPE: DNA
<213> ORGANISM: Homo sapiens

<400> SEQUENCE: 4
atgactctgg actccatcat ggcgtgctgc ctgagcgagg aggccaagga agcccggcgg    60
atcaacgacg agatcgagcg gcagctccgc agggacaagc gggacgcccg ccgggagctc   120
aagctgctgc tgctcgggac aggagagagt ggcaagagta cgtttatcaa gcagatgaga   180
atcatccatg ggtcaggata tctctgatga gataaaaggg gcttcaccaa gctggtgtat   240
cagaacatct tcacggccat gcaggccatg atcacagcca tggacacact caagatccca   300
tacaagtgtg agcacaataa ggctcatgca caattagttc gagaagttga tgtggagaag   360
gtgtctgctt ttgagaatcc atatgtagat gcaataaaga gtttatggaa tgatcctgga   420
atccaggaat gctatgatag cgacgagaa tatcaattat ctgactctac caaatactat   480
cttaatgact tggaccgcgt agctgaccct gcctacctgc ctacgcaaca agatgtgctt   540
agagttcgag tccccaccac agggatcatc gaataccct tgacttaca aagtgtcatt   600 ttcagaatgg tcgatgtagg gggccaaagg tcagagagaa gaaaatggat acactgcttt   660
gaaaatgtca cctctatcat gtttctagta gcgcttagtg aatatgatca agttctcgtg   720
```

```
gagtcagaca atgagaaccg aatggaggaa agcaaggctc tctttagaac aattatcaca    780 taccectggt tccagaactc ctcggttatt ctgttcttaa acaagaaaga tcttctagag    840
gagaaaatca tgtattccca tctagtcgac tacttcccag aatatgatgg accccagaga    900
gatgcccagg cagcccgaga attcattctg aagatgttcg tggacctgaa cccagacagt    960
gacaaaatta tctactccca cttcacgtgt gccacagaca ccgagaatgt ccgctttgtc   1020
tttgcagccg tcaaggacac catcctccag ctgaacctga aggagtacaa tctggtctaa   1080

<210> SEQ ID NO 5
<211> LENGTH: 1080
<212> TYPE: DNA
<213> ORGANISM: Homo sapiens

<400> SEQUENCE: 5
atgactctgg agtccatcat ggcgtgttgc ctgagcgatg aggtgaagga gtccaagcgg     60
atcaacgccg agatcgagaa gcagctgcgc cgggacaagc gcgacgcccg cgcgagctc    120 aagctgctgc tgctcggcac gggcgagagc gggaagagca cgttcatcaa gcagatgcgc    180
atcatccacg gcgccggcta ctcggaggag acaagcgcg gcttcaccaa gctcgtctac    240
cagaacatct tcaccgccat gcaggccatg atccgggcca tggagacgct caagatcctc    300
tacaagtacg agcagaacaa ggccaatgcg ctcctgatcc gggaggtgga cgtggagaag    360
gtgaccacct tcgagcatca gtacgtcagt gccatcaaga ccctgtggga ggacccgggc    420
atccaggaat gctacgaccg caggcgcgag taccagctct ccgactctgc caagtactac    480
ctgaccgacg ttgaccgcat cgccaccttg ggctacctgc ccacccagca ggacgtgctg    540
cgggtccgcg tgcccaccac cggcatcatc gagtacccct tcgacctgga aacatcatc    600 ttccggatgg tggatgtggg gggccagcgg tcggagcgga ggaagtggat ccactgcttt    660
gagaacgtga catccatcat gtttctcgtc gccctcagcg aatacgacca agtcctggtg    720
gagtcggaca acgagaaccg gatggaggag agcaaagccc tgttccggac catcatcacc    780 taccectggt tccagaactc ctccgtcatc ctcttcctca acaagaagga cctgctggag    840
gacaagatcc tgtactcgca cctggtggac tacttccccg agttcgatgg tccccagcgg    900
gacgcccagg cggcgcggga gttcatcccg aagatgttcg tggacctgaa ccccgacagc    960
gacaagatca tctactcaca cttcacgtgt gccaccgaca cggagaacat ccgcttcgtg   1020
ttcgcggccg tgaaggacac catcctgcag ctgaacctga aggagtacaa tctggtctaa   1080

<210> SEQ ID NO 6
<211> LENGTH: 4105
<212> TYPE: DNA
<213> ORGANISM: Homo sapiens

<400> SEQUENCE: 6
gaattcgcgg ccgcctcttg cggtcccaga gtggagtgga aggtctggag ctttgggagg     60
agacggggag gacagactgg aggcgtgttc ctccggagtt ttcttttcg tgcgagccct    120 cgcgcgcgcg tacagtcatc ccgctggtct gacgattgtg gagaggcggt ggagaggctt    180
catccatccc acccggtcgt cgccggggat tggggtccca gcgacacctc cccgggagaa    240
gcagtgccca ggaagttttc tgaagccggg gaagctgtgc agccgaagcc gccgccgcgc    300
cggagcccgg gacaccggcc accctccgcg ccacccaccc tcgctttctc cggcttcctc    360
tggcccaggc gccgcgcgga cccggcagct gtctgcgcac gccgagctcc acggtgaaaa    420
aaaaagtgaa ggtgtaaaag cagcacaagt gcaataagag atatttcctc aaatttgcct    480
```

-continued

| | |
|---|---|
| caagatggaa accctttgcc tcagggcatc cttttggctg gcactggttg gatgtgtaat | 540 |
| cagtgataat cctgagagat acagcacaaa tctaagcaat catgtggatg atttcaccac | 600 |
| ttttcgtggc acagagctca gcttcctggt taccactcat caacccacta atttggtcct | 660 |
| acccagcaat ggctcaatgc acaactattg cccacagcag actaaaatta cttcagcttt | 720 |
| caaatacatt aacactgtga tatcttgtac tattttcatc gtgggaatgg tggggaatgc | 780 |
| aactctgctc aggatcattt accagaacaa atgtatgagg aatggcccca acgcgctgat | 840 |
| agccagtctt gcccttggag acctatcta tgtggtcatt gatctcccta tcaatgtatt | 900 |
| taagctgctg gctgggcgct ggcctttga tcacaatgac tttggcgtat ttctttgcaa | 960 |
| gctgttcccc tttttgcaga agtcctcggt ggggatcacc gtcctcaacc tctgcgctct | 1020 |
| tagtgttgac aggtacagag cagttgcctc ctggagtcgt gttcagggaa ttgggattcc | 1080 |
| tttggtaact gccattgaaa ttgtctccat ctggatcctg tcctttatcc tggccattcc | 1140 |
| tgaagcgatt ggcttcgtca tggtaccctt tgaatatagg ggtgaacagc ataaaacctg | 1200 |
| tatgctcaat gccacatcaa aattcatgga gttctaccaa gatgtaaagg actggtggct | 1260 |
| cttcgggttc tatttctgta tgcccttggt gtgcactgcg atcttctaca ccctcatgac | 1320 |
| ttgtgagatg ttgaacagaa ggaatggcag cttgagaatt gccctcagtg aacatcttaa | 1380 |
| gcagcgtcga gaagtggcaa aaacagtttt ctgcttggtt gtaattttg ctctttgctg | 1440 |
| gttccctctt cacttaagcc gtatattgaa gaaaactgtg tataacgaaa tggacaagaa | 1500 |
| ccgatgtgaa ttacttagtt tcttactgct catggattac atcggtatta acttggcaac | 1560 |
| catgaattca tgtataaacc ccatagctct gtattttgtg agcaagaaat ttaaaaattg | 1620 |
| tttccagtca tgcctctgct gctgctgtta ccagtccaaa agtctgatga cctcggtccc | 1680 |
| catgaacgga acaagcatcc agtggaagaa ccacgatcaa acaaccaca acacagaccg | 1740 |
| gagcagccat aaggacagca tgaactgacc acccttagaa gcactcctcg gtactcccat | 1800 |
| aatcctctcg gagaaaaaaa tcacaaggca actgtgactc cgggaatctc ttctctgatc | 1860 |
| cttcttcctt aattcactcc cacacccaag aagaaatgct ttccaaaacc gcaaggtaga | 1920 |
| ctggtttatc cacccacaac atctacgaat cgtacttctt taattgatct aatttacata | 1980 |
| ttctgcgtgt tgtattcagc actaaaaaat ggtgggagct gggggagaat gaagactgtt | 2040 |
| aaatgaaacc agaaggatat ttactacttt tgcatgaaaa tagagctttc aagtacatgg | 2100 |
| ctagctttta tggcagttct ggtgaatgtt caatgggaac tggtcaccat gaaactttag | 2160 |
| agattaacga caagatttc tactttttt aagtgatttt ttgtccttca gccaaacaca | 2220 |
| atatgggctc aggtcacttt tatttgaaat gtcatttggt gccagtattt tttaactgca | 2280 |
| taatagccta acatgattat ttgaacttat ttacacatag tttgaaaaaa aaagacaaa | 2340 |
| aatagtattc aggtgagcaa ttagattagt attttccacg tcactattta tttttttaaa | 2400 |
| acacaaattc taaagctaca acaaatacta caggccctta agcacagtc tgatgacaca | 2460 |
| tttggcagtt taatagatgt tactcaaaga atttttaag aactgtattt tattttttaa | 2520 |
| atggtgtttt attcaagggg accttgaaca tgttttgtat gttaaattca aaagtaatgc | 2580 |
| ttcaatcaga tagttctttt tcacaagttc aatactgttt ttcatgtaaa ttttgtatga | 2640 |
| aaaatcaatg tcaagtacca aaatgttaat gtatgtgtca tttaactctg cctgagactt | 2700 |
| tcagtgcact gtatatagaa gtctaaaaca cacctaagag aaaaagatcg aatttttcag | 2760 |
| atgattcgga aattttcatt caggtatttg taatagtgac atatatatgt atatacatat | 2820 |

```
cacctcctat tctcttaatt tttgttaaaa tgttaactgg cagtaagtct tttttgatca    2880
ttcccttttc catataggaa acataatttt gaagtggcca gatgagttta tcatgtcagt    2940
gaaaaataat tacccacaaa tgccaccagt aacttaacga ttcttcactt cttggggttt    3000
tcagtatgaa cctaactccc cacccccaaca tctccctccc acattgtcac catttcaaag   3060
ggcccacagt gacttttgct ggcatttttc ccagatgttt acagactgtg agtacagcag    3120
aaaatctttt actagtgtgt gtgtgtatat atataaacaa ttgtaaattt cttttagccc    3180
atttttctag actgtctctg tggaatatat ttgtgtgtgt gatatatgca tgtgtgtgat    3240
ggtatgtatg gatttaatct aatctaataa ttgtgccccg cagttgtgcc aaagtgcata    3300
gtctgagcta aaatctaggt gattgttcat catgacaacc tgcctcagtc cattttaacc    3360
tgtagcaacc ttctgcattc ataaatcttg taatcatgtt accattacaa atgggatata    3420
agaggcagcg tgaaagcaga tgagctgtgg actagcaata tagggttttg tttggttggt    3480
tggtttgata aagcagtatt tggggtcata ttgtttcctg tgctggagca aaagtcatta    3540
cactttgaag tattatattg ttcttatcct caattcaatg tggtgatgaa attgccaggt    3600
tgtctgatat ttcttcaga  cttcgccaga cagattgctg ataataaatt aggtaagata    3660
atttgttggg ccatatttta ggacaggtaa aataacatca ggttccagtt gcttgaattg    3720
caaggctaag aagtactgcc ttttgtgtg  ttagcagtca aatctattat tccactggcg    3780
catcatatgc agtgatatat gcctataata taagccatag gttcacacca ttttgtttag    3840
acaattgtct ttttttcaag atgctttgtt tctttcatat gaaaaaaatg catttttataa   3900 attcagaaag tcatagattt ctgaaggcgt caacgtgcat tttatttatg gactggtaag    3960
taactgtggt ttactagcag gaatatttcc aatttctacc tttactacat cttttcaaca    4020
agtaactttg tagaaatgag ccagaagcca aggccctgag ttggcagtgg cccataagtg    4080
taaaataaaa gtttacagaa acctt                                          4105
```

<210> SEQ ID NO 7
<211> LENGTH: 1603
<212> TYPE: DNA
<213> ORGANISM: Homo sapiens

<400> SEQUENCE: 7

```
caggaaggag tttcgacccg cgctggcgag tcatgagcgc caagtttccc actggcgcgc      60
aaacttgagt tacttttgag cgtggatact ggcgaagagg ctgcgggcgg tattagcgtt     120
tgcagcgact tggctcgggc agctgaccca agtgtcctgt cttccttcct ctgcttgtct     180
ctaggctctg aaactgcgga gcggccaccg gacgccttct ggagcaggta gcagcatgca     240
gccgcctcca agtctgtgcg gacgcgccct ggttgcgctg gttcttgcct gcggcctgtc     300
gcggatctgg ggagaggaga gaggcttccc gcctgacagg gccactccgc ttttgcaaac     360
cgcagagata atgacgccac ccactaagac cttatggccc aagggttcca acgccagtct     420
ggcgcggtcg ttggcacctg cggaggtgcc taaaggagac aggacggcag gatctccgcc     480
acgcaccatc tcccctcccc cgtgccaagg acccatcgag atcaaggaga ctttcaaata     540
catcaacacg ttgtgtcct  gccttgtgtt cgtgctgggg atcatcggga actccacact     600
tctgagaatt atctacaaga acaagtgcat gcgaaacggt cccaatatct tgatcgccag     660
cttggctctg ggagacctgc tgcacatcgt cattgacatc cctatcaatg tctacaagct     720
gctggcagag gactggccat ttggagctga gatgtgtaag ctggtgcctt tcatacagaa     780
agcctccgtg ggaatcactg tgctgagtct atgtgctctg agtattgaca gatatcgagc     840
```

-continued

```
tgttgcttct tggagtagaa ttaaaggaat tggggttcca aaatggacag cagtagaaat    900
tgttttgatt tgggtggtct ctgtggttct ggctgtccct gaagccatag gttttgatat    960
aattacgatg gactacaaag gaagttatct gcgaatctgc ttgcttcatc ccgttcagaa   1020
gacagctttc atgcagtttt acaagacagc aaaagattgg tggctgttca gtttctattt   1080
ctgcttgcca ttggccatca ctgcattttt ttatacacta atgacctgtg aaatgttgag   1140
aaagaaaagt ggcatgcaga ttgctttaaa tgatcaccta aagcagagac gggaagtggc   1200
caaaaccgtc ttttgcctgg tccttgtctt tgccctctgc tggcttcccc ttcacctcag   1260
caggattctg aagctcactc tttataatca gaatgatccc aatagatgtg aactttgag    1320 ctttctgttg gtattggact atattggtat caacatggct tcactgaatt cctgcattaa   1380
cccaattgct ctgtatttgg tgagcaaaag attcaaaaac tgctttaagt catgcttatg   1440
ctgctggtgc cagtcatttg aagaaaaaca gtccttggag gaaaagcagt cgtgcttaaa   1500
gttcaaagct aatgatcacg gatatgacaa cttccgttcc agtaataaat acagctcatc   1560
ttgaaagaaa aaaaaaaaaa aaaaaaaaaa aaaaaaaaa aaa                      1603
```

<210> SEQ ID NO 8
<211> LENGTH: 19
<212> TYPE: RNA
<213> ORGANISM: artificial
<220> FEATURE:
<223> OTHER INFORMATION: completely synthesized

<400> SEQUENCE: 8
ugacuucagu gugcaucga                                                  19

<210> SEQ ID NO 9
<211> LENGTH: 19
<212> TYPE: RNA
<213> ORGANISM: artificial
<220> FEATURE:
<223> OTHER INFORMATION: completely synthesized

<400> SEQUENCE: 9
ucgaugcaca cugaaguca                                                  19

METHODS OF IDENTIFYING COMPOUNDS FOR PRODUCING INSULIN SENSITIZATION

CROSS-REFERENCE TO RELATED APPLICATIONS

This application is a national of PCT Application Serial No. PCT/US2005/021560 filed on Jun. 17, 2005, which claims priority from U.S. Provisional Application Ser. No. 60/580,975 filed on Jun. 17, 2004, which are incorporated herein by reference in their entirety.

STATEMENT REGARDING FEDERALLY SPONSORED RESEARCH OR DEVELOPMENT

This invention was made in part with Government support under National Institutes of Health Grant DK 33651. The Government has certain rights in the invention.

INCORPORATION-BY-REFERENCE OF MATERIAL SUBMITTED ON A COMPACT DISC

The Sequence Listing, which is a part of the present disclosure, includes a computer readable form and a written sequence listing comprising nucleotide and/or amino acid sequences of the present invention. The sequence listing information recorded in computer readable form is identical to the written sequence listing. The subject matter of the Sequence Listing is incorporated herein by reference in its entirety.

BACKGROUND OF THE INVENTION

1. Field of the Invention

This invention relates to methods and compositions for regulating the insulin signaling pathway and for the treatment of metabolic syndrome, including insulin resistance and diabetes mellitus type II.

2. Description of Related Art

G protein-coupled receptor kinases (GRKs) play a central role in desensitizing G protein-coupled receptors (GPCRs). G protein coupled receptor kinases (GRKs) are enzymes which phosphorylate agonist-activated 7TMRs, leading to 7TMR internalization and inhibition of further G protein activation. GRKs also have other functions to regulate 7TMR signaling. Thus, GRKs directly bind to trimeric G protein 1-subunits, and inhibit G protein function. GRKs also phosphorylate specific C-terminal serine residues of agonist-activated GPCRs, leading to increased binding of β-arrestin. GRK-induced phosphorylation of the GPCR, with subsequent β-arrestin association, uncouples the receptors from further G protein association, and also promotes internalization of the GPCR. It has also been shown that GRKs have additional functions to regulate GPCR signaling. Thus, it is believed that GRKs can contain RGS domains which mediate binding to Gα subunits, inhibiting G protein function.

Endothelin-1 (ET-1) is a vascular polypeptide primarily secreted by endothelial cells. Elevated plasma ET-1 levels have been reported in patients with insulin resistance, such as type 2 diabetes, obesity, and hypertension. ET-1 initiates its actions by binding to the 7 transmembrane receptor (7TMR), endothelin type A receptor.

The insulin receptor, on the other hand, is a receptor tyrosine kinase (RTK), which activates its signaling cascade by phosphorylating various intracellular substrates, including IRS-1, IRS-2, Shc, and G protein-q/11 α-subunit (Gαq/11). Insulin also promotes glucose transport by stimulating translocation of GLUT4 proteins to the cell surface. Activated insulin receptor is believed to be able to phosphorylate the heterotrimeric protein component Gαq/11, leading to activation of cdc42, and PI3-kinase with downstream glucose transport stimulation.

Although much is known about these biochemical components of metabolic syndrome, what has not been determined is a mechanism for producing insulin sensitivity or attenuation of insulin resistance to provide a target for drug studies for the treatment of metabolic syndrome. Therefore, what are needed are methods for designing such drugs and treatments for metabolic syndrome and methods for screening for insulin resistance levels.

BRIEF SUMMARY OF THE INVENTION

Accordingly, it is an object of the invention to overcome these and other, problems associated with the related art. These and other objects, features and technical advantages are achieved by providing G protein-coupled receptor kinase 2 (GRK2) as an endogenous protein inhibitor of insulin signaling which can lead to metabolic syndrome, including insulin resistance.

The invention provides a method for identifying a candidate insulin sensitizing compound, the method comprising: (a) contacting GRK2 or biologically-active fragment with a known compound that binds GRK2 to form an assay mixture, (b) contacting the assay mixture with a test compound, and (c) determining the ability of the test compound to interact with GRK2, wherein an increased ability of the test compound to interact with GRK2 in the presence of the known compound indicates that the test compound is an insulin sensitizing compound. In accordance with a further aspect of the invention, the known compound can be selected from the group consisting of Gαq/11, endothelin receptor type A and endothelin receptor type B.

The invention also provides a method for identifying a candidate insulin sensitizing compound, the method comprising: (a) contacting one of endothelin receptor type A or endothelin receptor type B, or biologically-active fragments thereof, with a known compound that binds endothelin receptor type A or endothelin receptor type B to form an assay mixture, (b) contacting the assay mixture with a test compound, and (c) determining the ability of the test compound to interact with one of endothelin receptor type A or endothelin receptor type B, wherein an increased ability of the test compound to interact with one of endothelin receptor type A or endothelin receptor type B in the presence of the known compound indicates that the test compound is an insulin sensitizing compound. In accordance with a further aspect of the invention, the known compound can be ET-1.

The invention further provides a method for identifying a candidate insulin sensitizing compound, the method comprising: (a) performing a structure based drug design using a three dimensional structure determined for a crystal of GRK2. In accordance with a further aspect of the invention, the three dimensional structure can comprise atomic coordinates of Protein Data Bank Accession No. 1 OMW. In a further aspect, the method can further comprise: (b) contacting a test compound identified by the structure based drug design with a cell comprising GRK2 or a variant or fragment thereof; and (c) detecting inhibition of at least one activity of the GRK2, variant or fragment thereof.

In addition, the invention provides a method for identifying a candidate insulin sensitizing compound, the method comprising: a) contacting a test compound with Gαq/11 and one of insulin receptor or GRK2; and b) detecting the level of phosphorylation of Gαq/11 in the presence of said test compound and one of insulin receptor or GRK2 as compared to the level of phosphorylation in the absence of said test compound, wherein a decreased level of phosphorylation in the presence of said test compound indicates that the test compound is an insulin sensitizing compound. In accordance with a further aspect of the invention, the compound can be a GRK2 RGS binding domain mimic, further wherein Gαq/11 phosphorylation is not inhibited.

The invention also provides a method for identifying a candidate insulin sensitizing, compound, the method comprising: a) contacting a test compound with GRK2 and one of endothelin receptor type A or endothelin receptor type B; and b) detecting the level of phosphorylation of GRK2 in the presence of said test compound and one of endothelin receptor type A or endothelin receptor type B as compared to the level of phosphorylation in the absence of said test compound, wherein a decreased level of phosphorylation in the presence of said test compound indicates that the test compound is an insulin sensitizing compound.

In various aspects of the invention, the methods above can be performed wherein the test compound is an antibody. In accordance with yet another aspect of the invention, the antibody can be a monoclonal antibody. In various aspects of the invention, the methods above can be performed wherein the test compound is selected from the group consisting of a ribozyme, antisense compound, triplex-forming molecule, siRNA, and aptamer. In a further aspect of the invention, the siRNA can comprises the sequence of SEQ ID NO: 8.

In various aspects of the invention, the methods above can be performed wherein the candidate compound is formulated in combination with an agent selected from the group consisting of a pharmaceutically acceptable carrier, a controlled-release component, a pharmaceutically acceptable salt, and any combination thereof.

The invention also provides a method for treating metabolic syndrome, the method comprising administering a therapeutically effectively amount of an insulin sensitizing compound to a patient in need thereof. In various aspects of the invention, the insulin sensitizing compound can be identified by a method of claim 1, 3, 5, 8 or 10. In some aspects, the metabolic syndrome can be insulin resistance and/or Type 2 diabetes mellitus. In some aspects, the insulin sensitizing compound can be an antibody having specificity for GRK2. In various aspects, the insulin sensitizing compound can be selected from the group consisting of a ribozyme, antisense compound, triplex-forming molecule, siRNA, and aptamer, wherein the insulin sensitizing compound has specificity for GRK2. In particular, the siRNA can comprise the sequence of SEQ ID NO: 8. In various aspects, the compound can be delivered to the subject in combination with an agent selected from the group consisting of a pharmaceutically acceptable carrier, a controlled-release component, a pharmaceutically acceptable salt, and any combination thereof. In some aspects, the compound is formulated as a pro-drug. In various aspects, the compound can be administered by a method selected from the group consisting of parenteral administration, oral administration, controlled-release administration, inhalation administration, depot administration, topical administration, suppository administration, and any combination thereof.

The invention also provides a method for expressing a siRNA specific to a GRK2 gene in a cell in vitro or in vivo, comprising: providing an expression vector encoding a siRNA specific to a GRK2 gene; introducing the vector into a cell in vitro or in vivo; and maintaining the cell in vitro or in vivo under conditions permitting expression of the siRNA in the cell.

The invention also provides a method for identifying a subject having or susceptible to acquiring metabolic syndrome, the method comprising detecting a level of GRK2 activity in the subject and comparing the subject GRK2 activity level to a predetermined normal standard, wherein a GRK2 activity level above the normal standard indicates that the subject has or is susceptible to acquiring metabolic syndrome.

The invention further provides a purified antibody that binds specifically to the RGS domain of GRK2. In addition, the invention provides a transgenic non-human animal whose somatic and germ cells comprise a disrupted GRK2 gene, the disruption being sufficient to inhibit the binding of GRK2 to Gαq/11, said disrupted gene being introduced into the non-human animal or an ancestor of the non-human animal at an embryonic stage, wherein the non-human animal, if homozygous for the disrupted GRK2 gene, is infertile. In some aspects, the non-human animal can be selected from the group consisting of a mouse, pig, rat, hamster, goat, cow, and chicken.

The invention also provides an expression vector comprising a nucleic acid encoding the ribonucleotide sequence of SEQ ID NO: 8, wherein the nucleic acid is operably linked to an expression control sequence. The invention further provides a cultured cell comprising the vector above. Further provided is a cultured cell comprising the nucleic acid above. In addition, the invention provides a cultured cell comprising the ribonucleic acid of SEQ ID NO: 8.

The invention provides an insulin sensitizing compound identified by any of the methods described above. In addition, the invention provides a kit comprising an insulin sensitizing compound identified by any of methods described above.

These and other features, aspects and advantages of the present invention will become better understood with reference to the following description, examples and appended claims.

BRIEF DESCRIPTION OF THE SEVERAL VIEWS OF THE DRAWINGS

FIG. 10 depicts the effects of wild type- or kinase deficient-GRK2 overexpression on Gαq/11-cdc42-PI3-kinase pathway in 3T3-L1 adipocytes.

DETAILED DESCRIPTION OF THE INVENTION

Abbreviations and Definitions

Figure 1:
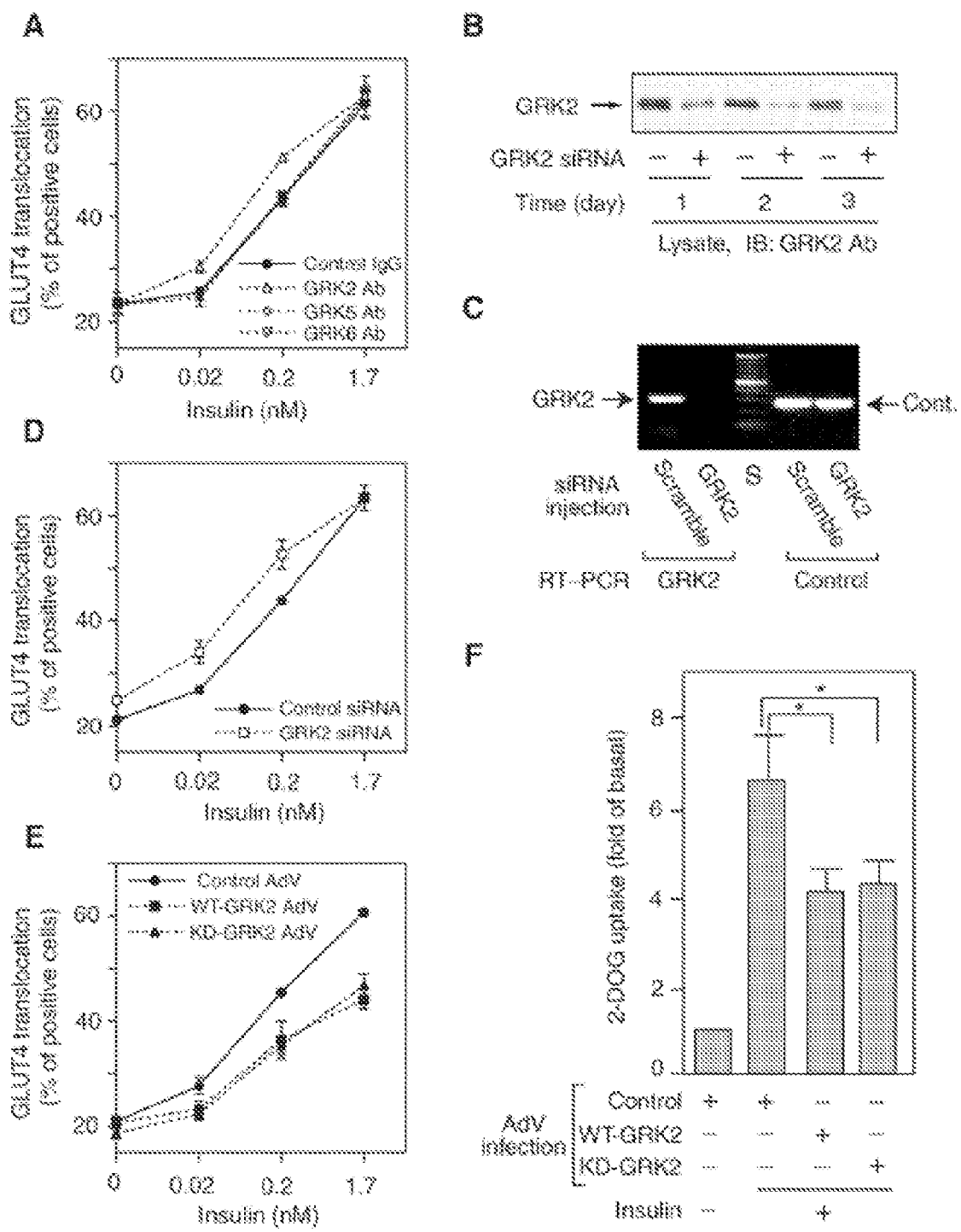
FIG. 1 depicts the effects of GRK2 on insulin-stimulated GLUT4 translocation and 2-deoxyglucose uptake in 3T3-L1 adipocytes.
Figure 2:
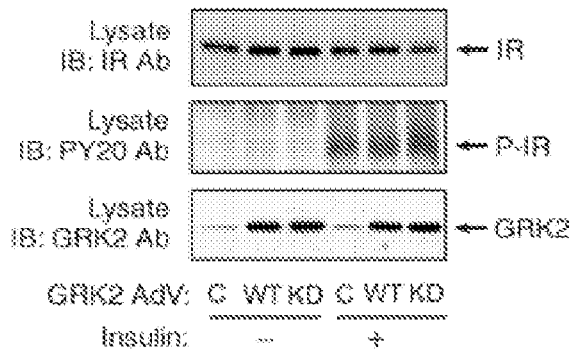
FIG. 2 depicts the effects of wild type- or kinase deficient GRK2 overexpression on insulin receptor and IRS-1-PI3-kinase pathway in 3T3-L1 adipocytes.
Figure 2:
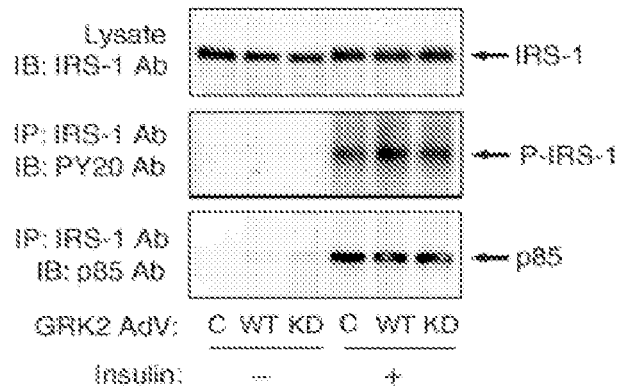
Figure 2:
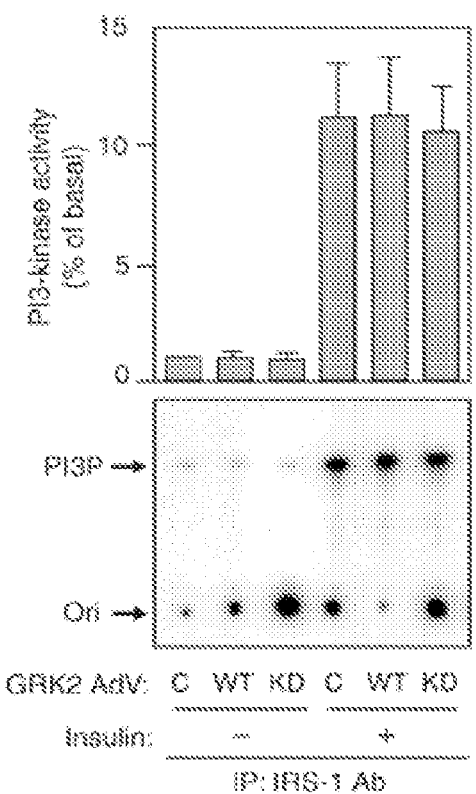

To facilitate the understanding of the invention, a number of terms and abbreviations as used herein are defined below and have the following meanings:

Abs: As used herein, the term "Abs" refers to antibodies which may be, e.g., a single anti-GRK2 monoclonal Abs (including agonist, antagonist, and neutralizing Abs), anti-GRK2 antibody compositions with polyepitopic specificity, single chain anti-GRK2 Abs, and fragments of anti-GRK2 Abs. A "monoclonal antibody" refers to an antibody obtained from a population of substantially homogeneous Abs, i.e., the individual Abs comprising the population are identical except for naturally-occurring mutations that may be present in minor amounts Active Polypeptide: As used herein, the term "active polypeptide" refers to a, e.g., GRK2, GRK2 fragment or GRK2 variant which retains a biological and/or an immunological activity of native or naturally occurring GRK2. Immunological activity refers to the ability to induce the production of an antibody against an antigenic epitope possessed by a native GRK2; biological activity refers to a function, either inhibitory or stimulatory, caused by a native GRK2 that excludes immunological activity. A biological activity of GRK2 includes, for example, its regulation of insulin signaling disclosed herein.

Control Sequences: As used herein, the term "control sequences" refers to DNA sequences that enable the expression of an operably-linked coding sequence in a particular host organism. Prokaryotic control sequences include promoters, operator sequences, and ribosome binding sites. Eukaryotic cells utilize promoters, polyadenylation signals, and enhancers.

Controlled-Release Component: As used herein, the term "controlled-release component" refers to an agent that facilitates the controlled-release of a compound including, but not limited to, polymers, polymer matrices, gels, permeable membranes, liposomes, microspheres, or the like, or any combination thereof. Methods for producing compounds in combination with controlled-release components are known to those of skill in the art.

Epitope Tag: As used herein, the term "epitope tag" refers to a chimeric polypeptide fused to a "tag polypeptide". Such tags provide epitopes against which Abs can be made or are available, but do not interfere with polypeptide activity. To reduce anti-tag antibody reactivity with endogenous epitopes, the tag polypeptide is preferably unique. Suitable tag polypeptides generally have at least six amino acid residues and usually between about 8 and 50 amino acid residues, preferably between 8 and 20 amino acid residues). Examples of epitope tag sequences include HA from Influenza A virus and FLAG.

Isolated: As used herein, the term "isolated," when referred to a molecule, refers to a molecule that has been identified and separated and/or recovered from a component of its natural environment. Contaminant components of its natural environment are materials that interfere with diagnostic or therapeutic use.

Isolated Nucleic Acid: As used herein, the term "isolated nucleic acid" refers to a molecule purified from the setting in which it is found in nature and is separated from at least one contaminant nucleic acid molecule. Isolated GRK2 molecules are distinguished from the specific GRK2 molecule, as it exists in cells. However, an isolated GRK2 molecule includes GRK2 molecules contained in cells that ordinarily express the GRK2 where, for example, the nucleic acid molecule is in a chromosomal location different from that of natural cells.

Isolated or Purified Polypeptide, Protein or Fragment: As used herein, the terms "isolated" or "purified" polypeptide, protein or biologically active fragment refer to those items separated and/or recovered from a component of its natural environment. Contaminant components include materials that would typically interfere with diagnostic or therapeutic uses for the polypeptide, and may include enzymes, hormones, and other proteinaceous or non-proteinaceous materials. Preferably, the polypeptide is purified to a sufficient degree to obtain at least 15 residues of N-terminal or internal amino acid sequence. To be substantially isolated, preparations having less than 30% by dry weight of non-GRK2 contaminating material (contaminants), more preferably less than 20%, 10% and most preferably less than 5% contaminants. An isolated, recombinantly-produced GRK2 or biologically active portion is preferably substantially free of culture medium, i.e., culture medium represents less than 20%, more preferably less than about 10%, and most preferably less than about 5% of the volume of the GRK2 preparation. Examples of contaminants include cell debris, culture media, and substances used and produced during in vitro synthesis of GRK2.

Operably Linked: As used herein, the term "operably linked" refers to nucleic acid when it is placed into a functional relationship with another nucleic acid sequence. For example, a promoter or enhancer is operably-linked to a coding sequence if it affects the transcription of the sequence, or a ribosome-binding site is operably-linked to a coding sequence if positioned to facilitate translation. Generally, "operably-linked" means that the DNA sequences being linked are contiguous, and, in the case of a secretory leader, contiguous and in reading phase. However, enhancers do not have to be contiguous. Linking is accomplished by conventional recombinant DNA methods.

Pharmaceutically Acceptable: As used herein, the term "pharmaceutically acceptable" means approved by a regulatory agency of the Federal or a state government or listed in the U.S. Pharmacopeia or other generally recognized pharmacopeia for use in animals, and more particularly in humans.

Pharmaceutically Acceptable Carrier: As used herein, the term "pharmaceutically acceptable carrier" refers to a diluent, adjuvant, excipient, or vehicle with which a compound is administered. Such carriers can be sterile liquids, such as water and oils, including those of petroleum, animal, Vegetable or synthetic origin, such as peanut oil, soybean oil, mineral oil, sesame oil and the like, polyethylene glycols, glycerine, propylene glycol or other synthetic solvents. Water is a preferred carrier when a compound is administered intravenously. Saline solutions and aqueous dextrose and glycerol solutions can also be employed as liquid carriers, particularly for injectable solutions. Suitable excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. A compound, if desired, can also combine minor amounts of wetting or emulsifying agents, or pH buffering agents such as acetates, citrates or phosphates. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compounds in combination with carriers are known to those of skill in the art.

Pharmaceutically Acceptable Salt: As used herein, the term "pharmaceutically acceptable salt" includes those salts of a pharmaceutically acceptable compound formed with free amino groups such as those derived from hydrochloric, phosphoric, acetic, oxalic, tartaric acids, and those formed with free carboxyl groups such as those derived from sodium, potassium, ammonium, calcium, ferric hydroxides, isopropylamine, triethylamine, 2-ethylamino ethanol, histidine, and procaine. If the compound is basic, salts may be prepared from pharmaceutically acceptable non-toxic acids including inorganic and organic acids. Such acids include acetic, benzene-sulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric acid, p-toluenesulfonic, and the like. Particularly preferred are besylate, hydrobromic, hydrochloric, phosphoric and sulfuric acids. If the compound is acidic, salts may be prepared from pharmaceutically acceptable organic and inorganic bases. Suitable organic bases include, but are not limited to, lysine, N,N'-dibenzylethylenediamine, chloroprocaine, choline, diethanolamine, ethylenediamine, meglumine (N-methylglucamine) and procaine. Suitable inorganic bases include, but are not limited to, alkaline and earth-alkaline metals such as aluminum, calcium, lithium, magnesium, potassium, sodium and zinc. Methods for synthesizing such salts are known to those of skill in the art.

Pro-drug: As used herein, the term "pro-drug" refers to any compound which releases an active drug in vivo when such a compound is administered to a mammalian subject. Pro-drugs can be prepared, for example, by functional group modification of an active drug. The functional group may be cleaved in vivo to release the active drug compound. Pro-drugs include, for example, compounds in which a group that may be cleaved in vivo is attached to a hydroxy, amino or carboxyl group in the active drug. Examples of pro-drugs include, but are not limited to esters (e.g., acetate, methyl, ethyl, formate, and benzoate derivatives), carbamates, amides and ethers. Methods for synthesizing such pro-drugs are known to those of skill in the art.

Purified Polypeptide: As used herein, the term "purified polypeptide" refers to a molecule which is purified (1) to obtain at least 15 residues of N-terminal or internal amino acid sequence using a sequenator, or (2) to homogeneity by SDS-PAGE under non-reducing or reducing conditions using Coomassie blue or silver stain. Isolated polypeptides include those expressed heterologously in genetically-engineered cells or expressed in vitro, since at least one component of the GRK2 natural environment will not be present. Ordinarily, isolated polypeptides are prepared by at least one purification step.

Therapeutically Effective Amount: As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. More specific embodiments are included in the Pharmaceutical Preparations and Methods of Administration section below.

Methods and Compositions for Producing Insulin Sensitization

The present invention utilizes the discovery that one of the $G\alpha$ proteins, $G\alpha q/11$, is activated by the insulin receptor and can function in the process of glucose transport stimulation, and that GRK2 has an inhibitory role in insulin-stimulated glucose transport by decreasing activation of the $G\alpha q/11$ pathway. The invention also utilizes the discovery that GRK2 contributes to chronic ET-1-induced insulin resistance by enhancing IRS-1 degradation and decreasing $G\alpha q/11$ activation in 3T3-L1 adipocytes. Hence, the invention herein provides a mode of treating metabolic syndrome, which includes Type 2 diabetes mellitus and insulin resistance in human and other subjects by identifying and administering an insulin sensitizing compound which modulates GRK2 function in the insulin signaling pathway. The invention also provides polynucleotides, polypeptides, vectors, cells, tissues and organisms useful in the identification and treatment of metabolic syndrome. A number of desirable insulin sensitizing aspects are achieved by various embodiments of the present invention.

GRK2 and $G\alpha q/11$

The present invention provides for the role of GRK2 in insulin sensitization and insulin-induced glucose transport. It was discovered that GRK2 has $G\alpha q/11$ specificity, such that the inventors postulated that GRK2, by inhibiting $G\alpha q/11$ function, would be an endogenous negative regulator of insulin-stimulated glucose transport. From this discovery, a new treatment for metabolic syndrome, including insulin resistance and Type 2 diabetes mellitus, was devised.

GRKs classically phosphorylate heptahelical receptors at specific serine residues facilitating β-arrestin induced GPCR desensitization. In addition, GRKs can also contain RGS domains with specificity towards different $G\alpha$ subtypes, providing another level of interaction between GRKs and hormone signaling. Specifically, GRK2 interacts with $G\alpha q/11$ which can function as a key component in the insulin stimulated GLUT4 translocation pathway. The present invention provides that GRK2 functions as an endogenous protein inhibitor of insulin signaling to glucose transport, and that overexpression of GRK2 inhibits insulin stimulated GLUT4 translocation and glucose transport. In addition, inhibition of GRK2 by antibody microinjection, dominant negative GRK2 expression, or siRNA mediated GRK2 knockdown all sensitize 3T3-L1 adipocytes to insulin stimulation of GLUT4 translocation and activation of glucose transport. Taken together, it is demonstrated that GRK2 is a novel member of the insulin/glucose transport signaling pathway and that inhibition of GRK2 function can lead to increased insulin sensitization at the cellular level.

The present invention also provides a mechanism whereby GRK2 can exert its inhibitory effects on insulin signaling. Thus, GRK expression had no effect on insulin receptor or IRS-1 protein levels or tyrosine phosphorylation state, nor was IRS-1 associated PI3 kinase activity altered. This indicates that the inhibitory effects of GRK2 on insulin stimulated glucose transport do not involve interactions with elements of the IR/IRS-1/PI3 kinase arm of the insulin signaling pathway. In addition, GRK2 inhibits the insulin stimulated glucose transport system by interacting with the G$\alpha$q/11/cdc42/PI3 kinase pathway at the G$\alpha$q/11 step. Furthermore, because inhibition of endogenous GRK2 activity sensitizes 3T3-L1 adipocytes to insulin stimulation of GLUT4 translocation and glucose transport, these the insulin stimulated G$\alpha$q/11 signaling pathway is a physiologically important mediator of this key biologic effect of insulin.

GRK2 consists of three domains; an amino terminal RGS domain, a central kinase domain, and a carboxy terminal PH domain. Kinase inactive GRK2 retains the full activity to inhibit insulin stimulated glucose transport, demonstrating that the kinase domain of GRK2 is not responsible for this function. Furthermore, a deletion mutant which contains the intact kinase and PH domain of GRK2, but is missing the RGS domain ($\Delta$GRK2), reveals that when expressed in cells, transport stimulation was not inhibited. These experiments confirm the non-essentiality of the kinase domain and also show that the PH domain of GRK2 is not required for this function, since the PH domain was intact in the $\Delta$GRK2 construct. Further evidence indicates that GRK2 RGS domain binding to G$\alpha$q/11 is responsible for the inhibitory effects of GRK2 on insulin stimulated glucose transport.

GRK2 is an endogenous protein inhibitor of the insulin signaling pathway leading to glucose transport stimulation. Because inhibition of endogenous GRK2 leads to cellular insulin sensitization, one of skill in the art will recognize that GRK2 is an important target for metabolic syndrome therapeutics. Chemical inhibitors of GRK2 would be expected to act as insulin sensitizers which could have beneficial effects in a wide variety of insulin resistant conditions, including Type 2 diabetes mellitus.

GRK2 and ET-1

G$\alpha$q/11 is activated by tyrosine phosphorylation at the C-terminus. Because seven transmembrane receptors (7TMRs) do not have tyrosine kinase activity, G$\alpha$q-coupled receptor ligands, e.g., ET-1, stimulate src-kinase activity which can then phosphorylate tyrosine residues and activate G$\alpha$q/11. In addition to certain 7TMRs, the insulin receptor can also phosphorylate G$\alpha$q/11 and can participate in a pathway of insulin signaling to glucose transport via cdc42 and PI3-kinase. Chronic ET-1 treatment has also been reported to induce desensitization of G$\alpha$q/11 function and promotes IRS-1 degradation, resulting in insulin resistance in vivo and in vitro. The present invention provides that GRK2 is one of the key molecules mediating ET-1-induced G$\alpha$q/11 desensitization and IRS-1 degradation.

Figure 6:
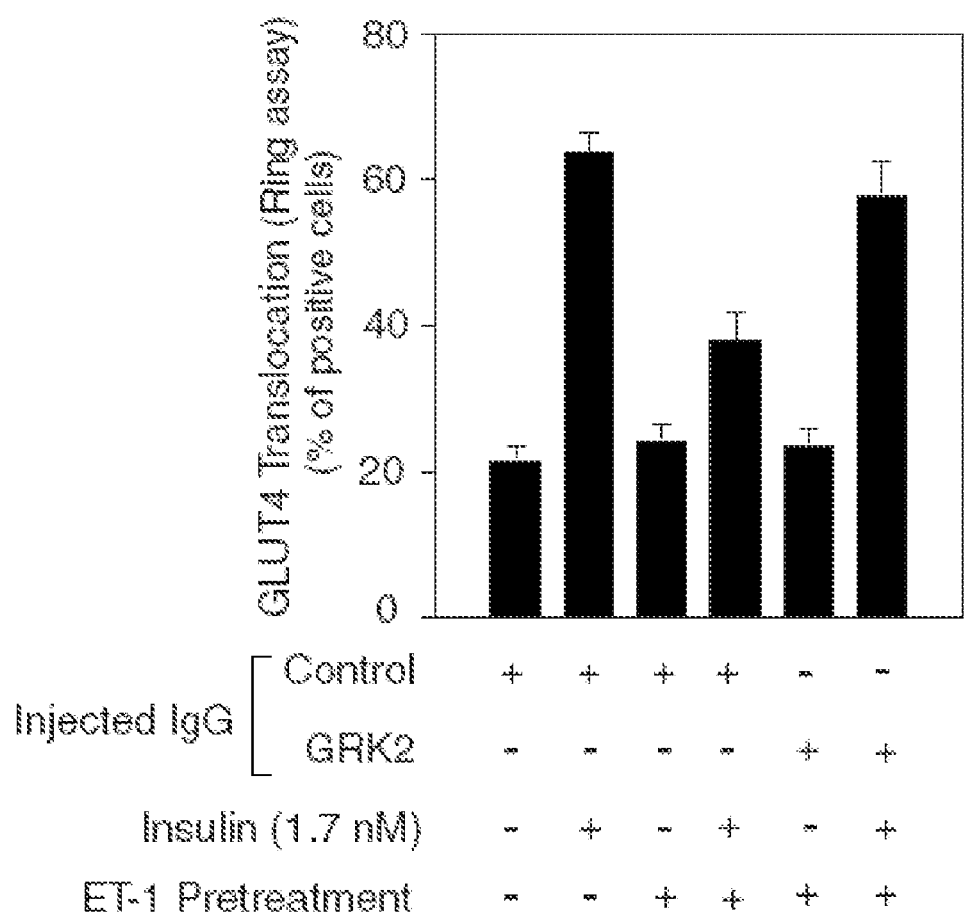
FIG. 6 depicts the effects of microinjection of anti-GRK2 antibody on GLUT4 translocation in 3T3-L1 adipocytes.
Figure 10:
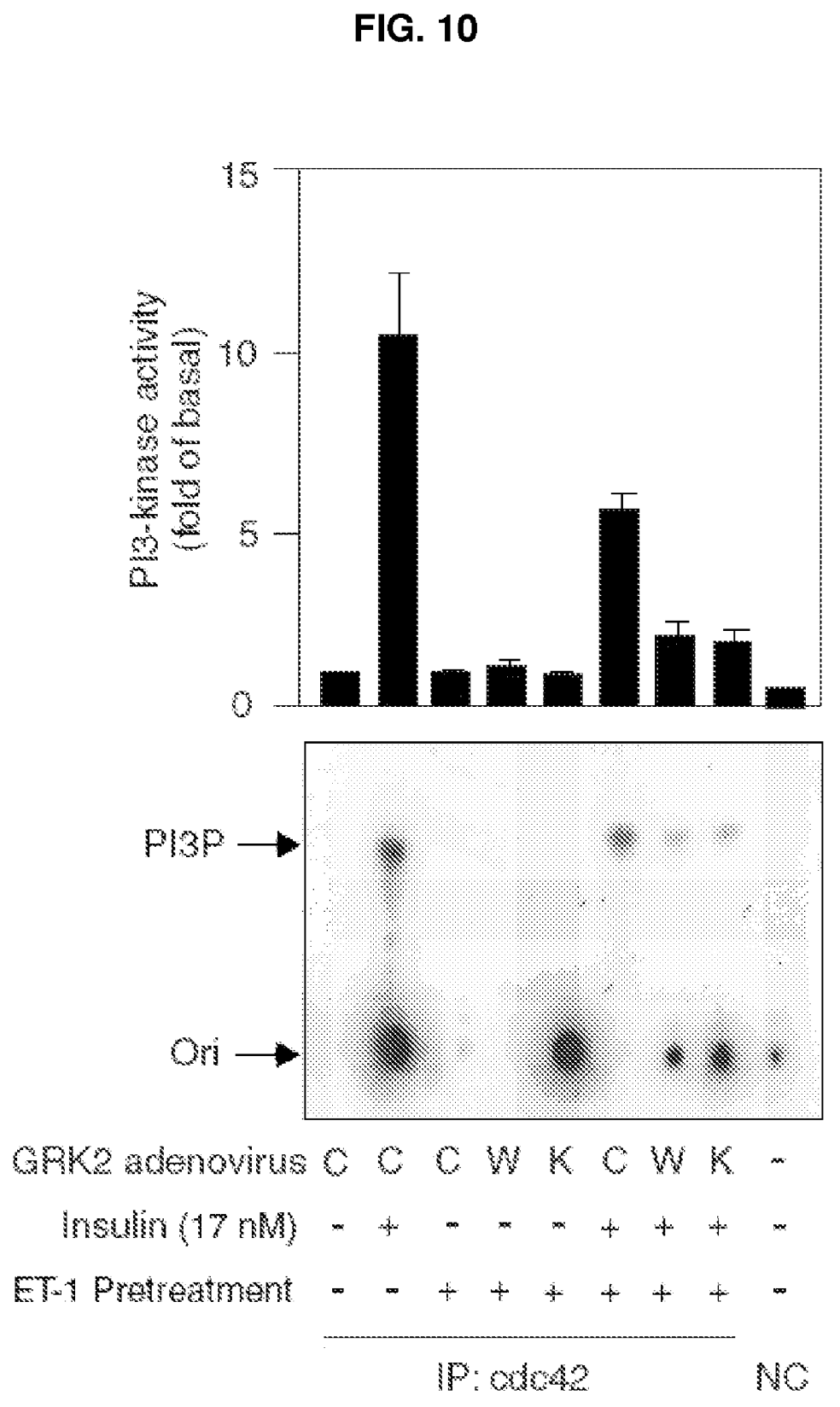
Figure 11:
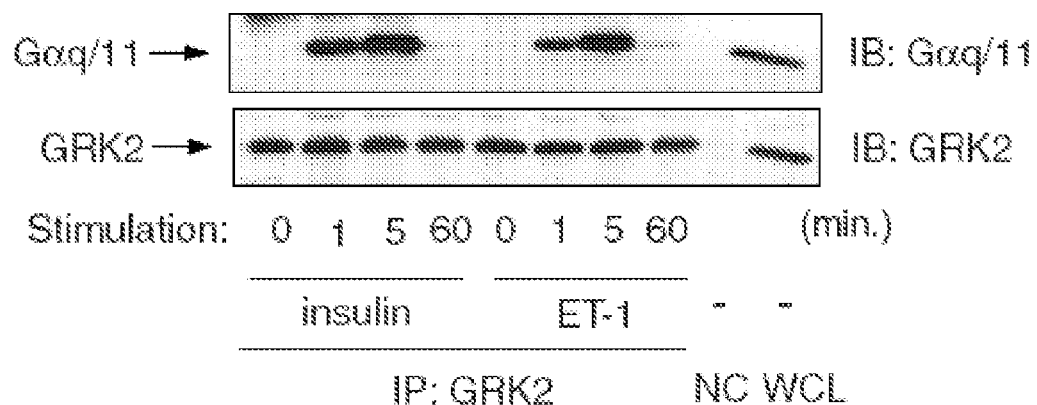
FIG. 11 is another depiction of the effects of wild type- or kinase deficient-GRK2 overexpression on Gαq/11-cdc42-PI3-kinase pathway in 3T3-L1 adipocytes.
Figure 11:
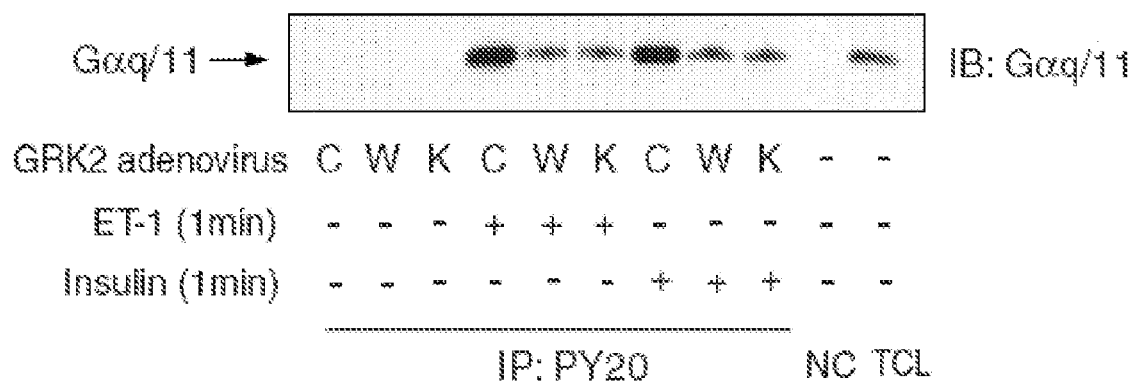

The present invention provides that inhibition of GRK2 rescued insulin signaling to GLUT4 translocation in the presence of chronic ET-1 treatment (FIG. 6). Both insulin and ET-1 enhanced the association of GRK2 with G$\alpha$q/11, and that chronic ET-1 treatment inhibited insulin activation of the G$\alpha$q/11 pathway, which was further inhibited by overexpression of either WT- or KD-GRK2 (FIGS. 10 and 11). This provides that the decreased activity of G$\alpha$q/11 and its downstream effectors is mediated by the association of G$\alpha$q/11 and GRK2. As previously discussed, the kinase activity of GRK2 is not required for its inhibitory effects on G$\alpha$q/11.

ET-1 stimulation increases the kinase activity of GRK2 leading to phosphorylation of the endothelin receptor type A receptor. Overexpression of KD-GRK2 clearly inhibited ET-1-induced IRS-1 degradation, whereas WT-GRK2 did not, providing that GRK2 kinase activity is involved in the mechanism. Among the numerous Ser/Thr phosphorylation sites in IRS-1, serines 307, 612, and 636 phosphorylation were stimulated by ET-1, and phosphorylation of serine 612/636 was dependent on the kinase activity of GRK2. The decreased expression and tyrosine phosphorylation of IRS-1 were associated with diminished downstream insulin action. Thus, with chronic ET-1 treatment, GRK2 is involved in decreasing the activity of both G$\alpha$q/11 and IRS-1, but by different mechanisms.

GRK2 is a serine/threonine kinase which, upon ET-1 stimulation, can associate with IRS-1 and promote ET-1-mediated IRS-1 serine phosphorylation and degradation. Several serine/threonine kinases can phosphorylate IRS proteins, including MAP kinase, PKC, JNK, mTOR, glycogen synthase kinase-3, and IKK, and certain IRS serine/threonine phosphorylation events are necessary for IRS degradation. Because these kinases do not operate simultaneously, it is possible that their role in IRS phosphorylation and degradation may vary across cell types, depending on which ligand is providing the stimulatory event.

Therefore, the present invention provides a novel role for GRK2 in chronic ET-1-induced cellular insulin resistance. In addition to inhibiting the G$\alpha$q/11 pathway, GRK2 kinase activity inhibits the IRS-1 pathway by enhancing degradation of IRS-1 after chronic ET-1 treatment. Therefore, those of skill in the art will recognize that GRK2 is a target for drug discovery and designing new treatments for metabolic syndrome, including insulin resistance diseases.

Accordingly, the invention provides a method for identifying a candidate insulin sensitizing compound, the method comprising: (a) contacting GRK2 or biologically-active fragment with a known compound that binds GRK2 to form an assay mixture, (b) contacting the assay mixture with a test compound, and (c) determining the ability of the test compound to interact with GRK2, wherein an increased ability of the test compound to interact with GRK2 in the presence of the known compound indicates that the test compound is an insulin sensitizing compound. In accordance with a further aspect of the invention, the known compound can be selected from the group consisting of G$\alpha$q/11, endothelin receptor type A and endothelin receptor type B.

The invention also provides a method for identifying a candidate insulin sensitizing compound, the method comprising: (a) contacting one of endothelin receptor type A or endothelin receptor type B, or biologically-active fragments thereof, with a known compound that binds endothelin receptor type A or endothelin receptor type B to form an assay mixture, (b) contacting the assay mixture with a test compound, and (c) determining the ability of the test compound to interact with one of endothelin receptor type A or endothelin receptor type B, wherein an increased ability of the test compound to interact with one of endothelin receptor type A or endothelin receptor type B in the presence of the known compound indicates that the test compound is an insulin sensitizing compound. In accordance with a further aspect of the invention, the known compound can be ET-1.

In addition, the invention provides a method for identifying a candidate insulin sensitizing compound, the method comprising: a) contacting a test compound with G$\alpha$q/11 and one of insulin receptor or GRK2; and b) detecting the level of phosphorylation of G$\alpha$q/11 in the presence of said test compound and one of insulin receptor or GRK2 as compared to the level of phosphorylation in the absence of said test compound, wherein a decreased level of phosphorylation in the presence of said test compound indicates that the test compound is an insulin sensitizing compound. In accordance with a further aspect of the invention, the compound can be a GRK2 RGS binding domain mimic, further wherein Gαq/11 phosphorylation is not inhibited.

The invention also provides a method for identifying a candidate insulin sensitizing compound, the method comprising: a) contacting a test compound with GRK2 and one of endothelin receptor type A or endothelin receptor type B; and b) detecting the level of phosphorylation of GRK2 in the presence of said test compound and one of endothelin receptor type A or endothelin receptor type B as compared to the level of phosphorylation in the absence of said test compound, wherein a decreased level of phosphorylation in the presence of said test compound indicates that the test compound is an insulin sensitizing compound.

The GRK2 polynucleotide, or gene, sequence for mouse (SEQ ID NO: 1; Accession No. BC053922) and polypeptide sequences for human (SEQ ID NOs: 2 and 3; Accession Nos. X69117 and CAA48870 respectively) are provided. SEQ ID NOs: 4 and 5 provide polynucleotide sequences encoding human G protein-q (Accession No. AF011496) and 11 α-subunit (Accession No. AF011497) respectively. Such sequences share 80 sequence identity and are collectively referred to as Gαq/11 herein. SEQ ID NOs: 6 and 7 provide polynucleotide sequences for endothelin receptor type A (Accession No. BC014472) and B (Accession No. NM_001957) respectively.

In one embodiment, an isolated GRK2 molecule can be used to express GRK2 (e.g., via a recombinant expression vector in a host cell in gene therapy applications), to detect GRK2 mRNA (e.g., in a biological sample) or to modulate a GRK2 activity. In addition, GRK2 polypeptides, e.g., SEQ ID NO: 3, can be used to screen drugs or compounds that modulate the GRK2 activity or expression as well as to treat disorders characterized by insufficient or excessive production (such as diabetes) of GRK2 or production of GRK2 forms that have decreased or aberrant activity compared to GRK2 wild-type protein, or modulate biological function that involve GRK2. In addition, the anti-GRK2 Abs of the invention can be used to detect and isolate GRK2 and modulate GRK2 activity.

Accordingly, the present invention provides a method for identifying a candidate insulin sensitization compound, i.e., candidate or test compounds or agents (e.g., peptides, peptidomimetics, small molecules or other drugs), and combinations thereof, that effect GRK2, a stimulatory or inhibitory effect, including translation, transcription, activity or copies of the gene in cells. In addition, the insulin sensitization compounds of the invention can include other candidate or test compounds or agents which are effective in modulating an activity of GRK2 either upstream, e.g., endothelin receptor type A and endothelin receptor type B, or downstream, e.g., Gαq/11. The present invention also includes compounds identified in screening assays provided herein.

Testing for compounds that increase or decrease GRK2 activity are desirable. A compound may modulate GRK2 activity by affecting: (1) the number of copies of the gene in the cell (amplifiers and deamplifiers); (2) increasing or decreasing transcription of the GRK2 (transcription up-regulators and down-regulators); (3) by increasing or decreasing the translation of GRK2 mRNA into protein (translation up-regulators and down-regulators); or (4) by increasing or decreasing the activity of GRK2 itself (agonists and antagonists).

To identify compounds that affect GRK2 at the DNA, RNA and protein levels, cells or organisms are contacted with a candidate compound and the corresponding change in GRK2 DNA, RNA or protein is assessed. For DNA amplifiers and deamplifiers, the amount of GRK2 DNA is measured, for those compounds that are transcription up-regulators and down-regulators the amount of GRK2 mRNA is determined; for translational up- and down-regulators, the amount of GRK2 polypeptides is measured. Compounds that are agonists or antagonists may be identified by contacting cells or organisms with the compound.

Modulators of GRK2 expression can be identified in a method where a cell is contacted with a candidate compound and the expression of GRK2 mRNA or protein in the cell is determined. The expression level of GRK2 mRNA or protein in the presence of the candidate compound is compared to GRK2 mRNA or protein levels in the absence of the candidate compound. The candidate compound can then be identified as a modulator of GRK2 mRNA or protein expression based upon this comparison. For example, when expression of GRK2 mRNA or protein is greater (i.e., statistically significant) in the presence of the candidate compound than in its absence, the candidate compound is identified as a stimulator of GRK2 mRNA or protein expression. Alternatively, when expression of GRK2 mRNA or protein is less (statistically significant) in the presence of the candidate compound than in its absence, the candidate compound is identified as an inhibitor of GRK2 mRNA or protein expression. The level of GRK2 mRNA or protein expression in the cells can be determined by methods described for detecting GRK2 mRNA or protein.

Methods of making recombinant cells and expressing cellular proteins such as GRK2 are well known in the art. For an introduction to recombinant methods, see, Berger and Kimmel, Guide to Molecular Cloning Techniques, Methods in Enzymology, volume 152, Academic Press, Inc., San Diego, Calif. ("Berger"); Sambrook et al. (1989) Molecular Cloning—A Laboratory Manual (2nd ed.) Vol. 1-3, Cold Spring Harbor Laboratory, Cold Spring Harbor Press, N.Y., ("Sambrook"); and Current Protocols in Molecular Biology, F. M. Ausubel et al., eds., Current Protocols, a joint venture between Greene Publishing Associates, Inc. and John Wiley & Sons, Inc., (e.g., current through 1999, e.g., at least through supplement 37) ("Ausubel"), each of which are incorporated herein by reference in its entirety. Culture of mammalian cell lines and cultured cells from tissue or blood samples is well known in the art. Freshney (Culture of Animal Cells, a Manual of Basic Technique, Third Edition, Wiley-Liss, New York (1994)) and the references cited therein provides a general guide to the culture of animal cells. Culture of plant cells is described in Payne et al. (1992) Plant Cell and Tissue Culture in Liquid Systems, John Wiley & Sons, Inc., New York, N.Y. Additional information on cell culture, including prokaryotic cell culture, is found in Berger, Sambrook, and Ausubel, supra. Cell culture media are described in Atlas and Parks (eds) The Handbook of Microbiological Media (1993) CRC Press, Boca Raton, Fla. Additional information is found in commercial literature such as the Life Science Research Cell Culture catalogue (various editions) from Sigma-Aldrich, Inc. (St. Louis, Mo.) and, e.g., the Plant Culture Catalogue and supplement (1997) also from Sigma-Aldrich, Inc. (St. Louis, Mo.).

Many other assays for screening candidate or test compounds that bind to or modulate the activity of GRK2 polynucleotide or polypeptide or biologically active portion are available to those of skill in the art. Test compounds can be obtained using any of the numerous approaches in combinatorial library methods, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptides, while the other four approaches encompass peptide, non-peptide oligomer or small molecule libraries of compounds.

Preparation and screening of combinatorial chemical libraries is well known to those of skill in the art. Such combinatorial chemical libraries include, but are not limited to, peptide libraries (see, e.g., U.S. Pat. No. 5,010,175, Furka, Int. J. Pept. Prot. Res. 37:487-493 (1991) and Houghton et al., Nature 354:84-88 (1991)). Other chemistries for generating chemical diversity libraries are also optionally used. Such chemistries include, but are not limited to: peptoids (PCT Publication No. WO 91/19735), encoded peptides (PCT Publication WO 93/20242), random bio-oligomers (PCT Publication No. WO 92/00091), benzodiazepines (U.S. Pat. No. 5,288,514), diversomers such as hydantoins, benzodiazepines and dipeptides (Hobbs et al., Proc. Nat. Acad. Sci. USA 90:6909-6913 (1993)), vinylogous polypeptides (Hagihara et al., J. Amer. Chem. Soc. 114:6568 (1992)), nonpeptidal peptidomimetics with $\alpha$-D-glucose scaffolding (Hirschmann et al., J. Amer. Chem. Soc. 114:9217-9218 (1992)), analogous organic syntheses of small compound libraries (Chen et al., J. Amer. Chem. Soc. 116:2661 (1994)), oligocarbamates (Cho et al., Science 261:1303 (1993)), and/or peptidyl phosphonates (Campbell et al., J. Org. Chem. 59:658 (1994)), nucleic acid libraries (see, Berger and Kimmel, Guide to Molecular Cloning Techniques, Methods in Enzymology, volume 152, Academic Press, Inc., San Diego, Calif. ("Berger"), Sambrook, supra, and Ausubel, supra; peptide nucleic acid libraries (see, e.g., U.S. Pat. No. 5,539,083), antibody libraries (see, e.g., Vaughn et al., Nature Biotechnology, 14(3):309-314 (1996) and PCT/US96/10287), carbohydrate libraries (see, e.g., Liang et al., Science, 274:1520-1522 (1996) and U.S. Pat. No. 5,593,853), small organic molecule libraries (see, e.g., benzodiazepines, Baum C&EN, Jan. 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

A "small molecule" refers to a composition that has a molecular weight of less than about 5 kD and more preferably less than about 4 kD, and most preferable less than 0.6 kD. Small molecules can be nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Cell-Free Assays

In one embodiment, a cell-free assay is provided which comprises contacting GRK2 or biologically-active fragment with a known compound that binds GRK2 to form an assay mixture, contacting the assay mixture with a test compound, and determining the ability of the test compound to interact with GRK2, where determining the ability of the test compound to interact with GRK2 comprises determining the ability of GRK2 to preferentially bind to or modulate the activity of a GRK2 target molecule.

The cell-free assays of the invention may be used with both soluble and membrane-bound forms of GRK2. In the case of cell-free assays comprising the membrane-bound form, a solubilizing agent to maintain GRK2 in solution. Examples of such solubilizing agents include non-ionic detergents such as n-octylglucoside, n-dodecylglucoside, n-dodecylmaltoside, octanoyl-N-methylglucamide, decanoyl-N-methylglucamide, TRITON® X-100 and others from the TRITON® series, THESIT®, Isotridecypoly(ethylene glycol ether),,, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

Immobilizing either GRK2 or its partner molecules can facilitate separation of complexed from uncomplexed forms of one or both of the proteins, as well as to accommodate high throughput assays. Binding of a test compound to GRK2, or interaction of GRK2 with a target molecule in the presence and absence of a candidate compound, can be accomplished in any vessel suitable for containing the reactants, such as microtiter plates, test tubes, and micro-centrifuge tubes. A fusion protein can be provided that provides a domain that allows one or both of the proteins to be bound to a matrix. Examples of such fusion proteins are provided in Table 3 below. For example, GST-GRK2 fusion proteins or GST-target fusion proteins can be adsorbed onto glutathione sepharose beads (SIGMA Chemical, St. Louis, Mo.) or glutathione derivatized microtiter plates that are then combined with the test compound or the test compound and either the non-adsorbed target protein or GRK2, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described. Alternatively, the complexes can be dissociated from the matrix, and the level of GRK2 binding or activity determined using standard techniques.

Other techniques for immobilizing proteins on matrices can also be used in screening assays. Either GRK2 or its target molecule can be immobilized using biotin-avidin or biotin-streptavidin systems. Biotinylation can be accomplished using many reagents, such as biotin-NHS (N-hydroxy-succinimide; PIERCE Chemicals, Rockford, Ill.), and immobilized in wells of streptavidin-coated 96 well plates (PIERCE Chemical). Alternatively, Abs reactive with GRK2 or target molecules, but which do not interfere with binding of the GRK2 to its target molecule, can be derivatized to the wells of the plate, and unbound target or GRK2 trapped in the wells by antibody conjugation. Methods for detecting such complexes, in addition to those described for the GST-immobilized complexes, include immunodetection of complexes using Abs reactive with GRK2 or its target, as well as enzyme-linked assays that rely on detecting an enzymatic activity associated with the GRK2 or target molecule.

Many other embodiments of such drug screening assays are available to those of skill in the art. For example, Sambrook and Ausubel provide multiple screening protocols which may be adapted for use with GRK2. In one such embodiment, a screen based on the essential function of GRK2 in the mammalian insulin signaling pathway can involve using the DNA sequence to which this transcription factor binds to generate a reporter construct that is activated upon activation of the GRK2 transcription factor, which occurs in response to, e.g., ET-1 stimulation. Such binding sites are known in the art and may be obtained in the following references, each of which is incorporated herein by reference in its entirety—Dhami G K, Babwah A V, Sterne-Marr R. Ferguson S S. Phosphorylation-independent regulation of metabotropic glutamate receptor 1 signaling requires G protein-coupled receptor kinase 2 binding to the second intracellular loop. J Biol Chem. 2005 May 3; Jewell-Motz E A, Small K M, Theiss C T, Liggett S B. alpha 2A/alpha 2C-adrenergic receptor third loop chimera show that agonist interaction with receptor subtype backbone establishes G protein-coupled receptor kinase phosphorylation. J Biol Chem. 2000 Sep 15; 275(37):28989-93; and *Tsuga* H, Kameyama K, Haga T, Honma T, Lameh J, Sadee W. Internalization and down-regulation of human muscarinic acetylcholine receptor m2 subtypes. Role of third intracellular m2 loop and G protein-coupled receptor kinase 2. J Biol Chem. 1998 Feb. 27; 273(9):5323-30.

The reporter construct could then be used in cell-based assays for drugs that would inhibit the induction of reporter gene activity in response to GRK2 stimulation. Such an assay would not only identify drugs that may specifically target and inhibit the GRK2 transcription factor, but would also identify drugs that would target and inhibit any essential molecule that functions upstream of GRK2 in the insulin signaling pathway.

In addition, any component of the insulin signaling pathway could be used in such a screen. For example, a critical regulatory kinase whose function is essential to the activation of the pathway (e.g., for activation of the GRK2 transcription factor) could also be used in homogenous (i.e., non-cell based) in vitro assays to identify drugs that effect this pathway.

Agonists and Antagonists

"Antagonist" includes any molecule that partially or fully blocks, inhibits, or neutralizes a biological activity of endogenous GRK2. Similarly, "agonist" includes any molecule that mimics a biological activity of endogenous GRK2. Molecules that can act as agonists or antagonists include Abs or Ab fragments, fragments or variants of endogenous GRK2, peptides, antisense oligonucleotides, small organic molecules, etc.

To assay for antagonists, GRK2 is added to, or expressed in, a cell along with the compound to be screened for a particular activity. If the compound inhibits the activity of interest in the presence of the GRK2, that compound is an antagonist to the GRK2; if GRK2 activity is enhanced, the compound is an agonist.

GRK2-expressing cells can be easily identified using any of the disclosed methods. For example, antibodies that recognize the amino- or carboxy-terminus of human GRK2 can be used to screen candidate cells by immunoprecipitation, Western blots, and immunohistochemical techniques. Likewise, SEQ ID NOs: 1 and 2 can be used to design primers and probes that can detect GRK2 mRNA in cells or samples from cells.

Any molecule that alters GRK2 cellular effects is a candidate antagonist or agonist. Screening techniques well known to those skilled in the art can identify these molecules. Examples of antagonists and agonists include: (1) small organic and inorganic compounds, (2) small peptides, (3) Abs and derivatives, (4) polypeptides closely related to GRK2, (5) antisense DNA and RNA, (6) ribozymes, (7) triple DNA helices, (8) siRNAs and (9) nucleic acid aptamers.

Small molecules that bind to the GRK2 active site or other relevant part of the polypeptide and inhibit the biological activity of the GRK2 are antagonists. Examples of small molecule antagonists include small peptides, peptide-like molecules, preferably soluble, and synthetic non-peptidyl organic or inorganic compounds. These same molecules, if they enhance GRK2 activity, are examples of agonists.

Almost any antibody that affects GRK2s function is a candidate antagonist, and occasionally, agonist. Examples of antibody antagonists include polyclonal, monoclonal, single-chain, anti-idiotypic, chimeric Abs, or humanized versions of such Abs or fragments. Abs may be from any species in which an immune response can be raised. Humanized Abs are also contemplated.

Alternatively, a potential antagonist or agonist may be a closely related protein, for example, a mutated form of the GRK2 that recognizes a GRK2-interacting protein but imparts no effect, thereby competitively inhibiting GRK2 action. Alternatively, a mutated GRK2 may be constitutively activated and may act as an agonist.

GRK2 Polynucleotides

In various embodiments of the present invention, the methods for identifying modulatory compounds can comprise the utilization of a GRK2 polynucleotide. One aspect of the invention pertains to using isolated polynucleotides that encode GRK2 or biologically-active portions thereof, as well as fragments sufficient for use as hybridization probes to identify GRK2-encoding nucleic acids (e.g., GRK2 mRNAs) and fragments for use as polymerase chain reaction (PCR) primers for the amplification and/or mutation of GRK2 molecules. A "nucleic acid molecule" or polynucleotide includes DNA molecules (e.g., cDNA or genomic DNA), RNA molecules (e.g., mRNA), analogs of the DNA or RNA generated using nucleotide analogs, and derivatives, fragments and homologues. The nucleic acid molecule may be single-stranded or double-stranded, but preferably comprises double-stranded DNA.

Probes

Probes are nucleic acid sequences of variable length, preferably between at least about 10 nucleotides (nt), 100 nt, or many (e.g., 6,000 nt) depending on the specific use. Probes are used to detect identical, similar, or complementary nucleic acid sequences. Longer length probes can be obtained from a natural or recombinant source, are highly specific, and much slower to hybridize than shorter-length oligomer probes. Probes may be single- or double-stranded and designed to have specificity in PCR, membrane-based hybridization technologies, or ELISA-like technologies. Probes are substantially purified oligonucleotides that will hybridize under stringent conditions to at least optimally 12, 25, 50, 100, 150, 200, 250, 300, 350 or 400 consecutive sense strand nucleotide sequence of SEQ ID NOs: 1 and 2; or an anti-sense strand nucleotide sequence of SEQ ID NOs: 1 and 2 and 10; or of a naturally occurring mutant of SEQ ID NOs: 1 and 2.

The full—or partial-length native sequence GRK2 may be used to "pull out" similar (homologous) sequences, such as: (1) full-length or fragments of GRK2 cDNA from a cDNA library from any species (e.g., human, murine, feline, canine, bacterial, viral, retroviral, yeast), (2) from cells or tissues, (3) variants within a species, and (4) homologues and variants from other species. See, Ausubel and Sambrook, supra. To find related sequences that may encode related genes, the probe may be designed to encode unique sequences or degenerate sequences. Sequences may also be genomic sequences including promoters, enhancer elements and introns of native sequence GRK2.

For example, GRK2 coding region in another species may be isolated using such probes. A probe of about 40 bases is designed, based on GRK2, and made. To detect hybridizations, probes are labeled using, for example, radionuclides such as $^{32}P$ or $^{35}S$, or enzymatic labels such as alkaline phosphatase coupled to the probe via avidin-biotin systems. Labeled probes are used to detect nucleic acids having a complementary sequence to that of GRK2 in libraries of cDNA, genomic DNA or mRNA of a desired species.

Such probes can be used as a part of a diagnostic test kit for identifying cells or tissues which misexpress a GRK2, such as by measuring a level of a GRK2 in a sample of cells from a subject e.g., detecting GRK2 mRNA levels or determining whether a genomic GRK2 has been mutated or deleted.

Isolated Nucleic Acids

An isolated nucleic acid molecule or polynucleotide is separated from other nucleic acid molecules that are present in the natural source of the nucleic acid. Preferably, an isolated nucleic acid is free of sequences that naturally flank the nucleic acid (i.e., sequences located at the 5'- and 3'-termini of the nucleic acid) in the genomic DNA of the organism from which the nucleic acid is derived. For example, in various embodiments, isolated GRK2 molecules can contain less than about 5 kb, 4 kb, 3 kb, 2 kb, 1 kb, 0.5 kb or 0.1 kb of nucleotide sequences which naturally flank the nucleic acid molecule in genomic DNA of the cell/tissue from which the nucleic acid is derived (e.g., brain, heart, liver, spleen, etc.). Moreover, an isolated nucleic acid molecule, such as a cDNA molecule, can be substantially free of other cellular material or culture medium when produced by recombinant techniques, or of chemical precursors or other chemicals when chemically synthesized.

A nucleic acid molecule of the invention, e.g., a nucleic acid molecule having a nucleotide sequence of SEQ ID NOs: 1 or 2, or a complement thereof, can be isolated using standard molecular biology techniques and the provided sequence information. Using all or a portion of the nucleic acid sequence of SEQ ID NOs: 1 or 2 as a hybridization probe, GRK2 molecules can be isolated using standard hybridization and cloning techniques. See, Ausubel and Sambrook, supra.

PCR amplification techniques can be used to amplify GRK2 using cDNA, mRNA or alternatively, genomic DNA, as a template and appropriate oligonucleotide primers. Such nucleic acids can be cloned into an appropriate vector and characterized by DNA sequence analysis. Furthermore, oligonucleotides corresponding to GRK2 sequences can be prepared by standard synthetic techniques, e.g., an automated DNA synthesizer.

Oligonucleotides

An oligonucleotide comprises a series of linked nucleotide residues, which oligonucleotide has a sufficient number of nucleotide bases to be used in a PCR reaction or other application. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides comprise portions of a nucleic acid sequence having about 10 nt, 50 nt, or 100 ht in length, preferably about 15 nt to 30 nt in length. In one embodiment of the invention, an oligonucleotide comprising a nucleic acid molecule less than 100 nt in length would further comprise at least 6 contiguous nucleotides of SEQ ID NOs: 1 or 2, or a complement thereof. Oligonucleotides may be chemically synthesized and may also be used as probes.

Complementary Nucleic Acid Sequences and Binding

In another embodiment, an isolated nucleic acid molecule that can be used in the invention comprises a nucleic acid molecule that is a complement of the nucleotide sequence shown in SEQ ID NOs: 1 or 2, or a portion of one of the nucleotide sequences (e.g., a fragment that can be used as a probe or primer or a fragment encoding a biologically-active portion of a GRK2). A nucleic acid molecule that is complementary to the nucleotide sequence shown in SEQ ID NOs: 1 or 2, is one that is sufficiently complementary to the nucleotide sequence shown in SEQ ID NOs: 1 or 2, that it can hydrogen bond with little or no mismatches to the nucleotide sequence shown in SEQ ID NOs: 1 or 2, thereby forming a stable duplex.

"Complementary" refers to Watson-Crick or Hoogsteen base pairing between nucleotides units of a nucleic acid molecule, and the term "binding" means the physical or chemical interaction between two polypeptides or compounds or associated polypeptides or compounds or combinations thereof. Binding includes ionic, non-ionic, van der Waals, hydrophobic interactions, and the like. A physical interaction can be either direct or indirect. Indirect interactions may be through or due to the effects of another polypeptide or compound. Direct binding refers to interactions that do not take place through, or due to, the effect of another polypeptide or compound, but instead are without other substantial chemical intermediates.

Nucleic acid fragments are at least 6 (contiguous) nucleic acids or at least 4 (contiguous) amino acids, a length sufficient to allow for specific hybridization in the case of nucleic acids or for specific recognition of an epitope in the case of amino acids, respectively, and are at most some portion less than a full-length sequence. Fragments may be derived from any contiguous portion of a nucleic acid or amino acid sequence of choice.

Derivatives and Analogs

Derivatives are nucleic acid sequences or amino acid sequences formed from the native compounds either directly or by modification or partial substitution. Analogs are nucleic acid sequences or amino acid sequences that have a structure similar to, but not identical to, the native compound but differ from it in respect to certain components or side chains. Analogs may be synthetic or from a different evolutionary origin and may have a similar or opposite metabolic activity compared to wild type. Homologues are nucleic acid sequences or amino acid sequences of a particular gene that are derived from different species.

Derivatives and analogs may be full length or other than full length, if the derivative or analog contains a modified nucleic acid or amino acid, as described below. Derivatives or analogs of the nucleic acids or proteins of the invention include, but are not limited to, molecules comprising regions that are substantially homologous to the nucleic acids or proteins of the invention, in various embodiments, by at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99%, over a nucleic acid or amino acid sequence of identical size or when compared to an aligned sequence in which the alignment is done by a computer homology program known in the art, e.g., BLAST, or whose encoding nucleic acid is capable of hybridizing to the complement of a sequence encoding the aforementioned proteins under stringent, moderately stringent, or low stringent conditions. See, Ausubel, supra.

Homology

A "homologous nucleic acid sequence" or "homologous amino acid sequence," or variations thereof, refer to sequences characterized by a homology at the nucleotide level or amino acid level as discussed above. Homologous nucleotide sequences encode those sequences coding for isoforms of GRK2. Isoforms can be expressed in different tissues of the same organism as a result of, for example, alternative splicing of RNA. Alternatively, different genes can encode isoforms. In the invention, homologous nucleotide sequences include nucleotide sequences encoding for a GRK2 of species other than humans, including, but not limited to: vertebrates, and thus can include, e.g., frog, mouse, rat, rabbit, dog, cat, cow, horse, and other organisms. Homologous nucleotide sequences also include, but are not limited to, naturally occurring allelic variations and mutations of the nucleotide sequences set forth herein. A homologous nucleotide sequence does not, however, include the exact nucleotide sequence encoding human GRK2, e.g., SEQ ID NO: 3. Homologous nucleic acid sequences include those nucleic acid sequences that encode conservative amino acid substitutions in SEQ ID NO: 3, as well as a polypeptide possessing GRK2 biological activity.

Open Reading Frames

The open reading frame (ORF) of a GRK2 gene encodes GRK2. An ORF is a nucleotide sequence that has a start codon (ATG) and terminates with one of the three "stop" codons (TAA, TAG, or TGA). In this invention, however, an ORF may be any part of a coding sequence that may or may not comprise a start codon and a stop codon. To achieve a unique sequence, preferable GRK2 ORFs encode at least 50 amino acids.

GRK2 Hybridization

Homologues (i.e., nucleic acids encoding GRK2 derived from species other than human) or other related sequences (e.g., paralogs) can be obtained by low, moderate or high stringency hybridization with all or a portion of the particular human sequence as a probe using methods well known in the art for nucleic acid hybridization and cloning.

The specificity of single stranded DNA to hybridize complementary fragments is determined by the "stringency" of the reaction conditions. Hybridization stringency increases as the propensity to form DNA duplexes decreases. In nucleic acid hybridization reactions, the stringency can be chosen to either favor specific hybridizations (high stringency), which can be used to identify, for example, full-length clones from a library. Less-specific hybridizations (low stringency) can be used to identify related, but not exact, DNA molecules (homologous, but not identical) or segments.

DNA duplexes are stabilized by: (1) the number of complementary base pairs, (2) the type of base pairs, (3) salt concentration (ionic strength) of the reaction mixture, (4) the temperature of the reaction, and (5) the presence of certain organic solvents, such as formamide which decreases DNA duplex stability. In general, the longer the probe, the higher the temperature required for proper annealing. A common approach is to vary the temperature: higher relative temperatures result in more stringent reaction conditions. See, Ausubel, supra.

To hybridize under "stringent conditions" describes hybridization protocols in which nucleotide sequences at least 60% homologous to each other remain hybridized. Generally, stringent conditions are selected to be about 5° C. lower than the thermal melting point (Tm) for the specific sequence at a defined ionic strength and pH. The Tm is the temperature (under defined ionic strength, pH and nucleic acid concentration) at which 50% of the probes complementary to the target sequence hybridize to the target sequence at equilibrium. Since the target sequences are generally present at excess, at Tm, 50% of the probes are occupied at equilibrium.

"Stringent hybridization conditions" conditions enable a probe, primer or oligonucleotide to hybridize only to its target sequence. Stringent conditions are sequence-dependent and will differ. Stringent conditions comprise: (1) low ionic strength and high temperature washes (e.g., 15 mM sodium chloride, 1.5 mM sodium citrate, 0.1% sodium dodecyl sulfate at 50° C.); (2) a denaturing agent during hybridization (e.g., 50% (v/v) formamide, 0.1% bovine serum albumin, 0.1% Ficoll, 0.1% polyvinylpyrrolidone, 50 mM sodium phosphate buffer (pH 6.5; 750 mM sodium chloride, 75 mM sodium citrate at 42° C.); or (3) 50% formamide. Washes typically also comprise 5×SSC (0.75 M NaCl, 75 mM sodium citrate), 50 mM sodium phosphate (pH 6.8), 0.1% sodium pyrophosphate, 5×Denhardt's solution, sonicated salmon sperm DNA (50 µg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. Preferably, the conditions are such that sequences at least about 65%, 70%, 75%, 85%, 90%, 95%, 98%, or 99% homologous to each other typically remain hybridized to each other. These conditions are presented as examples and are not meant to be limiting.

"Moderately stringent conditions" use washing solutions and hybridization conditions that are less stringent, such that a polynucleotide will hybridize to the entire, fragments, derivatives or analogs of SEQ ID NOs: 1 or 2. See Sambrook, supra. One example comprises hybridization in 6×SSC, 5×Denhardt's solution, 0.5% SDS and 100 mg/ml denatured salmon sperm DNA at 55° C., followed by one or more washes in 1×SSC, 0.1% SDS at 37° C. The temperature, ionic strength, etc., can be adjusted to accommodate experimental factors such as probe length. Other moderate stringency conditions are described in Sambrook, supra.

"Low stringent conditions" use washing solutions and hybridization conditions that are less stringent than those for moderate stringency, such that a polynucleotide will hybridize to the entire, fragments, derivatives or analogs of SEQ ID NOs: 1 or 2. See Sambrook, supra. A non-limiting example of low stringency hybridization conditions are hybridization in 35% formamide, 5×SSC, 50 mM Tris-HCl (pH 7.5), 5 mM EDTA, 0.02% PVP, 0.02% Ficoll, 0.2% BSA, 100 mg/ml denatured salmon sperm DNA, 10% (wt/vol) dextran sulfate at 40° C., followed by one or more washes in 2×SSC, 25 mM Tris-HCl (pH 7.4), 5 mM EDTA, and 0.1% SDS at 50° C. Other conditions of low stringency, such as those for cross-species hybridizations are described in Ausubel, supra.

GRK2 Nucleic Acid Variants

The invention further encompasses using nucleic acid molecules that differ from the nucleotide sequences shown in SEQ ID NOs: 1 or 2 due to degeneracy of the genetic code and thus encode the same GRK2 as that encoded by the nucleotide sequences shown in SEQ ID NOs: 1 or 2. An isolated nucleic acid molecule of the invention has a nucleotide sequence encoding a protein having an amino acid sequence shown in SEQ ID NO: 3.

Moreover, GRK2 from other species that have a nucleotide sequence that differs from the sequence of SEQ ID NOs: 1 or 2, are contemplated. Nucleic acid molecules corresponding to natural allelic variants and homologues of the GRK2 cDNAs of the invention can be isolated based on their homology to the GRK2 of SEQ ID NOs: 1 or 2 using cDNA-derived probes to hybridize to homologous GRK2 sequences under stringent conditions.

"GRK2 variant polynucleotide" or "GRK2 variant nucleic acid sequence" means a nucleic acid molecule which encodes an active GRK2 that (1) has at least about 80% nucleic acid sequence identity with a nucleotide acid sequence encoding a full-length native GRK2, (2) a full-length native GRK2 lacking the signal peptide, (3) an extracellular domain of a GRK2, with or without the signal peptide, or (4) any other fragment of a full-length GRK2. Ordinarily, a GRK2 variant polynucleotide will have at least about 80%, 81%, 82%, 83%, 84%, 85%, 86%, 87%, 88%, 89%, 90%, 91%, 92%, 93%, 94%, 95%, 96%, 97%, 98% or 99% nucleic acid sequence identity and yet more preferably at least about 99% nucleic acid sequence identity with the nucleic acid sequence encoding a full-length native GRK2. A GRK2 variant polynucleotide may encode full-length native GRK2 lacking the signal peptide, an extracellular domain of a GRK2, with or without the signal sequence, or any other fragment of a full-length GRK2. Variants do not encompass the native nucleotide sequence.

Ordinarily, GRK2 variant polynucleotides are at least about 30 nucleotides in length, often at least about 60, 90, 120, 150, 180, 210, 240, 270, 300, 450, 600 nucleotides in length, more often at least about 900 nucleotides in length, or more.

"Percent (%) nucleic acid sequence identity" with respect to GRK2-encoding nucleic acid sequences identified herein is defined as the percentage of nucleotides in a candidate sequence that are identical with the nucleotides in the GRK2 sequence of interest, after aligning the sequences and introducing gaps, if necessary, to achieve the maximum percent sequence identity. Alignment for purposes of determining % nucleic acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for measuring alignment, including any algorithms needed to achieve maximal alignment over the full length of the sequences being compared.

When nucleotide sequences are aligned, the % nucleic acid sequence identity of a given nucleic acid sequence C to, with, or against a given nucleic acid sequence D (which can alternatively be phrased as a given nucleic acid sequence C that has or comprises a certain % nucleic acid sequence identity to, with, or against a given nucleic acid sequence D) can be calculated as follows:

$$\% \text{ nucleic acid sequence identity} = W/Z \cdot 100$$

where W is the number of nucleotides cored as identical matches by the sequence alignment program's or algorithm's alignment of C and D and Z is the total number of nucleotides in D.

When the length of nucleic acid sequence C is not equal to the length of nucleic acid sequence D, the % nucleic acid sequence identity of C to D will not equal the % nucleic acid sequence identity of D to C.

In addition to naturally-occurring allelic variants of GRK2, changes can be introduced by mutation into SEQ ID NOs: 1 or 2 that incur alterations in the amino acid sequences of the encoded GRK2 that do not alter GRK2 function. For example, nucleotide substitutions leading to amino acid substitutions at "non-essential" amino acid residues can be made in the sequence of SEQ ID NO: 3. A "non-essential" amino acid residue is a residue that can be altered from the wild-type sequences of the GRK2 without altering their biological activity, whereas an "essential" amino acid residue is required for such biological activity. For example, amino acid residues that are conserved among the GRK2 of the invention are predicted to be particularly non-amenable to alteration. Amino acids for which conservative substitutions can be made are well known in the art.

Useful conservative substitutions are shown in Table 1. Conservative substitutions whereby an amino acid of one class is replaced with another amino acid of the same type fall within the scope of the subject invention so long as the substitution does not materially alter the biological activity of the compound. The invention can use mutant or variant GRK2, any of which bases may be changed from the corresponding base shown in Table 2 while still encoding a polypeptide that maintains the activities and physiological functions of the GRK2 fragment, or a fragment of such a nucleic acid. If such substitutions result in a change in biological activity, then more substantial changes, indicated in Table 2 as examples are introduced and the products screened for GRK2 polypeptide biological activity.

TABLE 1

Preferred Amino Acid Substitutions

| Original residue | Exemplary substitutions | Preferred substitutions |
|---|---|---|
| Ala (A) | Val, Leu, Ile | Val |
| Arg (R) | Lys, Gln, Asn | Lys |
| Asn (N) | Gln, His, Lys, Arg | Gln |
| Asp (D) | Glu | Glu |
| Cys (C) | Ser | Ser |
| Gln (Q) | Asn | Asn |
| Glu (E) | Asp | Asp |
| Gly (G) | Pro, Ala | Ala |
| His (H) | Asn, Gln, Lys, Arg | Arg |
| Ile (I) | Leu, Val, Met, Ala, Phe, Norleucine | Leu |
| Leu (L) | Norleucine, Ile, Val, Met, Ala, Phe | Ile |
| Lys (K) | Arg, Gln, Asn | Arg |
| Met (M) | Leu, Phe, Ile | Leu |
| Phe (F) | Leu, Val, Ile, Ala, Tyr | Leu |
| Pro (P) | Ala | Ala |
| Ser (S) | Thr | Thr |
| Thr (T) | Ser | Ser |
| Trp (W) | Tyr, Phe | Tyr |
| Tyr (Y) | Trp, Phe, Thr, Ser | Phe |
| Val (V) | Ile, Leu, Met, Phe, Ala, Norleucine | Leu |

\*\*\*\* Non-conservative substitutions that affect (1) the structure of the polypeptide backbone, such as a β-sheet or α-helical conformation, (2) the charge or (3) hydrophobicity, or (4) the bulk of the side chain of the target site can modify GRK2 polypeptide function or immunological identity.Residues are divided into groups based on common side-chain properties as denoted in Table 2. Non-conservative substitutions entail exchanging a member of one of these classes for another class. Substitutions may be introduced into conservative substitution sites or more preferably into non-conserved sites.

TABLE 2

Amino acid classes

| Class | Amino acids |
|---|---|
| hydrophobic | Norleucine, Met, Ala, Val, Leu, Ile |
| neutral hydrophilic | Cys, Ser, Thr |
| acidic | Asp, Glu |
| basic | Asn, Gln, His, Lys, Arg |
| disrupt chain conformation | Gly, Pro |
| aromatic | Trp, Tyr, Phe |

The variant polypeptides can be made using methods known in the art such as oligonucleotide-mediated (site-directed) mutagenesis, alanine scanning, and PCR mutagenesis. Site-directed mutagenesis, cassette mutagenesis, restriction selection mutagenesis or other known techniques can be performed on the cloned DNA to produce the GRK2 variant DNA. See, e.g., Ausubel and Sambrook, supra.

In one embodiment, the isolated nucleic acid molecule comprises a nucleotide sequence encoding a protein, wherein the protein comprises an amino acid sequence at least about 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% homologous to SEQ ID NO: 3.

GRK2 Polypeptides

In yet another aspect of the present invention, the cells can comprise a GRK2 variant or fragment protein. A GRK2 polypeptide includes the amino acid sequence of GRK2 whose sequences are provided in SEQ ID NO: 3. The invention also includes a mutant or variant protein any of whose residues may be changed from the corresponding residues shown in SEQ ID NOs: 3, while still encoding a protein that maintains its GRK2 activities and physiological functions, or a functional fragment thereof.

In general, an GRK2 polypeptide variant preserves GRK2-like function and includes any variant in which residues at a particular position in the sequence have been substituted by other amino acids, and further includes the possibility of inserting an additional residue or residues between two residues of the parent protein as well as the possibility of deleting one or more residues from the parent sequence. Any amino acid substitution, insertion, or deletion is encompassed by the invention. In favorable circumstances, the substitution is a conservative substitution as defined above.

An active GRK2 polypeptide or GRK2 polypeptide fragment retains a biological and/or an immunological activity similar, but not necessarily identical, to an activity of a naturally-occurring (wild-type) GRK2 polypeptide of the invention, including mature forms. A particular biological assay, with or without dose dependency, can be used to determine GRK2 activity. A nucleic acid fragment encoding a biologically-active portion of GRK2 can be prepared by isolating a portion of SEQ ID NOs: 1 or 2 that encodes a polypeptide having a GRK2 biological activity (the biological activities of the GRK2 are described below), expressing the encoded portion of GRK2 (e.g., by recombinant expression in vitro) and assessing the activity of the encoded portion of GRK2. Immunological activity refers to the ability to induce the production of an antibody against an antigenic epitope possessed by a native GRK2; biological activity refers to a function, either inhibitory or stimulatory, caused by a native GRK2 that excludes immunological activity.

"GRK2 polypeptide variant" means an active GRK2 polypeptide having at least: (1) about 80% amino acid sequence identity with a full-length native sequence GRK2 polypeptide sequence, (2) a GRK2 polypeptide sequence lacking the signal peptide, (3) an extracellular domain of a GRK2 polypeptide, with or without the signal peptide, or (4) any other fragment of a full-length GRK2 polypeptide sequence. For example, GRK2 polypeptide variants include GRK2 polypeptides wherein one or more amino acid residues are added or deleted at the N- or C-terminus of the full-length native amino acid sequence. A GRK2 polypeptide variant will have at least about 80% amino acid sequence identity, preferably at least about 81% amino acid sequence identity, more preferably at least about 82%, 83%, 84%, 85%, 86%, 87%, 88%, 89%, 90%, 91%, 92%, 93%, 94%, 95%, 96%, 97%, 98% or 99% amino acid sequence identity with a full-length native sequence GRK2 polypeptide sequence. A GRK2 polypeptide variant may have a sequence lacking the signal peptide, an extracellular domain of a GRK2 polypeptide, with or without the signal peptide, or any other fragment of a full-length GRK2 polypeptide sequence. Ordinarily, GRK2 variant polypeptides are at least about 10 amino acids in length, often at least about 20 amino acids in length, more often at least about 30, 40, 50, 60, 70, 80, 90, 100, 150, 200, or 300 amino acids in length, or more.

"Percent (%) amino acid sequence identity" is defined as the percentage of amino acid residues that are identical with amino acid residues in the disclosed GRK2 polypeptide sequence in a candidate sequence when the two sequences are aligned. To determine % amino acid identity, sequences are aligned and if necessary, gaps are introduced to achieve the maximum % sequence identity; conservative substitutions are not considered as part of the sequence identity. Amino acid sequence alignment procedures to determine percent identity are well known to those of skill in the art. Often publicly available computer software such as BLAST, BLAST2, ALIGN2 or Megalign (DNASTAR) software is used to align peptide sequences. Those skilled in the art can determine appropriate parameters for measuring alignment, including any algorithms needed to achieve maximal alignment over the full length of the sequences being compared.

When amino acid sequences are aligned, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) can be calculated as:

$$\text{\% amino acid sequence identity} = X/Y \cdot 100$$

where X is the number of amino acid residues scored as identical matches by the sequence alignment program's or algorithm's alignment of A and B and Y is the total number of amino acid residues in B.

If the length of amino acid sequence A is not equal to the length of amino acid sequence B, the % amino acid sequence identity of A to B will not equal the % amino acid sequence identity of B to A.

Biologically active portions of GRK2 include peptides comprising amino acid sequences sufficiently homologous to or derived from the amino acid sequences of the GRK2 (SEQ ID NO: 3) that include fewer amino acids than the full-length GRK2, and exhibit at least one activity of a GRK2. Biologically active portions comprise a domain or motif with at least one activity of native GRK2. A biologically active portion of a GRK2 can be a polypeptide that is, for example, 10, 25, 50, 100 or more amino acid residues in length. Other biologically active portions, in which other regions of the protein are deleted, can be prepared by recombinant techniques and evaluated for one or more of the functional activities of a native GRK2.

Biologically active portions of GRK2 may have an amino acid sequence shown in SEQ ID NO: 3, or substantially homologous to SEQ ID NO: 3, and retains the functional activity of the protein of SEQ ID NO: 3, yet differs in amino acid sequence due to natural allelic variation or mutagenesis. Other biologically active GRK2 may comprise an amino acid sequence at least about 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% homologous to the amino acid sequence of SEQ ID NO: 3, and retains the functional activity of native GRK2.

Fusion polypeptides are useful in expression studies, cell-localization, bioassays, and GRK2 purification. A GRK2 "chimeric protein" or "fusion protein" comprises GRK2 fused to a non-GRK2 polypeptide. A non-GRK2 polypeptide is not substantially homologous to GRK2 (SEQ ID NO: 3). A GRK2 fusion protein may include any portion to the entire GRK2, including any number of the biologically active portions. GRK2 may be fused to the C-terminus of the GST (glutathione S-transferase) sequences. Such fusion proteins facilitate the purification of recombinant GRK2. In certain host cells, (e.g., mammalian), heterologous signal sequences fusions may ameliorate GRK2 expression and/or secretion. Additional exemplary fusions are presented in Table 3.

Other fusion partners can adapt GRK2 therapeutically. Fusions with members of the immunoglobulin (Ig) protein family are useful in therapies that inhibit GRK2 ligand or substrate interactions, consequently suppressing GRK2-mediated signal transduction in vivo. GRK2-1 g fusion polypeptides can also be used as immunogens to produce anti-GRK2 Abs in a subject, to purify GRK2 ligands, and to screen for molecules that inhibit interactions of GRK2 with other molecules.

Fusion proteins can be easily created using recombinant methods. A nucleic acid encoding GRK2 can be fused in-frame with a non-GRK2 encoding nucleic acid, to the GRK2 NH2- or COO-terminus, or internally. Fusion genes may also be synthesized by conventional techniques, including automated DNA synthesizers. PCR amplification using anchor primers that give rise to complementary overhangs between two consecutive gene fragments that can subsequently be annealed and reamplified to generate a chimeric gene sequence is also useful. See Ausubel, supra. Many vectors are commercially available that facilitate sub-cloning GRK2 in-frame to a fusion moiety.

invention, a GRK2 protein crystal can be soaked in a solution containing a chemical compound of the present invention. Binding of the chemical compound to the crystal is then determined by methods standard in the art.

One aspect of the present invention is a therapeutic composition. A therapeutic composition of the present invention comprises one or more therapeutic compounds. In one aspect, a therapeutic composition is provided that is capable of inhibiting GRK2 stimulation that involves a GRK2 protein. For example, a therapeutic composition of the present invention can inhibit (i.e., prevent, block) binding of an GRK2 protein on a cell to a molecule by interfering with the, e.g., DNA binding site of the GRK2 protein. As used herein, the term "binding site" refers to the region of a GRK2 protein to which a ligand or substrate specifically binds. In one aspect of the present invention, a method is provided for inhibiting, e.g., insulin resistance, in a subject comprising administering to the subject in need thereof a therapeutically effective amount of a therapeutic composition of the present invention.

Suitable inhibitory compounds of the present invention are compounds that interact directly with an GRK2 protein

TABLE 3

Useful non-GRK2 fusion polypeptides

| Reporter | in vitro | in vivo | Notes |
|---|---|---|---|
| Human growth hormone (hGH) | Radioimmuno-assay | none | Expensive, insensitive, narrow linear range. |
| β-glucuronidase (GUS) | Colorimetric, fluorescent, or chemiluminescent | colorimetric (histochemical staining with X-gluc) | sensitive, broad linear range, non-isotopic. |
| Green fluorescent protein (GFP) and related molecules (RFP, BFP, GRK2, etc.) | Fluorescent | fluorescent | can be used in live cells; resists photo-bleaching |
| Luciferase (firefly) | bioluminescent | Bio-luminescent | protein is unstable, difficult to reproduce, signal is brief |
| Chloramphenicol acetyltransferase (CAT) | Chromatography, differential extraction, fluorescent, or immunoassay | none | Expensive radioactive substrates, time-consuming, insensitive, narrow linear range |
| β-galactosidase | colorimetric, fluorescence, chemiluminscence | colorimetric (histochemical staining with X-gal), bio-luminescent in live cells | sensitive, broad linear range; some cells have high endogenous activity |
| Secrete alkaline phosphatase (SEAP) | colorimetric, bioluminescent, chemiluminescent | none | Chemiluminscence assay is sensitive and broad linear range; some cells have endogenous alkaline phosphatase activity |

In another aspect of the present invention, a method is provided for identifying a candidate anti-cancer or immunosuppressive compound, the method comprising (a) performing a structure based drug design using a three dimensional structure determined for a crystal of GRK2. The three dimensional structure can comprise atomic coordinates of Protein Data Bank Accession No. 1OMW, incorporated herein by reference in its entirety.

Crystal Structure Docking

According to an aspect of the present invention, crystalline GRK2 protein can be used to determine the ability of a compound of the present invention to bind to an GRK2 protein in a manner predicted by a structure-based drug design method of the present invention. In various aspects of the present thereby inhibiting the binding of an GRK2 ligand or substrate, e.g., DNA, to an GRK2 protein, by blocking the ligand or substrate binding site of an GRK2 protein (referred to herein as substrate analogs). A GRK2 substrate analog refers to a compound that interacts with (e.g., binds to, associates with, modifies) the binding site of an GRK2 protein. A GRK2 substrate analog can, for example, comprise a chemical compound that mimics the Rel- or Rel-like DNA binding domain or other ligand or substrate binding site of an GRK2 protein.

According to the present invention, suitable therapeutic compounds of the present invention include peptides or other organic molecules, and inorganic molecules. Suitable organic molecules include small organic molecules. In various aspects, a therapeutic compound of the present invention is not harmful (e.g., toxic) to an animal when such compound is administered to an animal. Peptides refer to a class of compounds that is small in molecular weight and yields two or more amino acids upon hydrolysis. A polypeptide is comprised of two or more peptides. As used herein, a protein is comprised of one or more polypeptides. Suitable therapeutic compounds to design include peptides composed of "L" and/ or "D" amino acids that are configured as normal or retroinverso peptides, peptidomimetic compounds, small organic molecules, or homo- or hetero-polymers thereof, in linear or branched configurations.

Therapeutic compounds of the present invention can be designed using structure based drug design. Structure based drug design refers to the use of computer simulation to predict a conformation of a peptide, polypeptide, protein, or conformational interaction between a peptide or polypeptide, and a therapeutic compound. In the present teachings, knowledge of the three dimensional structure of the GRK2 protein provides one of skill in the art the ability to design a therapeutic compound that binds to GRK2 proteins, is stable and results in inhibition of a biological response. The three dimensional structure of GRK2 protein (e.g., SEQ ID NO: 3) is disclosed in the Protein Data Bank as Accession No. 1OMW. For example, and without limitation, knowledge of the three dimensional structure of the DNA binding site provides to a skilled artisan the ability to design an analog of a ligand, substrate or polynucleotide which can function as an inhibitor of an GRK2 protein.

Suitable structures and models useful for structure-based drug design include molecular replacement. Methods of molecular replacement are generally known by those of skill in the art and are performed in a software program including, for example, X-PLOR available from Accelerys (San Diego, Calif.). In various aspects of the invention, the three dimensional structure of GRK2 protein useful in a method of molecular replacement according to the present invention has an amino acid sequence that is at least about 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, or 100% identical to the amino acid sequence of the search structure (e.g., GRK2; SEQ ID NO: 3), when the two amino acid sequences are compared using an alignment program such as BLAST (supra). Models of target structures to use in a method of structure-based drug design include models produced by any modeling method disclosed herein, such as, for example, molecular replacement and fold recognition related methods which are well understood in the art. In some aspects of the present invention, structure based drug design can be applied to a structure of GRK2 in complex with a ligand or substrate, and to a model of a target GRK2 structure.

One embodiment of the present invention is a method for designing a drug which interferes with an activity of a GRK2 protein. In various configurations, the method comprises providing a three-dimensional structure of a GRK2 protein comprising at least one ligand of the protein, and designing a chemical compound which is predicted to bind to the protein. The designing can comprise using physical models, such as, for example, ball-and-stick representations of atoms and bonds, or on a digital computer equipped with molecular modeling software. In some configurations, these methods can further include synthesizing the chemical compound, and evaluating the chemical compound for ability to interfere with an activity of the GRK2 protein.

Suitable three dimensional structures of a GRK2 protein and models to use with the present method are disclosed herein. According to the present invention, designing a compound can include creating a new chemical compound or searching databases of libraries of known compounds (e.g., a compound listed in a computational screening database containing three dimensional structures of known compounds). Designing can also include simulating chemical compounds having substitute moieties at certain structural features. In some configurations, designing can include selecting a chemical compound based on a known function of the compound. In some configurations designing can comprise computational screening of one or more databases of compounds in which three dimensional structures of the compounds are known. In these configurations, a candidate compound can be interacted virtually (e.g., docked, aligned, matched, interfaced) with the three dimensional structure of a GRK2 protein by computer equipped with software such as, for example, the AutoDock software package, (The Scripps Research Institute, La Jolla, Calif.) or described by Humblet and Dunbar, Animal Reports in Medicinal Chemistry, vol. 28, pp. 275-283, 1993, M Venuti, ed., Academic Press. Methods for synthesizing candidate chemical compounds are known to those of skill in the art.

Various other methods of structure-based drug design are disclosed in references such as Maulik et al., 1997, *Molecular Biotechnology: Therapeutic Applications and Strategies*, Wiley-Liss, Inc., which is incorporated herein by reference in its entirety. Maulik et al. disclose, for example, methods of directed design, in which the user directs the process of creating novel molecules from a fragment library of appropriately selected fragments; random design, in which the user uses a genetic or other algorithm to randomly mutate fragments and their combinations while simultaneously applying a selection criterion to evaluate the fitness of candidate ligands; and a grid-based approach in which the user calculates the interaction energy between three dimensional structures and small fragment probes, followed by linking together of favorable probe sites.

In one aspect, a chemical compound of the present invention that binds to the RGS Homology Domain can be a chemical compound having chemical and/or stereochemical complementarity with a GRK2 protein. In some configurations, a chemical compound that binds to the selected binding site can associate with an affinity of at least about $10^{-6}$ M, at least about $10^{-7}$ M, or at least about $10^{-8}$ M.

Drug design strategies as specifically described above with regard to residues and regions of the ligand-complexed GRK2 crystal can be similarly applied to other GRK2 protein structures. One of ordinary skill in the art, using the art recognized modeling programs and drug design methods, many of which are described herein, can modify the GRK2 protein design strategy according to differences in amino acid sequence. For example, this strategy can be used to design compounds which regulate insulin resistance in other GRK2 proteins or GRK2 variants. In addition, one of skill in the art can use lead compound structures derived from one GRK2 protein and take into account differences in amino acid residues in other GRK2 proteins or variants.

In the present method of structure-based drug design, it is not necessary to align a candidate chemical compound (i.e., a chemical compound being analyzed in, for example, a computational screening method of the present invention) to each residue in a target site. Suitable candidate chemical compounds can align to a subset of residues described for a target site. In some configurations of the present invention, a candidate chemical compound can comprise a conformation that promotes the formation of covalent or noncovalent crosslinking between the target site and the candidate chemical compound. In certain aspects of the invention, a candidate chemical compound can bind to a surface adjacent to a target site to provide an additional site of interaction in a complex. For example, when designing an antagonist (i.e., a chemical compound that inhibits the binding of a ligand to an GRK2 protein by blocking a binding site or interface), the antagonist can be designed to bind with sufficient affinity to the binding site or to substantially prohibit a ligand (i.e., a molecule that specifically binds to the target site) from binding to a target area. It will be appreciated by one of skill in the art that it is not necessary that the complementarity between a candidate chemical compound and a target site extend over all residues specified here.

In various aspects, the design of a chemical compound possessing stereochemical complementarity can be accomplished by means of techniques that optimize, chemically or geometrically, the "fit" between a chemical compound and a target site. Such techniques are disclosed by, for example, Sheridan and Venkataraghavan, Acc. Chem. Res., vol. 20, p. 322, 1987: Goodford, J. Med. Chem., vol. 27, p. 557, 1984; Beddell, Chem. Soc. Reviews, vol. 279, 1985; Hol, Angew. Chem., vol. 25, p. 767, 1986; and Verlinde and Hol, Structure, vol. 2, p. 577, 1994, each of which is incorporated by this reference herein in their entirety.

Some embodiments of the present invention for structure-based drug design comprise methods of identifying a chemical compound that complements the shape of an GRK2 protein or a structure that is related to an GRK2 protein. Such method is referred to herein as a "geometric approach". In a geometric approach of the present invention, the number of internal degrees of freedom (and the corresponding local minima in the molecular conformation space) can be reduced by considering only the geometric (hard-sphere) interactions of two rigid bodies, where one body (the active site) contains "pockets" or "grooves" that form binding sites for the second body (the complementing molecule, such as a ligand or substrate).

The geometric approach is described by Kuntz et al., J. Mol. Biol., vol. 161, p. 269, 1982, which is incorporated by this reference herein in its entirety. The algorithm for chemical compound design can be implemented using a software program such as AutoDock, available from The Scripps Research Institute (La Jolla, Calif.). One or more extant databases of crystallographic data (e.g., the Cambridge Structural Database System maintained by University Chemical Laboratory, Cambridge University, Lensfield Road, Cambridge CB2 IEW, U.K. or the Protein Data Bank maintained by Rutgers University) can then be searched for chemical compounds that approximate the shape thus defined. Chemical compounds identified by the geometric approach can be modified to satisfy criteria associated with chemical complementarity, such as hydrogen bonding, ionic interactions or Van der Waals interactions.

The crystal docking method may further comprise (b) contacting the candidate inhibitor with a cell comprising GRK2 or a variant or fragment thereof; and (c) detecting inhibition of at least one activity of GRK2, variant or fragment thereof.

In various aspects of the invention, the methods above can be performed wherein the test compound is an antibody. In accordance with yet another aspect of the invention, the antibody can be a monoclonal antibody. In various aspects of the invention, the methods above can be performed wherein the test compound is selected from the group consisting of a ribozyme, antisense compound, triplex-forming molecule, siRNA, and aptamer. In a further aspect of the invention, the siRNA can comprises the sequence of SEQ ID NO: 1.

Anti-GRK2 Abs

The invention makes use of Abs and antibody fragments, such as $F_{ab}$ or $(F_{ab})_2$, that bind immunospecifically to any GRK2 epitopes. "Antibody" (Ab) comprises single Abs directed against GRK2 (anti-GRK2 Ab; including agonist, antagonist, and neutralizing Abs), anti-GRK2 Ab compositions with poly-epitope specificity, single chain anti-GRK2 Abs, and fragments of anti-GRK2 Abs. A "monoclonal antibody" is obtained from a population of substantially homogeneous Abs, i.e., the individual Abs comprising the population are identical except for possible naturally-occurring mutations that may be present in minor amounts. Exemplary Abs include polyclonal (pAb), monoclonal (mAb), humanized, bi-specific (bsAb), and heteroconjugate Abs. Antibodies can be produced by any known method in the art or obtained commercially.

Monovalent Abs

The Abs may be monovalent Abs that consequently do not cross-link with each other. For example, one method involves recombinant expression of Ig light chain and modified heavy chain. Heavy chain truncations generally at any point in the $F_c$ region will prevent heavy chain cross-linking. Alternatively, the relevant cysteine residues are substituted with another amino acid residue or are deleted, preventing crosslinking. In vitro methods are also suitable for preparing monovalent Abs. Abs can be digested to produce fragments, such as $F_{ab}$ fragments.

Humanized and Human Abs

Anti-GRK2 Abs may further comprise humanized or human Abs. Humanized forms of non-human Abs are chimeric Igs, Ig chains or fragments (such as $F_v$, $F_{ab}$, $F_{ab'}$, $F_{(ab')2}$ or other antigen-binding subsequences of Abs) that contain minimal sequence derived from non-human Ig.

Generally, a humanized antibody has one or more amino acid residues introduced from a non-human source. These non-human amino acid residues are often referred to as "import" residues, which are typically taken from an "import" variable domain. Humanization is accomplished by substituting rodent CDRs or CDR sequences for the corresponding sequences of a human antibody. Such "humanized" Abs are chimeric Abs, wherein substantially less than an intact human variable domain has been substituted by the corresponding sequence from a non-human species. In practice, humanized Abs are typically human Abs in which some CDR residues and possibly some FR residues are substituted by residues from analogous sites in rodent Abs. Humanized Abs include human Igs (recipient antibody) in which residues from a complementary determining region (CDR) of the recipient are replaced by residues from a CDR of a non-human species (donor antibody) such as mouse, rat or rabbit, having the desired specificity, affinity and capacity. In some instances, corresponding non-human residues replace $F_v$ framework residues of the human Ig. Humanized Abs may comprise residues that are found neither in the recipient antibody nor in the imported CDR or framework sequences. In general, the humanized antibody comprises substantially all of at least one, and typically two, variable domains, in which most if not all of the CDR regions correspond to those of a non-human Ig and most if not all of the FR regions are those of a human Ig consensus sequence. The humanized antibody optimally also comprises at least a portion of an Ig constant region ($F_c$), typically that of a human Ig.

Human Abs can also be produced using various techniques, including phage display libraries and the preparation of human mAbs. Similarly, introducing human Ig genes into transgenic animals in which the endogenous Ig genes have been partially or completely inactivated can be exploited to synthesize human Abs. Upon challenge, human antibody production is observed, which closely resembles that seen in humans in all respects, including gene rearrangement, assembly, and antibody repertoire.

Bi-Specific mAbs

Bi-specific Abs are monoclonal, preferably human or humanized, that have binding specificities for at least two different antigens. For example, a binding specificity is GRK2; the other is for any antigen of choice, preferably a cell-surface protein or receptor or receptor subunit. Traditionally, the recombinant production of bi-specific Abs is based on the co-expression of two Ig heavy-chain/light-chain pairs, where the two heavy chains have different specificities. Because of the random assortment of Ig heavy and light chains, the resulting hybridomas (quadromas) produce a potential mixture of ten different antibody molecules, of which only one has the desired bi-specific structure. The desired antibody can be purified using affinity chromatography or other techniques.

To manufacture a bi-specific antibody, variable domains with the desired antibody-antigen combining sites are fused to Ig constant domain sequences. The fusion is preferably with an Ig heavy-chain constant domain, comprising at least part of the hinge, CH2, and CH3 regions. Preferably, the first heavy-chain constant region (CH1) containing the site necessary for light-chain binding is in at least one of the fusions. DNAs encoding the Ig heavy-chain fusions and, if desired, the Ig light chain, are inserted into separate expression vectors and are co-transfected into a suitable host organism.

The interface between a pair of antibody molecules can be engineered to maximize the percentage of heterodimers that are recovered from recombinant cell culture. The preferred interface comprises at least part of the CH3 region of an antibody constant domain. In this method, one or more small amino acid side chains from the interface of the first antibody molecule are replaced with larger side chains (e.g., tyrosine or tryptophan). Compensatory "cavities" of identical or similar size to the large side chain(s) are created on the interface of the second antibody molecule by replacing large amino acid side chains with smaller ones (e.g., alanine or threonine). This mechanism increases the yield of the heterodimer over unwanted end products such as homodimers.

Bi-specific Abs can be prepared as full length Abs or antibody fragments (e.g., $F_{(ab')2}$ bi-specific Abs). One technique to generate bi-specific Abs exploits chemical linkage. Intact Abs can be proteolytically cleaved to generate $F_{(ab')2}$ fragments. Fragments are reduced with a dithiol complexing agent, such as sodium arsenite, to stabilize vicinal dithiols and prevent intermolecular disulfide formation. The generated $F_{ab'}$ fragments are then converted to thionitrobenzoate (TNB) derivatives. One of the $F_{ab'}$-TNB derivatives is then reconverted to the $F_{ab'}$-thiol by reduction with mercaptoethylamine and is mixed with an equimolar amount of the other $F_{ab'}$-TNB derivative to form the bi-specific antibody. The produced bi-specific Abs can be used as agents for the selective immobilization of enzymes.

$F_{ab'}$ fragments may be directly recovered from *E. coli* and chemically coupled to form bi-specific Abs. For example, fully humanized bi-specific $F_{(ab')2}$Abs can be produced by methods known to those of skill in the art. Each $F_{ab'}$ fragment is separately secreted from *E. coli* and directly coupled chemically in vitro, forming the bi-specific antibody.

Various techniques for making and isolating bi-specific antibody fragments directly from recombinant cell culture have also been described. For example, leucine zipper motifs can be exploited. Peptides from the Fos and Jun proteins are linked to the $F_{ab'}$ portions of two different Abs by gene fusion. The antibody homodimers are reduced at the hinge region to form monomers and then re-oxidized to form antibody heterodimers. This method can also produce antibody homodimers. The "diabody" technology provides an alternative method to generate bi-specific antibody fragments. The fragments comprise a heavy-chain variable domain ($V_H$) connected to a light-chain variable domain ($V_L$) by a linker that is too short to allow pairing between the two domains on the same chain. The $V_H$ and $V_L$ domains of one fragment are forced to pair with the complementary $V_L$ and $V_H$ domains of another fragment, forming two antigen-binding sites. Another strategy for making bi-specific antibody fragments is the use of single-chain $F_v$ ($sF_v$) dimers. Abs with more than two valences are also contemplated, such as tri-specific Abs.

Exemplary bi-specific Abs may bind to two different epitopes on a given GRK2. Alternatively, cellular defense mechanisms can be restricted to a particular cell expressing the particular GRK2: an anti-GRK2 arm may be combined with an arm that binds to a leukocyte triggering molecule, such as a T-cell receptor molecule (e.g., CD2, CD3, CD28, or B7), or to $F_c$ receptors for IgG ($F_c\gamma R$), such as $F_c\gamma RI$ (CD64), $F_c\gamma RII$ (CD32) and $F_c\gamma RIII$ (CD16). Bi-specific Abs may also be used to target cytotoxic agents to cells that express a particular GRK2. These Abs possess a GRK2-binding arm and an arm that binds a cytotoxic agent or a radionuclide chelator.

Heteroconjugate Abs

Heteroconjugate Abs, consisting of two covalently joined Abs, have been proposed to target immune system cells to unwanted cells and for treatment of human immunodeficiency virus (HIV) infection. Abs prepared in vitro using synthetic protein chemistry methods, including those involving cross-linking agents, are contemplated. For example, immunotoxins may be constructed using a disulfide exchange reaction or by forming a thioether bond. Examples of suitable reagents include iminothiolate and methyl-4-mercaptobutyrimidate.

Immunoconjugates

Immunoconjugates may comprise an antibody conjugated to a cytotoxic agent such as a chemotherapeutic agent, toxin (e.g., an enzymatically active toxin or fragment of bacterial, fungal, plant, or animal origin), or a radioactive isotope (i.e., a radioconjugate).

Useful enzymatically-active toxins and fragments include Diphtheria A chain, non-binding active fragments of Diphtheria toxin, exotoxin A chain from *Pseudomonas aeruginosa*, ricin A chain, abrin A chain, modeccin A chain, α-sarcin, *Aleurites fordii* proteins, Dianthin proteins, *Phytolaca americana* proteins, *Momordica charantia* inhibitor, curcin, crotin, *Sapaonaria officinalis* inhibitor, gelonin, mitogellin, restrictocin, phenomycin, enomycin, and the tricothecenes. A variety of radionuclides are available for the production of radioconjugated Abs, such as $^{212}Bi$, $^{131}I$, $^{131}In$, $^{90}Y$, and $^{186}Re$.

Conjugates of the antibody and cytotoxic agent are made using a variety of bifunctional protein-coupling agents, such as N-succinimidyl-3-(2-pyridyldithiol) propionate (SPDP), iminothiolane (IT), bi-functional derivatives of imidoesters (such as dimethyl adipimidate HCl), active esters (such as disuccinimidyl suberate), aldehydes (such as glutareldehyde), bis-azido compounds (such as bis(p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared by methods known to those of skill in the art. $^{14}$C-labeled 1-isothiocyanatobenzyl-3-methyldiethylene triaminepentaacetic acid (MX-DTPA) is an exemplary chelating agent for conjugating radionuclide to antibody.

In another embodiment, the antibody may be conjugated to a "receptor" (such as streptavidin) for utilization in tumor pre-targeting wherein the antibody-receptor conjugate is administered to the patient, followed by removal of unbound conjugate from the circulation using a clearing agent and then administration of a streptavidin "ligand" (e.g., biotin) that is conjugated to a cytotoxic agent (e.g., a radionuclide).

Effector Function Engineering

The antibody can be modified to enhance its effectiveness in treating a disease, such as metabolic syndrome. For example, cysteine residue(s) may be introduced into the $F_c$ region, thereby allowing interchain disulfide bond formation in this region. Such homodimeric Abs may have improved internalization capability and/or increased complement-mediated cell killing and antibody-dependent cellular cytotoxicity (ADCC). Homodimeric Abs with enhanced anti-tumor activity can be prepared using hetero-bifunctional cross-linkers by methods known to those of skill in the art. Alternatively, an antibody engineered with dual $F_c$ regions may have enhanced complement lysis.

Diagnostic Applications of Abs Directed Against GRK2

Anti-GRK2 Abs can be used to localize and/or quantitate GRK2 (e.g., for use in measuring levels of GRK2 within tissue samples or for use in diagnostic methods, etc.). Anti-GRK2 epitope Abs can be utilized as pharmacologically active compounds and screened according to the methods of the present invention.

Anti-GRK2 Abs can be used to isolate GRK2 by standard techniques, such as immunoaffinity chromatography or immunoprecipitation. These approaches facilitate purifying endogenous GRK2 antigen-containing polypeptides from cells and tissues. These approaches, as well as others, can be used to detect GRK2 in a sample to evaluate the abundance and pattern of expression of the antigenic protein. Anti-GRK2 Abs can be used to monitor protein levels in tissues as part of a clinical testing procedure; for example, to determine the efficacy of a given treatment regimen. Coupling the antibody to a detectable substance (label) allows detection of Ab-antigen complexes. Classes of labels include fluorescent, luminescent, bioluminescent, and radioactive materials, enzymes and prosthetic groups. Useful labels include horseradish peroxidase, alkaline phosphatase, β-galactosidase, acetylcholinesterase, streptavidin/biotin, avidin/biotin, umbelliferone, fluorescein, fluorescein isothiocyanate, rhodamine, dichlorotriazinylamine fluorescein, dansyl chloride, phycoerythrin, luminol, luciferase, luciferin, aequorin, and $^{125}$I, $^{131}$I, $^{35}$S or $^3$H.

Antibody Therapeutics

Abs of the invention, including polyclonal, monoclonal, humanized and fully human Abs, can be used therapeutically. Such agents will generally be employed to treat or prevent a disease or pathology in a subject. An antibody preparation, preferably one having high antigen specificity and affinity generally mediates an effect by binding the target epitope(s). Generally, administration of such Abs may mediate one of two effects: (1) the antibody may prevent ligand binding, eliminating endogenous ligand binding and subsequent signal transduction, or (2) the antibody elicits a physiological result by binding an effector site on the target molecule, initiating signal transduction.

A therapeutically effective amount of an antibody relates generally to the amount needed to achieve a therapeutic objective, epitope binding affinity, administration rate, and depletion rate of the antibody from a subject. Common ranges for therapeutically effective doses may be, as a nonlimiting example, from about 0.1 mg/kg body weight to about 50 mg/kg body weight. Dosing frequencies may range, for example, from twice daily to once a week.

Pharmaceutical Compositions for Abs

Anti-GRK2 Abs, as well as other GRK2 interacting molecules (such as aptamers) identified in other assays, can be administered in pharmaceutical compositions as disclosed, infra, to treat various disorders. Abs that are internalized are preferred when whole Abs are used as inhibitors. Liposomes may also be used as a delivery vehicle for intracellular introduction. Where antibody fragments are used, the smallest inhibitory fragment that specifically binds to the epitope is preferred. For example, peptide molecules can be designed that bind a preferred epitope based on the variable-region sequences of a useful antibody. Such peptides can be synthesized chemically and/or produced by recombinant DNA technology. Formulations may also contain more than one active compound for a particular treatment, preferably those with activities that do not adversely affect each other. The composition may comprise an agent that enhances function, such as a cytotoxic agent, cytokine, chemotherapeutic agent, or growth-inhibitory agent.

The active ingredients can also be entrapped in microcapsules prepared by coacervation techniques or by interfacial polymerization; for example, hydroxymethylcellulose or gelatin-microcapsules and poly-(methylmethacrylate) microcapsules, respectively, in colloidal drug delivery systems (for example, liposomes, albumin microspheres, microemulsions, nanoparticles, and nanocapsules) or in macroemulsions. The formulations to be used for in vivo administration are highly preferred to be sterile. This is readily accomplished by filtration through sterile filtration membranes or any of a number of techniques.

Sustained-release preparations may also be prepared, such as semi-permeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides, copolymers of L-glutamic acid and γ ethyl-L-glutamate, non-degradable ethylene-vinyl acetate, degradable lactic acid-glycolic acid copolymers such as injectable microspheres composed of lactic acid-glycolic acid copolymer, and poly-D-(−)-3-hydroxybutyric acid. While polymers such as ethylene-vinyl acetate and lactic acid-glycolic acid enable release of molecules for over 100 days, certain hydrogels release proteins for shorter time periods and may be preferred.

In various aspects, the inhibitor can also be selected from the group consisting of a ribozyme, antisense compound, triplex-forming molecule, siRNA, and aptamer.

Ribozymes

Ribozyme molecules designed to catalytically cleave GRK2 mRNA transcripts can also be used to prevent translation of GRK2 mRNAs and expression of a GRK2 protein (see, e.g., Wright and Kearney, Cancer Invest. 19:495, 2001; Lewin and Hauswirth, Trends Mol. Med. 7:221, 2001; Sarver et al. (1990) Science 247:1222-1225 and U.S. Pat. No. 5,093, 246). As one example, hammerhead ribozymes that cleave mRNAs at locations dictated by flanking regions that form complementary base pairs with the target mRNA might be used so long as the target mRNA has the following common sequence: 5'-UG-3'. See, e.g., Haseloff and Gerlach (1988) Nature 334:585-591. As another example, hairpin and hepatitis delta virus ribozymes may also be used. See, e.g., Bartolome et al. (2004) Minerva Med. 95(1):11-24. To increase efficiency and minimize the intracellular accumulation of non-functional mRNA transcripts, a ribozyme should be engineered so that the cleavage recognition site is located near the 5' end of the target GRK2 mRNA. Ribozymes within the invention can be delivered to a cell using a vector as described herein.

Other methods can also be used to reduce GRK2 gene expression in a cell. For example, GRK2 gene expression can be reduced by inactivating or "knocking out" the GRK2 gene or its promoter using targeted homologous recombination. See, e.g., Kempin et al., Nature 389: 802 (1997); Smithies et al. (1985) Nature 317:230-234; Thomas and Capecchi (1987) Cell 51:503-512; and Thompson et al. (1989) Cell 5:313-321. For example, a mutant, non-functional GRK2 gene variant (or a completely unrelated DNA sequence) flanked by DNA homologous to the endogenous GRK2 gene (either the coding regions or regulatory regions of the GRK2 gene) can be used, with or without a selectable marker and/or a negative selectable marker, to transfect cells that express GRK2 protein in vivo.

GRK2 gene expression might also be reduced by targeting deoxyribonucleotide sequences complementary to the regulatory region of the GRK2 gene (i.e., the GRK2 promoter and/or enhancers) to form triple helical structures that prevent transcription of the GRK2 gene in target cells. See generally, Helene, C. (1991) Anticancer Drug Des. 6(6): 569-84; Helene, C., et al. (1992) Ann. N.Y. Acad. Sci. 660:27-36; and Maher, L. J. (1992) Bioassays 14(12): 807-15. Nucleic acid molecules to be used in this technique are preferably single stranded and composed of deoxyribonucleotides. The base composition of these oligonucleotides should be selected to promote triple helix formation via Hoogsteen base pairing rules, which generally require sizable stretches of either purines or pyrimidines to be present on one strand of a duplex. Nucleotide sequences may be pyrimidine-based, which will result in TAT and CGC triplets across the three associated strands of the resulting triple helix. The pyrimidine-rich molecules provide base complementarity to a purine-rich region of a single strand of the duplex in a parallel orientation to that strand. In addition, nucleic acid molecules may be chosen that are purine-rich, e.g., containing a stretch of G residues. These molecules will form a triple helix with a DNA duplex that is rich in GC pairs, in which the majority of the purine residues are located on a single strand of the targeted duplex, resulting in CGC triplets across the three strands in the triplex. The potential sequences that can be targeted for triple helix formation may be increased by creating a so called "switchback" nucleic acid molecule. Switchback molecules are synthesized in an alternating 5'-3',3'-5' manner, such that they base pair with first one strand of a duplex and then the other, eliminating the necessity for a sizable stretch of either purines or pyrimidines to be present on one strand of a duplex.

The antisense RNA and DNA, ribozyme, and triple helix molecules of the invention may be prepared by any method known in the art for the synthesis of DNA and RNA molecules. These include techniques for chemically synthesizing oligodeoxyribonucleotides and oligoribonucleotides well known in the art such as for example solid phase phosphoramide chemical synthesis. RNA molecules may be generated by in vitro and in vivo transcription of DNA sequences encoding the antisense RNA molecule. Such DNA sequences may be incorporated into a wide variety of vectors which incorporate suitable RNA polymerase promoters. Alternatively, antisense cDNA constructs that synthesize antisense RNA constitutively or inducibly, depending on the promoter used, can be introduced stably into cell lines.

Anti-Sense Nucleic Acids

Using antisense and sense GRK2 oligonucleotides can prevent GRK2 polypeptide expression. These oligonucleotides bind to target nucleic acid sequences, forming duplexes that block transcription or translation of the target sequence by enhancing degradation of the duplexes, terminating prematurely transcription or translation, or by other means.

Antisense or sense oligonucleotides are singe-stranded nucleic acids, either RNA or DNA, which can bind target GRK2 mRNA (sense) or GRK2 DNA (antisense) sequences. Anti-sense nucleic acids can be designed according to Watson and Crick or Hoogsteen base pairing rules. The anti-sense nucleic acid molecule can be complementary to the entire coding region of GRK2 mRNA, but more preferably, to only a portion of the coding or noncoding region of GRK2 mRNA. For example, the anti-sense oligonucleotide can be complementary to the region surrounding the translation start site of GRK2 mRNA. Antisense or sense oligonucleotides may comprise a fragment of the GRK2 DNA coding region of at least about 14 nucleotides, preferably from about 14 to 30 nucleotides. In general, antisense RNA or DNA molecules can comprise at least 5, 10, 15, 20, 25, 30, 35, 40, 45, 50, 55, 60, 65, 70, 75, 80, 85, 90, 95, 100 bases in length or more. Methods to derive antisense or a sense oligonucleotides from a given cDNA sequence are known in the art.

Examples of modified nucleotides that can be used to generate the anti-sense nucleic acid include: 5-fluorouracil, 5-bromouracil, 5-chlorouracil, 5-iodouracil, hypoxanthine, xanthine, 4-acetylcytosine, 5-(carboxyhydroxylmethyl) uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl) uracil, (acp3)w, and 2,6-diaminopurine. Alternatively, the anti-sense nucleic acid can be produced biologically using an expression vector into which a nucleic acid has been sub-cloned in an anti-sense orientation such that the transcribed RNA will be complementary to a target nucleic acid of interest.

To introduce antisense or sense oligonucleotides into target cells (cells containing the target nucleic acid sequence), any gene transfer method may be used. Examples of gene transfer methods include (1) biological, such as gene transfer vectors like Epstein-Barr virus or conjugating the exogenous DNA to a ligand-binding molecule, (2) physical, such as electroporation and injection, and (3) chemical, such as $CaPO_4$ precipitation and oligonucleotide-lipid complexes.

An antisense or sense oligonucleotide is inserted into a suitable gene transfer retroviral vector. A cell containing the target nucleic acid sequence is contacted with the recombinant retroviral vector, either in vivo or ex vivo. Examples of suitable retroviral vectors include those derived from the murine retrovirus M-MuLV, N2 (a retrovirus derived from M-MuLV), or the double copy vectors designated DCT5A, DCT5B and DCT5C. To achieve sufficient nucleic acid molecule transcription, vector constructs in which the transcription of the anti-sense nucleic acid molecule is controlled by a strong pol II or pol III promoter are preferred.

To specify target cells in a mixed population of cells cell surface receptors that are specific to the target cells can be exploited. Antisense and sense oligonucleotides can be conjugated to a ligand-binding molecule. Ligands are chosen for receptors that are specific to the target cells. Examples of suitable ligand-binding molecules include cell surface receptors, growth factors, cytokines, or other ligands that bind to cell surface receptors or molecules. Preferably, conjugation of the ligand-binding molecule does not substantially interfere with the ability of the receptors or molecule to bind the ligand-binding molecule conjugate, or block entry of the sense or antisense oligonucleotide or its conjugated version into the cell.

Liposomes efficiently transfer sense or an antisense oligonucleotide to cells. The sense or antisense oligonucleotide-lipid complex is preferably dissociated within the cell by an endogenous lipase.

The anti-sense nucleic acid molecule of the invention may be an α-anomeric nucleic acid molecule. An α-anomeric nucleic acid molecule forms specific double-stranded hybrids with complementary RNA in which, contrary to the usual α-units, the strands run parallel to each other. The anti-sense nucleic acid molecule can also comprise a 2'-o-methylribonucleotide or a chimeric RNA-DNA analogue.

Modifications of antisense and sense oligonucleotides can augment their effectiveness. Modified sugar-phosphodiester bonds or other sugar linkages, increase in vivo stability by conferring resistance to endogenous nucleases without disrupting binding specificity to target sequences. Other modifications can increase the affinities of the oligonucleotides for their targets, such as covalently linked organic moieties or poly-(L)-lysine. Other attachments modify binding specificities of the oligonucleotides for their targets, including metal complexes or intercalating (e.g., ellipticine) and alkylating agents.

For example, the deoxyribose phosphate backbone of the nucleic acids can be modified to generate peptide nucleic acids. "Peptide nucleic acids" or "PNAs" refer to nucleic acid mimics (e.g., DNA mimics) in that the deoxyribose phosphate backbone is replaced by a pseudopeptide backbone and only the four natural nucleobases are retained. The neutral backbone of PNAs allows for specific hybridization to DNA and RNA under conditions of low ionic strength. The synthesis of PNA oligomers can be performed using standard solid phase peptide synthesis protocols known to those of skill in the art.

PNAs of GRK2 can be used in therapeutic and diagnostic applications. For example, PNAs can be used as anti-sense or antigene agents for sequence-specific modulation of gene expression by inducing transcription or translation arrest or inhibiting replication. GRK2 PNAs may also be used in the analysis of single base pair mutations (e.g., PNA directed PCR clamping; as artificial restriction enzymes when used in combination with other enzymes, e.g., $S_1$ nucleases, or as probes or primers for DNA sequence and hybridization.

PNAs of GRK2 can be modified to enhance their stability or cellular uptake. Lipophilic or other helper groups may be attached to PNAs, PNA-DNA dimmers formed, or the use of liposomes or other drug delivery techniques. For example, PNA-DNA chimeras can be generated that may combine the advantageous properties of PNA and DNA. Such chimeras allow DNA recognition enzymes (e.g., RNase H and DNA polymerases) to interact with the DNA portion while the PNA portion provides high binding affinity and specificity. PNA-DNA chimeras can be linked using linkers of appropriate lengths selected in terms of base stacking, number of bonds between the nucleobases, and orientation. The synthesis of PNA-DNA chimeras can be performed by methods known to those of skill in the art. For example, a DNA chain can be synthesized on a solid support using standard phosphoramidite coupling chemistry, and modified nucleoside analogs, e.g., 5'-(4-methoxytrityl)amino-5'-deoxy-thymidine phosphoramidite, can be used between the PNA and the 5' end of DNA. PNA monomers are then coupled in a stepwise manner to produce a chimeric molecule with a 5' PNA segment and a 3' DNA segment. Alternatively, chimeric molecules can be synthesized with a 5' DNA segment and a 3' PNA segment.

The oligonucleotide may include other appended groups such as peptides (e.g., for targeting host cell receptors in vivo), or agents facilitating transport across the cell membrane or the blood-brain barrier. In addition, oligonucleotides can be modified with hybridization-triggered cleavage agents or intercalating agents. The oligonucleotide may be conjugated to another molecule, e.g., a peptide, a hybridization triggered cross-linking agent, a transport agent, a hybridization-triggered cleavage agent, and the like.

Triple-Helix Molecules

To inhibit transcription, triple-helix nucleic acids that are single-stranded and comprise deoxynucleotides are useful antagonists. These oligonucleotides are designed such that triple-helix formation via Hoogsteen base-pairing rules is promoted, generally requiring stretches of purines or pyrimidines.

Aptamers

Aptamers are short oligonucleotide sequences that can be used to recognize and specifically bind almost any molecule. The systematic evolution of ligands by exponential enrichment (SELEX) process (see, Ausubel, supra) is powerful and can be used to find such aptamers. Aptamers have many diagnostic and clinical uses; almost any use in which an antibody has been used clinically or diagnostically, aptamers too may be used. In addition, are cheaper to make once they have been identified, and can be easily applied in a variety of formats, including administration in pharmaceutical compositions, in bioassays, and diagnostic tests.

RNA Interference (RNAi)

The use of short-interfering RNA (siRNA) is a technique known in the art for inhibiting expression of a target gene by introducing exogenous RNA into a living cell (Elbashir et al. 2001. Nature. 411:494-498). siRNAs suppress gene expression through a highly regulated enzyme-mediated process called RNA interference (RNAi). RNAi involves multiple RNA-protein interactions characterized by four major steps: assembly of siRNA with the RNA-induced silencing complex (RISC), activation of the RISC, target recognition and target cleavage. Therefore, identifying siRNA-specific features likely to contribute to efficient processing at each step is beneficial efficient RNAi. Reynolds et al. provide methods for identifying such features. A. Reynolds et al., "Rational siRNA design for RNA interference", Nature Biotechnology 22(3), March 2004. In that study, eight characteristics associated with siRNA functionality were identified: low G/C content, a bias towards low internal stability at the sense strand 3'-terminus, lack of inverted repeats, and sense strand base preferences (positions 3, 10, 13 and 19). Further analyses revealed that application of an algorithm incorporating all eight criteria significantly improves potent siRNA selection. siRNA sequences that contain internal repeats or palindromes may form internal fold-back structures. These hairpin-like structures may exist in equilibrium with the duplex form, reducing the effective concentration and silencing potential of the siRNA. The relative stability and propensity to form internal hairpins can be estimated by the predicted melting temperatures ($T_M$). Sequences with high Tm values would favor internal hairpin structures.

siRNA can be used either ex vivo or in vivo, making it useful in both research and therapeutic settings. Unlike in other antisense technologies, the RNA used in the siRNA technique has a region with double-stranded structure that is made identical to a portion of the target gene, thus making inhibition sequence-specific. Double-stranded RNA-mediated inhibition has advantages both in the stability of the material to be delivered and the concentration required for effective inhibition.

The extent to which there is loss of function of the target gene can be titrated using the dose of double stranded RNA delivered. A reduction or loss of gene expression in at least 99% of targeted cells has been shown. See, e.g., U.S. Pat. No. 6,506,559. Lower doses of injected material and longer times after administration of siRNA may result in inhibition in a smaller fraction of cells. Quantitation of gene expression in a cell show similar amounts of inhibition at the level of accumulation of target mRNA or translation of target protein.

The RNA used in this technique can comprise one or more strands of polymerized ribonucleotides, and modification can be made to the sugar-phosphate backbone as disclosed above. The double-stranded structure is often formed using either a single self-complementary RNA strand (hairpin) or two complementary RNA strands. RNA containing a nucleotide sequences identical to a portion of the target gene is preferred for inhibition, although sequences with insertions, deletions, and single point mutations relative to the target sequence can also be used for inhibition. Sequence identity may be optimized using alignment algorithms known in the art and through calculating the percent difference between the nucleotide sequences. The duplex region of the RNA could also be described in functional terms as a nucleotide sequence that is capable of hybridizing with a portion of the target gene transcript.

siRNA can often be a more effective therapeutic tool than other types of gene suppression due to siRNA's potent gene inhibition and ability to target receptors with a specificity can reach down to the level of single-nucleotide polymorphisms. Such specificity generally results in fewer side effects than is seen in conventional therapies, because other genes are not be affected by application of a sufficiently sequence-specific siRNA.

There are multiple ways to deliver siRNA to the appropriate target. Standard transfection techniques may be used, in which siRNA duplexes are incubated with cells of interest and then processed using standard commercially available kits. Electroporation techniques of transfection may also be appropriate. Cells or organisms can be soaked in a solution of the siRNA, allowing the natural uptake processes of the cells or organism to introduce the siRNA into the system. Viral constructs packaged into a viral particle would both introduce the siRNA into the cell line or organism and also initiate transcription through the expression construct. Other methods known in the art for introducing nucleic acids to cells may also be used, including lipid-mediated carrier transport, chemical-mediated transport, such as calcium phosphate, and the like.

For therapeutic uses, tissue-targeted nanoparticles may serve as a delivery vehicle for siRNA These nanoparticles carry the siRNA exposed on the surface, which is then available to bind to the target gene to be silenced. Schiffelers, et al., Nucleic Acids Research 2004 32(19):e149. These nanoparticles may be introduced into the cells or organisms using the above described techniques already known in the art. RGD peptides have been shown to be effective at targeting the neovasculature that accompanies the growth of tumors. Designing the appropriate nanoparticles for a particular illness is a matter of determining the appropriate targets for the particular disease. In the case of diabetes and pancreatic cancer, the present invention has already revealed potential targets for this powerful therapy.

Other delivery vehicles for therapeutic uses in humans include pharmaceutical compositions, intracellular injection, and intravenous introduction into the vascular system. Inhibition of gene expression can be confirmed by using biochemical techniques such as RNA solution hybridization, nuclease protection, Northern hybridization, reverse transcription, gene expression monitoring with a microarray, antibody binding, enzyme linked immunosorbent assay (ELISA), Western blotting, radioimmunoassay (RIA), other immunoassays, and fluorescence activated cell analysis (FACS). For RNA-mediated inhibition in a cell line or whole organism, gene expression may be assayed using a reporter or drug resistance gene whose protein product can be easily detected and quantified. Such reporter genes include acetohydroxyacid synthase (AHAS), alkaline phosphatase (AP), beta galactosidase (LacZ), beta glucoronidase (GUS), chloramphenicol acetyltransferase (CAT), green fluorescent protein (GFP), horseradish peroxidase (HRP), luciferase (Luc), nopaline synthase (NOS), octopine synthase (OCS), and derivatives thereof. Multiple selectable markers are available that confer resistance to ampicillin, bleomycin, chloramphenicol, gentamycin, hygromycin, kanamycin, lincomycin, methotrexate, phosphinothricin, puromycin, and tetracyclin. These techniques are well known and easily practiced by those skilled in the art. For in vivo use in humans, reduction or elimination of symptoms of illness will confirm inhibition of the target gene's expression.

In various aspects of the invention, the methods above can be performed wherein the candidate compound is formulated in combination with an agent selected from the group consisting of a pharmaceutically acceptable carrier, a controlled-release component, a pharmaceutically acceptable salt, and any combination thereof.

Pharmaceutical Preparations and Methods of Administration

The identified compounds treat, inhibit, control and/or prevent, or at least partially arrest or partially prevent, metabolic syndrome, including insulin resistance and Type 2 diabetes mellitus and can be administered to a subject at therapeutically effective doses for the inhibition, prevention, prophylaxis or therapy for such disease. The compounds of the present invention comprise a therapeutically effective dosage of an insulin sensitizing compound, a term which includes therapeutically, inhibitory, preventive and prophylactically effective doses of the compounds of the present invention and is more particularly defined below. Without being bound to any particular theory, applicants surmise that these pharmaceutical compounds prevent insulin resistance when administered to a subject suffering from a related condition by GRK2 stimulation. The subject is preferably an animal, including, but not limited to, mammals, reptiles and avians, more preferably horses, cows, dogs, cats, sheep, pigs, and chickens, and most preferably human.

Therapeutically Effective Dosage

Toxicity and therapeutic efficacy of such compounds can be determined by standard pharmaceutical procedures in cell cultures or experimental animals for determining the $LD_{50}$ (the dose lethal to 50% of the population) and the $ED_{50}$, (the dose therapeutically effective in 50% of the population). The dose ratio between toxic and therapeutic effects is the therapeutic index that can be expressed as the ratio $LD_{50}/ED_{50}$. Compounds that exhibit large therapeutic indices are preferred. While compounds exhibiting toxic side effects may be used, care should be taken to design a delivery system that targets such compounds to the site affected by the disease or disorder in order to minimize potential damage to unaffected cells and reduce side effects.

The data obtained from the cell culture assays and animal studies can be used in formulating a range of dosages for use in humans and other mammals. The dosage of such compounds lies preferably within a range of circulating plasma or other bodily fluid concentrations that include the $ED_{50}$ with little or no toxicity. The dosage may vary within this range depending upon the dosage form employed and the route of administration utilized. For any compound of the invention, the therapeutically effective dose can be estimated initially from cell culture assays. A dosage may be formulated in animal models to achieve a circulating plasma concentration range that includes the $IC_{50}$ (the concentration of the test compound that achieves a half-maximal inhibition of symptoms) as determined in cell culture. Such information can be used to more accurately determine useful dosages in humans and other mammals. Compound levels in plasma may be measured, for example, by high performance liquid chromatography.

The amount of a compound that may be combined with a pharmaceutically acceptable carrier to produce a single dosage form will vary depending upon the host treated and the particular mode of administration. It will be appreciated by those skilled in the art that the unit content of a compound contained in an individual dose of each dosage form need not in itself constitute a therapeutically effective amount, as the necessary therapeutically effective amount could be reached by administration of a number of individual doses. The selection of dosage depends upon the dosage form utilized, the condition being treated, and the particular purpose to be achieved according to the determination of those skilled in the art.

The dosage regime for treating a disease or condition with the compounds of the invention is selected in accordance with a variety of factors, including the type, age, weight, sex, diet and medical condition of the patient, the route of administration, pharmacological considerations such as activity, efficacy, pharmacokinetic and toxicology profiles of the particular compound employed, whether a compound delivery system is utilized and whether the compound is administered as a pro-drug or part of a drug combination. Thus, the dosage regime actually employed may vary widely from subject to subject.

Formulations and Use

The compounds of the present invention may be formulated by known methods for administration to a subject using several routes which include, but are not limited to, parenteral, oral, topical, intradermal, intramuscular, intraperitoneal, intravenous, subcutaneous, intranasal, epidural, and ophthalmic routes. The individual compounds may also be administered in combination with one or more additional compounds of the present invention and/or together with other biologically active or biologically inert agents. Such biologically active or inert agents may be in fluid or mechanical communication with the compound(s) or attached to the compound(s) by ionic, covalent, Van der Waals, hydrophobic, hydrophillic or other physical forces. It is preferred that administration is localized in a subject, but administration may also be systemic.

The compounds of the present invention may be formulated by any conventional manner using one or more pharmaceutically acceptable carriers and/or excipients. Thus, the compounds and their pharmaceutically acceptable salts and solvates may be specifically formulated for administration, e.g., by inhalation or insufflation (either through the mouth or the nose) or oral, buccal, parenteral or rectal administration. The compounds may take the form of charged, neutral and/or other pharmaceutically acceptable salt forms. Examples of pharmaceutically acceptable carriers include, but are not limited to, those described in REMINGTON'S PHARMACEUTICAL SCIENCES (A. R. Gennaro, Ed.), 20th edition, Williams & Wilkins PA, USA (2000).

The compounds may also take the form of solutions, suspensions, emulsions, tablets, pills, capsules, powders, controlled- or sustained-release formulations and the like. Such formulations will contain a therapeutically effective amount of the compound, preferably in purified form, together with a suitable amount of carrier so as to provide the form for proper administration to the patient. The formulation should suit the mode of administration.

Parenteral Administration

The compound may be formulated for parenteral administration by injection, e.g., by bolus injection or continuous infusion. Formulations for injection may be presented in unit dosage form in ampoules or in multi-dose containers with an optional preservative added. The parenteral preparation can be enclosed in ampoules, disposable syringes or multiple dose vials made of glass, plastic or the like. The formulation may take such forms as suspensions, solutions or emulsions in oily or aqueous vehicles, and may contain formulatory agents such as suspending, stabilizing and/or dispersing agents.

For example, a parenteral preparation may be a sterile injectable solution or suspension in a nontoxic parenterally acceptable diluent or solvent (e.g., as a solution in 1,3-butanediol). Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid may be used in the parenteral preparation.

Alternatively, the compound may be formulated in powder form for constitution with a suitable vehicle, such as sterile pyrogen-free water, before use. For example, a compound suitable for parenteral administration may comprise a sterile isotonic saline solution containing between 0.1 percent and 90 percent weight per volume of the compound. By way of example, a solution may contain from about 5 percent to about 20 percent, more preferably from about 5 percent to about 17 percent, more preferably from about 8 to about 14 percent, and still more preferably about 10 percent of the compound. The solution or powder preparation may also include a solubilizing agent and a local anesthetic such as lignocaine to ease pain at the site of the injection. Other methods of parenteral delivery of compounds will be known to the skilled artisan and are within the scope of the invention.

Oral Administration

For oral administration, the compound may take the form of tablets or capsules prepared by conventional means with pharmaceutically acceptable excipients such as binding agents, fillers, lubricants and disintegrants:

A. Binding Agents

Binding agents include, but are not limited to, corn starch, potato starch, or other starches, gelatin, natural and synthetic gums such as acacia, sodium alginate, alginic acid, other alginates, powdered tragacanth, guar gum, cellulose and its derivatives (e.g., ethyl cellulose, cellulose acetate, carboxymethyl cellulose calcium, sodium carboxymethyl cellulose), polyvinyl pyrrolidone, methyl cellulose, pre-gelatinized starch, hydroxypropyl methyl cellulose, (e.g., Nos. 2208, 2906, 2910), microcrystalline cellulose, and mixtures thereof. Suitable forms of microcrystalline cellulose include, for example, the materials sold as AVICEL-PH-101, AVICEL-PH-103 and AVICEL-PH-105 (available from FMC Corporation, American Viscose Division, Avicel Sales, Marcus Hook, Pa., USA). An exemplary suitable binder is a mixture of microcrystalline cellulose and sodium carboxymethyl cellulose sold as AVICEL RC-581 by FMC Corporation.

B. Fillers

Fillers include, but are not limited to, talc, calcium carbonate (e.g., granules or powder), lactose, microcrystalline cellulose, powdered cellulose, dextrates, kaolin, mannitol, silicic acid, sorbitol, starch, pre-gelatinized starch, and mixtures thereof.

C. Lubricants

Lubricants include, but are not limited to, calcium stearate, magnesium stearate, mineral oil, light mineral oil, glycerin, sorbitol, mannitol, polyethylene glycol, other glycols, stearic acid, sodium lauryl sulfate, talc, hydrogenated vegetable oil (e.g., peanut oil, cottonseed oil, sunflower oil, sesame oil, olive oil, corn oil, and soybean oil), zinc stearate, ethyl oleate, ethyl laurate, agar, and mixtures thereof. Additional lubricants include, for example, a syloid silica gel (AEROSIL 200, manufactured by W.R. Grace Co. of Baltimore, Md., USA), a coagulated aerosol of synthetic silica (marketed by Deaussa Co. of Plano, Tex., USA), CAB-O-SIL (a pyrogenic silicon dioxide product sold by Cabot Co. of Boston, Mass., USA), and mixtures thereof.

D. Disintegrants

Disintegrants include, but are not limited to, agar-agar, alginic acid, calcium carbonate, microcrystalline cellulose, croscarmellose sodium, crospovidone, polacrilin potassium, sodium starch glycolate, potato or tapioca starch, other starches, pre-gelatinized starch, other starches, clays, other algins, other celluloses, gums, and mixtures thereof.

The tablets or capsules may optionally be coated by methods well known in the art. If binders and/or fillers are used with the compounds of the invention, they are typically formulated as about 50 to about 99 weight percent of the compound. In one aspect, about 0.5 to about 15 weight percent of disintegrant, and particularly about 1 to about 5 weight percent of disintegrant, may be used in combination with the compound. A lubricant may optionally be added, typically in an amount of less than about 1 weight percent of the compound. Techniques and pharmaceutically acceptable additives for making solid oral dosage forms are described in Marshall, SOLID ORAL DOSAGE FORMS, Modern Pharmaceutics (Banker and Rhodes, Eds.), 7:359-427 (1979). Other less typical formulations are known in the art.

Liquid preparations for oral administration may take the form of solutions, syrups or suspensions. Alternatively, the liquid preparations may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non-aqueous vehicles (e.g., almond oil, oily esters, ethyl alcohol or fractionated vegetable oils); and/or preservatives (e.g., methyl or propyl-p-hydroxybenzoates or sorbic acid). The preparations may also contain buffer salts, flavoring, coloring, perfuming and sweetening agents as appropriate. Preparations for oral administration may also be formulated to achieve controlled release of the compound. Oral formulations preferably contain 10% to 95% compound. In addition, the compounds of the present invention may be formulated for buccal administration in the form of tablets or lozenges formulated in a conventional manner. Other methods of oral delivery of compounds will be known to the skilled artisan and are within the scope of the invention.

Controlled-Release Administration

Controlled-release (or sustained-release) preparations may be formulated to extend the activity of the compound and reduce dosage frequency. Controlled-release preparations can also be used to effect the time of onset of action or other characteristics, such as blood levels of the compound, and consequently affect the occurrence of side effects.

Controlled-release preparations may be designed to initially release an amount of a compound that produces the desired therapeutic effect, and gradually and continually release other amounts of the compound to maintain the level of therapeutic effect over an extended period of time. In order to maintain a near-constant level of a compound in the body, the compound can be released from the dosage form at a rate that will replace the amount of compound being metabolized and/or excreted from the body. The controlled-release of a compound may be stimulated by various inducers, e.g., change in pH, change in temperature, enzymes, water, or other physiological conditions or molecules.

Controlled-release systems may include, for example, an infusion pump which may be used to administer the compound in a manner similar to that used for delivering insulin or chemotherapy to specific organs or tumors. Typically, using such a system, the compound is administered in combination with a biodegradable, biocompatible polymeric implant that releases the compound over a controlled period of time at a selected site. Examples of polymeric materials include polyanhydrides, polyorthoesters, polyglycolic acid, polylactic acid, polyethylene vinyl acetate, and copolymers and combinations thereof. In addition, a controlled release system can be placed in proximity of a therapeutic target, thus requiring only a fraction of a systemic dosage.

The compounds of the invention may be administered by other controlled-release means or delivery devices that are well known to those of ordinary skill in the art. These include, for example, hydropropylmethyl cellulose, other polymer matrices, gels, permeable membranes, osmotic systems, multilayer coatings, microparticles, liposomes, microspheres, or the like, or a combination of any of the above to provide the desired release profile in varying proportions. Other methods of controlled-release delivery of compounds will be known to the skilled artisan and are within the scope of the invention.

Inhalation Administration

The compound may also be administered directly to the lung by inhalation. For administration by inhalation, a compound may be conveniently delivered to the lung by a number of different devices. For example, a Metered Dose Inhaler ("MDI") which utilizes canisters that contain a suitable low boiling point propellant, e.g., dichlorodifluoromethane, trichlorofluoromethane, dichlorotetrafluoroethane, carbon dioxide or other suitable gas may be used to deliver a compound directly to the lung. MDI devices are available from a number of suppliers such as 3M Corporation, Aventis, Boehringer Ingleheim, Forest Laboratories, Glaxo-Wellcome, Schering Plough and Vectura.

Alternatively, a Dry Powder Inhaler (DPI) device may be used to administer a compound to the lung. DPI devices typically use a mechanism such as a burst of gas to create a cloud of dry powder inside a container, which may then be inhaled by the patient. DPI devices are also well known in the art and may be purchased from a number of vendors which include, for example, Fisons, Glaxo-Wellcome, Inhale Therapeutic Systems, ML Laboratories, Qdose and Vectura. A popular variation is the multiple dose DPI ("MDDPI") system, which allows for the delivery of more than one therapeutic dose. MDDPI devices are available from companies such as AstraZeneca, GlaxoWellcome, IVAX, Schering Plough, SkyePharma and Vectura. For example, capsules and cartridges of gelatin for use in an inhaler or insufflator may be formulated containing a powder mix of the compound and a suitable powder base such as lactose or starch for these systems.

Another type of device that may be used to deliver a compound to the lung is a liquid spray device supplied, for example, by Aradigm Corporation. Liquid spray systems use extremely small nozzle holes to aerosolize liquid compound formulations that may then be directly inhaled into the lung. For example, a nebulizer device may be used to deliver a compound to the lung. Nebulizers create aerosols from liquid compound formulations by using, for example, ultrasonic energy to form fine particles that may be readily inhaled. Examples of nebulizers include devices supplied by Sheffield/Systemic Pulmonary Delivery Ltd., Aventis and Batelle Pulmonary Therapeutics.

In another example, an electrohydrodynamic ("EHD") aerosol device may be used to deliver a compound to the lung. EHD aerosol devices use electrical energy to aerosolize liquid compound solutions or suspensions. The electrochemical properties of the compound formulation are important parameters to optimize when delivering this compound to the lung with an EHD aerosol device. Such optimization is routinely performed by one of skill in the art. Other methods of intrapulmonary delivery of compounds will be known to the skilled artisan and are within the scope of the invention.

Liquid compound formulations suitable for use with nebulizers and liquid spray devices and EHD aerosol devices will typically include the compound with a pharmaceutically acceptable carrier. In one exemplary embodiment, the pharmaceutically acceptable carrier is a liquid such as alcohol, water, polyethylene glycol or a perfluorocarbon. Optionally, another material may be added to alter the aerosol properties of the solution or suspension of the compound. For example, this material may be a liquid such as an alcohol, glycol, polyglycol or a fatty acid. Other methods of formulating liquid compound solutions or suspensions suitable for use in aerosol devices are known to those of skill in the art.

Depot Administration

The compound may also be formulated as a depot preparation. Such long-acting formulations may be administered by implantation (e.g., subcutaneously or intramuscularly) or by intramuscular injection. Accordingly, the compounds may be formulated with suitable polymeric or hydrophobic materials such as an emulsion in an acceptable oil or ion exchange resins, or as sparingly soluble derivatives such as a sparingly soluble salt. Other methods of depot delivery of compounds will be known to the skilled artisan and are within the scope of the invention.

Topical Administration

For topical application, the compound may be combined with a carrier so that an effective dosage is delivered, based on the desired activity ranging from an effective dosage, for example, of 1.0 μM to 1.0 mM. In one aspect of the invention, a topical compound can be applied to the skin. The carrier may be in the form of, for example, and not by way of limitation, an ointment, cream, gel, paste, foam, aerosol, suppository, pad or gelled stick.

A topical formulation may also consist of a therapeutically effective amount of the compound in an opthalmologically acceptable excipient such as buffered saline, mineral oil, vegetable oils such as corn or arachis oil, petroleum jelly, Miglyol 182, alcohol solutions, or liposomes or liposome-like products. Any of these compounds may also include preservatives, antioxidants, antibiotics, immunosuppressants, and other biologically or pharmaceutically effective agents which do not exert a detrimental effect on the compound. Other methods of topical delivery of compounds will be known to the skilled artisan and are within the scope of the invention.

Suppository Administration

The compound may also be formulated in rectal formulations such as suppositories or retention enemas containing conventional suppository bases such as cocoa butter or other glycerides and binders and carriers such as triglycerides, microcrystalline cellulose, gum tragacanth or gelatin. Suppositories can contain the compound in the range of 0.5% to 10% by weight. Other methods of suppository delivery of compounds will be known to the skilled artisan and are within the scope of the invention.

Other Systems of Administration

Various other delivery systems are known in the art and can be used to administer the compounds of the invention. Moreover, these and other delivery systems may be combined and/or modified to optimize the administration of the compounds of the present invention. Exemplary formulations using the compounds of the present invention are described below (the compounds of the present invention are indicated as the active ingredient, but those of skill in the art will recognize that pro-drugs and compound combinations are also meant to be encompassed by this term):

Formulation 1

Hard gelatin capsules are prepared using the following ingredients:

TABLE 4

| Ingredients | (mg/capsule) |
| --- | --- |
| Active Ingredient | 250.0 |
| Starch | 305.0 |
| Magnesium stearate | 5.0 |

The above ingredients are mixed and filled into hard gelatin capsules in 560 mg quantities.

Formulation 2

A tablet formula is prepared using the following ingredients:

TABLE 5

| Ingredients | (mg/tablet) |
| --- | --- |
| Active Ingredient | 250.0 |
| Cellulose, microcrystalline | 400.0 |
| Colloidal silicon dioxide | 10.0 |
| Stearic acid | 5.0 |

The components are blended and compressed to form tablets, each weighing 665 mg.

Formulation 3

A dry powder inhaler formulation is prepared containing the following components:

TABLE 6

| Ingredients | Weight % |
|---|---|
| Active ingredient | 5 |
| Lactose | 95 |

The active ingredient is mixed with the lactose and the mixture is added to a dry powder inhaling appliance.

Formulation 4

Tablets, each containing 60 mg of active ingredient, are prepared as follows:

TABLE 7

| Ingredients | milligrams |
|---|---|
| Active ingredient | 60.0 |
| Starch | 45.0 |
| Microcrystalline cellulose | 35.0 |
| Polyvinylpyrrolidone (as 10% solution in water) | 4.0 |
| Sodium carboxymethyl starch | 4.5 |
| Magnesium stearate | 0.5 |
| Talc | 1.0 |
| Total | 150.0 |

The active ingredient, starch and cellulose are passed through a No. 20 mesh U.S. sieve and mixed thoroughly. The solution of polyvinylpyrrolidone is mixed with the resultant powders which are then passed through a 16 mesh U.S. sieve. The granules as produced are dried at 50-60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 150 mg.

Formulation 5

Capsules, each containing 80 mg of active ingredient are made as follows:

TABLE 8

| Ingredients | milligrams |
|---|---|
| Active ingredient | 80.0 |
| Starch | 109.0 |
| Magnesium stearate | 1.0 |
| Total | 190.0 |

The active ingredient, cellulose, starch, and magnesium stearate are blended, passed through a No. 20 mesh U.S. sieve, and filled into hard gelatin capsules in 190 mg quantities.

Formulation 6

Suppositories, each containing 225 mg of active ingredient, are made as follows:

TABLE 9

| Ingredients | milligrams |
|---|---|
| Active Ingredient | 225 |
| Saturated fatty acid glycerides to | 2000 |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation 7

Suspensions, each containing 50 mg of active ingredient per 5.0 ml dose are made as follows:

TABLE 10

| Ingredients | milligrams |
|---|---|
| Active ingredient | 50.0 mg |
| Xanthan gum | 4.0 mg |
| Sodium carboxymethyl cellulose | (11%) |
| Microcrystalline cellulose | (89%) 50.0 mg |
| Sucrose | 1.75 g |
| Sodium benzoate | 10.0 mg |
| Flavor | q.v. |
| Color | q.v. |
| Purified water to | 5.0 ml |

The active ingredient, sucrose and xanthan gum are blended, passed through a No. 10 mesh U.S. sieve, and mixed with a previously made solution of the microcrystalline cellulose and sodium carboxymethyl cellulose in water. The sodium benzoate, flavor, and color are diluted with some of the water and added with stirring. Sufficient water is then added to produce the required volume.

Formulation 8

Capsules, each containing 150 mg of active ingredient, are made as follows:

TABLE 11

| Ingredients | milligrams |
|---|---|
| Active ingredient | 150.0 |
| Starch | 407.0 |
| Magnesium stearate | 3.0 |
| Total | 560.0 |

The active ingredient, cellulose, starch, and magnesium stearate are blended, passed through a No. 20 mesh U.S. sieve, and filled into hard gelatin capsules in 560 mg quantities.

The invention also provides a method for treating metabolic syndrome, the method comprising administering a therapeutically effectively amount of an insulin sensitizing compound to a patient in need thereof. In various aspects of the invention, the insulin sensitizing compound can be identified by a method described above. In some aspects, the metabolic syndrome can be insulin resistance and/or Type 2 diabetes mellitus. In some aspects, the insulin sensitizing compound can be an antibody having specificity for GRK2 as described above. In various aspects, the insulin sensitizing compound can be selected from the group consisting of a ribozyme, antisense compound, triplex-forming molecule, siRNA, and aptamer, wherein the insulin sensitizing compound has specificity for GRK2 as described above. In particular, the siRNA can comprise the sequence of SEQ ID NO: 1. In various aspects, the compound can be delivered to the subject in combination with an agent selected from the group consisting of a pharmaceutically acceptable carrier, a controlled-release component, a pharmaceutically acceptable salt, and any combination thereof. In some aspects, the compound is formulated as a pro-drug. In various aspects, the compound can be administered by a method selected from the group consisting of parenteral administration, oral administration, controlled-release administration, inhalation administration, depot administration, topical administration, suppository administration, and any combination thereof.

Prophylactic Methods

The invention provides a method for preventing, in a subject, a disease or condition associated with an aberrant GRK2 expression or activity, by administering an agent that modulates GRK2 expression or at least one GRK2 activity. Subjects at risk for a disease that is caused or contributed to by aberrant GRK2 expression or activity can be identified by, for example, any or a combination of diagnostic or prognostic assays. Administration of a prophylactic agent can occur prior to the manifestation of symptoms characteristic of the GRK2 aberrancy, such that a disease or disorder is prevented or, alternatively, delayed in its progression. Depending on the type of GRK2 aberrancy, for example, a GRK2 agonist or GRK2 antagonist can be used to treat the subject. The appropriate agent can be determined based on screening assays.

Therapeutic Methods

Another aspect of the invention pertains to methods of modulating GRK2 expression or activity for therapeutic purposes. The modulatory method of the invention involves contacting a cell with an agent that modulates one or more of the activities of GRK2 activity associated with the cell. An agent that modulates GRK2 activity can be a nucleic acid or a protein, a naturally occurring cognate ligand of GRK2, a peptide, a GRK2 peptidomimetic, or other small molecule. In an embodiment, the agent inhibits GRK2 activity. Examples of inhibitory agents include antisense GRK2 nucleic acids and anti-GRK2 Abs. Modulatory methods can be performed in vitro (e.g., by culturing the cell with the agent) or, alternatively, in vivo (e.g., by administering the agent to a subject). As such, the invention provides methods of treating an individual afflicted with a disease or disorder characterized by aberrant expression or activity of a GRK2 or nucleic acid molecule. In one embodiment, the method involves administering an agent (e.g., an agent identified by a screening assay), or combination of agents that modulates (e.g., up-regulates or down-regulates) GRK2 expression or activity. In another embodiment, the method involves administering a GRK2 or nucleic acid molecule as therapy to compensate for increased or aberrant GRK2 expression or activity.

Inhibition of GRK2 activity is desirable in situations in which GRK2 is abnormally up-regulated and/or in which increased GRK2 activity is likely to have a detrimental effect, such as in metabolic syndrome.

Determination of the Biological Effect of the Therapeutic

Suitable in vitro or in vivo assays can be performed to determine the effect of a specific therapeutic and whether its administration is indicated for treatment of the affected tissue. In various specific embodiments, in vitro assays may be performed with representative cells of the type(s) involved in the patient's disorder, to determine if a given therapeutic exerts the desired effect upon the cell type(s). Modalities for use in therapy may be tested in suitable animal model systems including, but not limited to rats, mice, chicken, cows, monkeys, rabbits, and the like, prior to testing in human subjects. Similarly, for in vivo testing, any of the animal model system known in the art may be used prior to administration to human subjects.

Prophylactic and Therapeutic Uses of Compositions

GRK2 nucleic acids and proteins are useful in potential prophylactic and therapeutic applications implicated in a variety of disorders including, but not limited to, insulin resistance and Type 2 diabetes mellitus. As an example, a cDNA encoding GRK2 may be useful in gene therapy, and the protein may be useful when administered to a subject in need thereof. By way of non-limiting example, the compositions of the invention will have efficacy for treatment of patients suffering from metabolic syndrome.

GRK2 nucleic acids, or fragments thereof, may also be useful in diagnostic applications, wherein the presence or amount of the nucleic acid or the protein is to be assessed. These materials are useful, e.g., in the generation of Abs that immunospecifically bind to the novel substances of the invention for use in therapeutic or diagnostic methods.

Methods of Treatment

The invention provides for both prophylactic and therapeutic methods of treating a subject at risk of (or susceptible to) a disorder or having a disorder associated with aberrant GRK2 expression or activity. Examples include disorders in which GRK2 is stimulated. Examples of such disorders and diseases include Type 2 diabetes mellitus; and those further described, infra.

Treatment of Diseases and Disorders

Diseases and disorders that are characterized by increased GRK2 levels or biological activity (such as metabolic syndrome) may be treated with therapeutics that antagonize (i.e., reduce or inhibit) activity. Antagonists may be administered in a therapeutic or prophylactic manner. Therapeutics that may be used include: (1) GRK2 peptides, or analogs, derivatives, fragments or homologues thereof; (2) Abs to a GRK2 peptide; (3) GRK2 nucleic acids; (4) administration of antisense nucleic acid and nucleic acids that are "dysfunctional" (i.e., due to a heterologous insertion within the coding sequences) that are used to eliminate endogenous function of by homologous recombination; or (5) modulators (i.e., inhibitors, agonists and antagonists, including additional peptide mimetic of the invention or Abs specific to GRK2) that alter the interaction between GRK2 and its binding partner, and other antagonists described herein such as siRNAs.

Diseases and disorders that are characterized by decreased GRK2 levels or biological activity may be treated with therapeutics that increase (i.e., are agonists to) activity. Therapeutics that upregulate activity may be administered therapeutically or prophylactically. Therapeutics that may be used include peptides, or analogs, derivatives, fragments or homologues thereof; or an agonist that increases bioavailability.

Increased or decreased levels can be readily detected by quantifying peptide and/or RNA, by obtaining a patient tissue sample (e.g., from biopsy tissue) and assaying in vitro for RNA or peptide levels, structure and/or activity of the expressed peptides (or GRK2 mRNAs). Methods include, but are not limited to, immunoassays (e.g., by Western blot analysis, immunoprecipitation followed by sodium dodecyl sulfate (SDS) polyacrylamide gel electrophoresis, immunocytochemistry, etc.) and/or hybridization assays to detect expression of mRNAs (e.g., Northern assays, dot blots, in situ hybridization, and the like).

The invention also provides a method for expressing a siRNA specific to a GRK2 gene in a cell in vitro or in vivo, comprising: providing an expression vector encoding a siRNA specific to a GRK2 gene; introducing the vector into a cell in vitro or in vivo; and maintaining the cell in vitro or in vivo under conditions permitting expression of the siRNA in the cell as described herein.

The invention also provides a method for identifying a subject having or susceptible to acquiring metabolic syndrome, the method comprising detecting a level of GRK2 activity in the subject and comparing the subject GRK2 activity level to a predetermined normal standard, wherein a GRK2 activity level above the normal standard indicates that the subject has or is susceptible to acquiring metabolic syndrome.

Detection Assays

Portions or fragments of GRK2 cDNA sequences identified herein (and the complete GRK2 gene sequences) are useful in themselves. By way of non-limiting example, these sequences can be used to: (1) identify an individual from a minute biological sample (tissue typing); and (2) aid in forensic identification of a biological sample.

The GRK2 sequences of the invention can be used to identify individuals from minute biological samples. In this technique, an individual's genomic DNA is digested with one or more restriction enzymes and probed on a Southern blot to yield unique bands. The sequences of the invention are useful as additional DNA markers for "restriction fragment length polymorphisms" (RFLP).

Furthermore, the GRK2 sequences can be used to determine the actual base-by-base DNA sequence of targeted portions of an individual's genome. GRK2 sequences can be used to prepare two PCR primers from the 5'- and 3'-termini of the sequences that can then be used to amplify an the corresponding sequences from an individual's genome and then sequence the amplified fragment.

Panels of corresponding DNA sequences from individuals can provide unique individual identifications, as each individual will have a unique set of such DNA sequences due to allelic differences. The sequences of the invention can be used to obtain such identification sequences from individuals and from tissue. The GRK2 sequences of the invention uniquely represent portions of an individual's genome. Allelic variation occurs to some degree in the coding regions of these sequences, and to a greater degree in the noncoding regions. The allelic variation between individual humans occurs with a frequency of about once ever 500 bases. Much of the allelic variation is due to single nucleotide polymorphisms (SNPs), which include RFLPs.

Each of the sequences described herein can, to some degree, be used as a standard against which DNA from an individual can be compared for identification purposes. Because greater numbers of polymorphisms occur in noncoding regions, fewer sequences are necessary to differentiate individuals. Noncoding sequences can positively identify individuals with a panel of 10 to 1,000 primers that each yield a noncoding amplified sequence of 100 bases. If predicted coding sequences, such as those in SEQ ID NOs: 1 and 2 are used, a more appropriate number of primers for positive individual identification would be 500-2,000.

Predictive Medicine

The invention also pertains to the field of predictive medicine in which diagnostic assays, prognostic assays, pharmacogenomics, and monitoring clinical trials are used for prognostic (predictive) purposes to treat an individual prophylactically. Accordingly, one aspect of the invention relates to diagnostic assays for determining GRK2 and/or nucleic acid expression as well as GRK2 activity, in the context of a biological sample (e.g., blood, serum, cells, tissue) to determine whether an individual is afflicted with a disease or disorder, or is at risk of developing a disorder, associated with aberrant GRK2 expression or activity, including Type 2 diabetes mellitus. The invention also provides for prognostic (or predictive) assays for determining whether an individual is at risk of developing a disorder associated with GRK2, nucleic acid expression or activity. For example, mutations in GRK2 can be assayed in a biological sample. Such assays can be used for prognostic or predictive purpose to prophylactically treat an individual prior to the onset of a disorder characterized by or associated with GRK2, nucleic acid expression, or biological activity.

Another aspect of the invention provides methods for determining GRK2 activity, or nucleic acid expression, in an individual to select appropriate therapeutic or prophylactic agents for that individual (referred to herein as "pharmacogenomics"). Pharmacogenomics allows for the selection of modalities (e.g., drugs, foods) for therapeutic or prophylactic treatment of an individual based on the individual's genotype (e.g., the individual's genotype to determine the individual's ability to respond to a particular agent). Another aspect of the invention pertains to monitoring the influence of modalities (e.g., drugs, foods) on the expression or activity of GRK2 in clinical trials.

Diagnostic Assays

An exemplary method for detecting the presence or absence of GRK2 in a biological sample involves obtaining a biological sample from a subject and contacting the biological sample with a compound or an agent capable of detecting GRK2 or GRK2 nucleic acid (e.g., mRNA, genomic DNA) such that the presence of GRK2 is confirmed in the sample. An agent for detecting GRK2 mRNA or genomic DNA is a labeled nucleic acid probe that can hybridize to GRK2 mRNA or genomic DNA. The nucleic acid probe can be, for example, a full-length GRK2 nucleic acid, such as the nucleic acids of SEQ ID NOs: 1 and 2, or portions thereof, such as an oligonucleotide of at least 15, 30, 50, 100, 250 or 500 nucleotides in length and sufficient to specifically hybridize under stringent conditions to GRK2 mRNA or genomic DNA.

An agent for detecting GRK2 polypeptide is an antibody capable of binding to GRK2, preferably an antibody with a detectable label. Abs can be polyclonal, or more preferably, monoclonal. An intact antibody, or a fragment (e.g., $F_{ab}$ or $F(ab')_2$) can be used. A labeled probe or antibody is coupled (i.e., physically linking) to a detectable substance, as well as indirect detection of the probe or antibody by reactivity with another reagent that is directly labeled. Examples of indirect labeling include detection of a primary antibody using a fluorescently labeled secondary antibody and end-labeling of a DNA probe with biotin such that it can be detected with fluorescently-labeled streptavidin. The term "biological sample" includes tissues, cells and biological fluids isolated from a subject, as well as tissues, cells and fluids present within a subject. The detection method of the invention can be used to detect GRK2 mRNA, protein, or genomic DNA in a biological sample in vitro as well as in vivo. For example, in vitro techniques for detection of GRK2 mRNA include Northern hybridizations and in situ hybridizations. In vitro techniques for detection of GRK2 polypeptide include enzyme linked immunosorbent assays (ELISAs), Western blots, immunoprecipitations, and immunofluorescence. In vitro techniques for detection of GRK2 genomic DNA include Southern hybridizations and fluorescence in situ hybridization (FISH). Furthermore, in vivo techniques for detecting GRK2 include introducing into a subject a labeled anti-GRK2 antibody. For example, the antibody can be labeled with a radioactive marker whose presence and location in a subject can be detected by standard imaging techniques.

In one embodiment, the biological sample from the subject contains protein molecules, and/or mRNA molecules, and/or genomic DNA molecules. A preferred biological sample is blood. In another embodiment, the methods further involve obtaining a biological sample from a subject to provide a control, contacting the sample with a compound or agent to detect GRK2, mRNA, or genomic DNA, and comparing the presence of GRK2, mRNA or genomic DNA in the control sample with the presence of GRK2, mRNA or genomic DNA in the test sample.

The invention also encompasses kits for detecting GRK2 in a biological sample. For example, the kit can comprise: a labeled compound or agent capable of detecting GRK2 or GRK2 mRNA in a sample; reagent and/or equipment for determining the amount of GRK2 in the sample; and reagent and/or equipment for comparing the amount of GRK2 in the sample with a standard. The compound or agent can be packaged in a suitable container. The kit can further comprise instructions for using the kit to detect GRK2 or nucleic acid.

Prognostic Assays

The diagnostic methods described herein can furthermore be utilized to identify subjects having or at risk of developing a disease or disorder associated with aberrant GRK2 expression or activity. For example, the assays described herein, can be used to identify a subject having or at risk of developing a disorder associated with GRK2, nucleic acid expression or activity. Alternatively, the prognostic assays can be used to identify a subject having or at risk for developing a disease or disorder. The invention provides a method for identifying a disease or disorder associated with aberrant GRK2 expression or activity in which a test sample is obtained from a subject and GRK2 or nucleic acid (e.g., mRNA, genomic DNA) is detected. A test sample is a biological sample obtained from a subject. For example, a test sample can be a biological fluid (e.g., serum), cell sample, or tissue.

Prognostic assays can be used to determine whether a subject can be administered a modality (e.g., an agonist, antagonist, peptidomimetic, protein, peptide, nucleic acid, small molecule, food, etc.) to treat a disease or disorder associated with aberrant GRK2 expression or activity. Such methods can be used to determine whether a subject can be effectively treated with an agent for a disorder. The invention provides methods for determining whether a subject can be effectively treated with an agent for a disorder associated with aberrant GRK2 expression or activity in which a test sample is obtained and GRK2 or nucleic acid is detected (e.g., where the presence of GRK2 or nucleic acid is diagnostic for a subject that can be administered the agent to treat a disorder associated with aberrant GRK2 expression or activity).

The methods of the invention can also be used to detect genetic lesions in a GRK2 to determine if a subject with the genetic lesion is at risk for a disorder. Methods include detecting, in a sample from the subject, the presence or absence of a genetic lesion characterized by at an alteration affecting the integrity of a gene encoding a GRK2 polypeptide, or the misexpression of GRK2. Such genetic lesions can be detected by ascertaining: (1) a deletion of one or more nucleotides from GRK2; (2) an addition of one or more nucleotides to GRK2; (3) a substitution of one or more nucleotides in GRK2, (4) a chromosomal rearrangement of a GRK2 gene; (5) an alteration in the level of a GRK2 mRNA transcripts, (6) aberrant modification of a GRK2, such as a change genomic DNA methylation, (7) the presence of a non-wild-type splicing pattern of a GRK2 mRNA transcript, (8) a non-wild-type level of GRK2, (9) allelic loss of GRK2, and/or (10) inappropriate post-translational modification of GRK2 polypeptide. There are a large number of known assay techniques that can be used to detect lesions in GRK2. Any biological sample containing nucleated cells may be used.

In certain embodiments, lesion detection may use a probe/ primer in a polymerase chain reaction (PCR) (such as anchor PCR or rapid amplification of cDNA ends (RACE) PCR, or, alternatively, in a ligation chain reaction (LCR). This method may include collecting a sample from a patient, isolating nucleic acids from the sample, contacting the nucleic acids with one or more primers that specifically hybridize to GRK2 under conditions such that hybridization and amplification of the GRK2 (if present) occurs, and detecting the presence or absence of an amplification product, or detecting the size of the amplification product and comparing the length to a control sample. It is anticipated that PCR and/or LCR may be desirable to use as a preliminary amplification step in conjunction with any of the techniques used for detecting mutations described herein.

Alternative amplification methods include: self sustained sequence replication, transcriptional amplification system; Qβ Replicase, or any other nucleic acid amplification method, followed by the detection of the amplified molecules using techniques well known to those of skill in the art. These detection schemes are especially useful for the detection of nucleic acid molecules present in low abundance and are known to those of skill in the art.

Mutations in GRK2 from a sample can be identified by alterations in restriction enzyme cleavage patterns. For example, sample and control DNA is isolated, amplified (optionally), digested with one or more restriction endonucleases, and fragment length sizes are determined by gel electrophoresis and compared. Differences in fragment length sizes between sample and control DNA indicates mutations in the sample DNA. Moreover, the use of sequence specific ribozymes can be used to score for the presence of specific mutations by development or loss of a ribozyme cleavage site.

Hybridizing a sample and control nucleic acids, e.g., DNA or RNA, to high-density arrays containing hundreds or thousands of oligonucleotides probes, can identify genetic mutations in GRK2. For example, genetic mutations in GRK2 can be identified in two-dimensional arrays containing light-generated DNA probes. Briefly, a first hybridization array of probes can be used to scan through long stretches of DNA in a sample and control to identify base changes between the sequences by making linear arrays of sequential overlapping probes. This step allows the identification of point mutations. This is followed by a second hybridization array that allows the characterization of specific mutations by using smaller, specialized probe arrays complementary to all variants or mutations detected. Each mutation array is composed of parallel probe sets, one complementary to the wild-type gene and the other complementary to the mutant gene.

In yet another embodiment, any of a variety of sequencing reactions known in the art can be used to directly sequence the GRK2 and detect mutations by comparing the sequence of the sample GRK2- with the corresponding wild-type (control) sequence. Any of a variety of automated sequencing procedures can be used when performing diagnostic assays including sequencing by mass spectrometry.

Other methods for detecting mutations in the GRK2 include those in which protection from cleavage agents is used to detect mismatched bases in RNA/RNA or RNA/DNA heteroduplexes. In general, the technique of "mismatch cleavage" starts by providing heteroduplexes formed by hybridizing (labeled) RNA or DNA containing the wild-type GRK2 sequence with potentially mutant RNA or DNA obtained from a sample. The double-stranded duplexes are treated with an agent that cleaves single-stranded regions of the duplex such as those that arise from base pair mismatches between the control and sample strands. For instance, RNA/ DNA duplexes can be treated with RNase and DNA/DNA hybrids treated with $S_1$ nuclease to enzymatically digest the mismatched regions. In other embodiments, either DNA/ DNA or RNA/DNA duplexes can be treated with hydroxylamine or osmium tetroxide and with piperidine in order to digest mismatched regions. The digested material is then separated by size on denaturing polyacrylamide gels to determine the mutation site. The control DNA or RNA can be labeled for detection.

Mismatch cleavage reactions may employ one or more proteins that recognize mismatched base pairs in double-stranded DNA (DNA mismatch repair) in defined systems for detecting and mapping point mutations in GRK2 cDNAs obtained from samples of cells. For example, the mutY enzyme of *E. coli* cleaves A at G/A mismatches and the thymidine DNA glycosylase from HeLa cells cleaves T at G/T mismatches. According to an exemplary embodiment, a probe based on a wild-type GRK2 sequence is hybridized to a cDNA or other DNA product from a test cell(s). The duplex is treated with a DNA mismatch repair enzyme, and the cleavage products, if any, can be detected from electrophoresis protocols or the like.

Electrophoretic mobility alterations can be used to identify mutations in GRK2. For example, single strand conformation polymorphism (SSCP) may be used to detect differences in electrophoretic mobility between mutant and wild type nucleic acids. Single-stranded DNA fragments of sample and control GRK2 nucleic acids are denatured and then renatured. The secondary structure of single-stranded nucleic acids varies according to sequence; the resulting alteration in electrophoretic mobility allows detection of even a single base change. The DNA fragments may be labeled or detected with labeled probes. The sensitivity of the assay may be enhanced by using RNA (rather than DNA), in which the secondary structure is more sensitive to a sequence changes. The subject method may use heteroduplex analysis to separate double stranded heteroduplex molecules on the basis of changes in electrophoretic mobility.

The migration of mutant or wild-type fragments can be assayed using denaturing gradient gel electrophoresis (DGGE). In DGGE, DNA is modified to prevent complete denaturation, for example by adding a GC clamp of approximately 40 bp of high-melting GC-rich DNA by PCR. A temperature gradient may also be used in place of a denaturing gradient to identify differences in the mobility of control and sample DNA.

Examples of other techniques for detecting point mutations include, but are not limited to, selective oligonucleotide hybridization, selective amplification, or selective primer extension. For example, oligonucleotide primers may be prepared in which the known mutation is placed centrally and then hybridized to target DNA under conditions that permit hybridization only if a perfect match is found. Such allele-specific oligonucleotides are hybridized to PCR-amplified target DNA or a number of different mutations when the oligonucleotides are attached to the hybridizing membrane and hybridized with labeled target DNA.

Alternatively, allele specific amplification technology that depends on selective PCR amplification may be used. Oligonucleotide primers for specific amplifications may carry the mutation of interest in the center of the molecule (so that amplification depends on differential hybridization) or at the extreme 3'-terminus of one primer where, under appropriate conditions, mismatch can prevent, or reduce polymerase extension. Novel restriction site in the region of the mutation may be introduced to create cleavage-based detection. Certain amplification may also be performed using Taq ligase for amplification. In such cases, ligation occurs only if there is a perfect match at the 3'-terminus of the 5' sequence, allowing detection of a known mutation by scoring for amplification.

The described methods may be performed, for example, by using pre-packaged kits comprising at least one probe (nucleic acid or antibody) that may be conveniently used, for example, in clinical settings to diagnose patients exhibiting symptoms or family history of a disease or illness involving GRK2.

Furthermore, any cell type or tissue in which GRK2 is expressed may be utilized in the prognostic assays described herein.

Pharmacogenomics

Agents, or modulators that have a stimulatory or inhibitory effect on GRK2 activity or expression, as identified by a screening assay can be administered to individuals to treat, prophylactically or therapeutically, disorders. In conjunction with such treatment, the pharmacogenomics (i.e., the study of the relationship between a subject's genotype and the subject's response to a foreign modality, such as a food, compound or drug) may be considered. Metabolic differences of therapeutics can lead to severe toxicity or therapeutic failure by altering the relation between dose and blood concentration of the pharmacologically active drug. Thus, the pharmacogenomics of the individual permits the selection of effective agents (e.g., drugs) for prophylactic or therapeutic treatments based on a consideration of the individual's genotype. Pharmacogenomics can further be used to determine appropriate dosages and therapeutic regimens. Accordingly, the activity of GRK2, expression of GRK2 nucleic acid, or GRK2 mutation(s) in an individual can be determined to guide the selection of appropriate agent(s) for therapeutic or prophylactic treatment.

Pharmacogenomics deals with clinically significant hereditary variations in the response to modalities due to altered modality disposition and abnormal action in affected persons. In general, two pharmacogenetic conditions can be differentiated: (1) genetic conditions transmitted as a single factor altering the interaction of a modality with the body (altered drug action) or (2) genetic conditions transmitted as single factors altering the way the body acts on a modality (altered drug metabolism). These pharmacogenetic conditions can occur either as rare defects or as nucleic acid polymorphisms. For example, glucose-6-phosphate dehydrogenase (G6PD) deficiency is a common inherited enzymopathy in which the main clinical complication is hemolysis after ingestion of oxidant drugs (anti-malarials, sulfonamides, analgesics, nitrofurans) and consumption of fava beans.

As an illustrative embodiment, the activity of drug metabolizing enzymes is a major determinant of both the intensity and duration of drug action. The discovery of genetic polymorphisms of drug metabolizing enzymes (e.g., N-acetyl-transferase 2 (NAT 2) and cytochrome P450 enzymes CYP2D6 and CYP2C19) explains the phenomena of some patients who show exaggerated drug response and/or serious toxicity after taking the standard and safe dose of a drug. These polymorphisms are expressed in two phenotypes in the population, the extensive metabolizer (EM) and poor metabolizer (PM). The prevalence of PM is different among different populations. For example, the CYP2D6 gene is highly polymorphic and several mutations have been identified in PM, which all lead to the absence of functional CYP2D6. Poor metabolizers due to mutant CYP2D6 and CYP2C19 frequently experience exaggerated drug responses and side effects when they receive standard doses. If a metabolite is the active therapeutic moiety, PM shows no therapeutic response, as demonstrated for the analgesic effect of codeine mediated by its CYP2D6-formed metabolite morphine. At the other extreme are the so-called ultra-rapid metabolizers who are unresponsive to standard doses. Recently, the molecular basis of ultra-rapid metabolism has been identified to be due to CYP2D6 gene amplification.

The activity of GRK2, expression of GRK2 nucleic acid, or mutation content of GRK2 in an individual can be determined to select appropriate agent(s) for therapeutic or prophylactic treatment of the individual. In addition, pharmacogenetic studies can be used to apply genotyping of polymorphic alleles encoding drug-metabolizing enzymes to the identification of an individual's drug responsiveness phenotype. This knowledge, when applied to dosing or drug selection, can avoid adverse reactions or therapeutic failure and thus enhance therapeutic or prophylactic efficiency when treating a subject with a GRK2 modulator, such as a modulator identified by one of the described exemplary screening assays.

In another aspect of the present invention, a method for treating a cancer or an autoimmune disease is provided comprising decreasing the activity of GRK2. In various aspects, decreasing the activity can comprise decreasing the expression of GRK2. In various aspects, decreasing the expression comprises transforming a cell to express a polynucleotide anti-sense to at least a portion of an endogenous polynucleotide encoding GRK2 as described above. In various aspects, decreasing the activity comprises inhibiting, preventing, or reversing at least one activity of GRK2 as described above. In various other aspects, decreasing the activity can comprise transforming a cell to express an aptamer to GRK2 as described above. In various aspects, decreasing the activity can comprise introducing into a cell an aptamer to GRK2 as described above. In a further aspect, decreasing the activity can comprise administering to a cell an antibody that selectively binds GRK2 as described above.

The invention further provides a purified antibody that binds specifically to the RGS domain of GRK2 as described above.

In addition, the invention provides a transgenic non-human animal whose somatic and germ cells comprise a disrupted GRK2 gene, the disruption being sufficient to inhibit the binding of GRK2 to Gαq/11, said disrupted gene being introduced into the non-human animal or an ancestor of the non-human animal at an embryonic stage, wherein the non-human animal, if homozygous for the disrupted GRK2 gene, is infertile. In some aspects, the non-human animal can be selected from the group consisting of a mouse, pig, rat, hamster, goat, cow, and chicken.

Transgenic GRK2 Animals

"Transgenic animals" are non-human animals, preferably mammals, more preferably a rodents such as rats or mice, in which one or more of the cells include a transgene. Other transgenic animals include primates, sheep, dogs, cows, goats, chickens, amphibians, etc. A "transgene" is exogenous DNA that is integrated into the genome of a cell from which a transgenic animal develops, and that remains in the genome of the mature animal. Transgenes preferably direct the expression of an encoded gene product in one or more cell types or tissues of the transgenic animal with the purpose of preventing expression of a naturally encoded gene product in one or more cell types or tissues (a "knockout" transgenic animal; see the Examples), or serving as a marker or indicator of an integration, chromosomal location, or region of recombination (e.g., cre/loxP mice). A "homologous recombinant animal" is a non-human animal, such as a rodent, in which endogenous GRK2 has been altered by an exogenous DNA molecule that recombines homologously with endogenous GRK2 in a (e.g., embryonic) cell prior to development the animal. Host cells with exogenous GRK2 can be used to produce non-human transgenic animals, such as fertilized oocytes or embryonic stem cells into which GRK2-coding sequences have been introduced. Such host cells can then be used to create non-human transgenic animals or homologous recombinant animals.

Approaches to Transgenic Animal Production

A transgenic animal can be created by introducing GRK2 into the male pronuclei of a fertilized oocyte (e.g., by microinjection, retroviral infection) and allowing the oocyte to develop in a pseudopregnant female foster animal (pffa). The GRK2 sequences (SEQ ID NOs: 1 or 2) can be introduced as a transgene into the genome of a non-human animal. Alternatively, a homologue of GRK2 can be used as a transgene. Intronic sequences and polyadenylation signals can also be included in the transgene to increase transgene expression. Tissue-specific regulatory sequences can be operably-linked to the GRK2 transgene to direct expression of GRK2 to particular cells. Methods for generating transgenic animals via embryo manipulation and microinjection, particularly animals such as mice, have become conventional in the art. Other non-mice transgenic animals may be made by similar methods. A transgenic founder animal, which can be used to breed additional transgenic animals, can be identified based upon the presence of the transgene in its genome and/or expression of the transgene mRNA in tissues or cells of the animals. Transgenic (e.g., GRK2) animals can be bred to other transgenic animals carrying other transgenes.

Vectors for Transgenic Animal Production

To create a homologous recombinant animal, a vector containing at least a portion of GRK2 into which a deletion, addition or substitution has been introduced to thereby alter, e.g., functionally disrupt, GRK2. GRK2 can be a human gene (SEQ ID NO: 2), or other GRK2 homologue (e.g., SEQ ID NO: 1). In one approach, a knockout vector functionally disrupts the endogenous GRK2 gene upon homologous recombination, and thus a non-functional GRK2 protein, if any, is expressed.

Alternatively, the vector can be designed such that, upon homologous recombination, the endogenous GRK2 is mutated or otherwise altered but still encodes functional protein (e.g., the upstream regulatory region can be altered to thereby alter the expression of endogenous GRK2). In this type of homologous recombination vector, the altered portion of the GRK2 is flanked at its 5'- and 3'-termini by additional nucleic acid of the GRK2 to allow for homologous recombination to occur between the exogenous GRK2 carried by the vector and an endogenous GRK2 in an embryonic stem cell. The additional flanking GRK2 nucleic acid is sufficient to engender homologous recombination with endogenous GRK2. Typically, several kilobases of flanking DNA (both at the 5'- and 3'-termini) are included in the vector. The vector is then introduced into an embryonic stem cell line (e.g., by electroporation), and cells in which the introduced GRK2 has homologously-recombined with the endogenous GRK2 are selected.

Introduction of GRK2 Transgene Cells During Development

Selected cells are then injected into a blastocyst of an animal (e.g., a mouse) to form aggregation chimeras. A chimeric embryo can then be implanted into a suitable pffa and the embryo brought to term. Progeny harboring the homologously-recombined DNA in their germ cells can be used to breed animals in which all cells of the animal contain the homologously-recombined DNA by germline transmission of the transgene. Methods for constructing homologous recombination vectors and homologous recombinant animals are described.

Alternatively, transgenic animals that contain selected systems that allow for regulated expression of the transgene can be produced. An example of such a system is the cre/loxP recombinase system of bacteriophage P1. Another recombinase system is the FLP recombinase system of *Saccharomyces cerevisiae*. If a cre/loxP recombinase system is used to regulate expression of the transgene, animals containing transgenes encoding both the Cre recombinase and a selected protein are required. Such animals can be produced as "double" transgenic animals, by mating an animal containing a transgene encoding a selected protein to another containing a transgene encoding a recombinase.

Clones of transgenic animals can also be produced. In brief, a cell from a transgenic animal can be isolated and induced to exit the growth cycle and enter G0 phase. The quiescent cell can then be fused to an enucleated oocyte from an animal of the same species from which the quiescent cell is isolated. The reconstructed oocyte is then cultured to develop to a morula or blastocyte and then transferred to a pffa. The offspring borne of this female foster animal will be a clone of the "parent" transgenic animal.

The invention also provides an expression vector comprising a nucleic acid encoding the ribonucleotide sequence of SEQ ID NO: 1, wherein the nucleic acid is operably linked to an expression control sequence. The invention further provides a cultured cell comprising the vector above. Further provided is a cultured cell comprising the nucleic acid above. In addition, the invention provides a cultured cell comprising the ribonucleic acid of SEQ ID NO: 1.

Vectors

Vectors are tools used to shuttle DNA between host cells or as a means to express a nucleotide sequence. Some vectors function only in prokaryotes, while others function in both prokaryotes and eukaryotes, enabling large-scale DNA preparation from prokaryotes for expression in eukaryotes. Inserting the DNA of interest, such as GRK2 nucleotide sequence or a fragment, is accomplished by ligation techniques and/or mating protocols well known to the skilled artisan. Such DNA is inserted such that its integration does not disrupt any necessary components of the vector. In the case of vectors that are used to express the inserted DNA protein, the introduced DNA is operably-linked to the vector elements that govern its transcription and translation.

Vectors can be divided into two general classes: Cloning vectors are replicating plasmid or phage with regions that are non-essential for propagation in an appropriate host cell, and into which foreign DNA can be inserted; the foreign DNA is replicated and propagated as if it were a component of the vector. An expression vector (such as a plasmid, yeast, or animal virus genome) is used to introduce foreign genetic material into a host cell or tissue in order to transcribe and translate the foreign DNA. In expression vectors, the introduced DNA is operably-linked to elements, such as promoters, that signal to the host cell to transcribe the inserted DNA. Some promoters are exceptionally useful, such as inducible promoters that control gene transcription in response to specific factors. Operably-linking GRK2 or anti-sense construct to an inducible promoter can control the expression of GRK2 or fragments, or anti-sense constructs. Examples of classic inducible promoters include those that are responsive to α-interferon, heat-shock, heavy metal ions, and steroids such as glucocorticoids and tetracycline. Other desirable inducible promoters include those that are not endogenous to the cells in which the construct is being introduced, but, however, is responsive in those cells when the induction agent is exogenously supplied.

Vectors have many difference manifestations. A "plasmid" is a circular double stranded DNA molecule into which additional DNA segments can be introduced. Viral vectors can accept additional DNA segments into the viral genome. Certain vectors are capable of autonomous replication in a host cell (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. In general, useful expression vectors are often plasmids. However, other forms of expression vectors, such as viral vectors (e.g., replication defective retroviruses, adenoviruses and adeno-associated viruses) are contemplated.

Recombinant expression vectors that comprise GRK2 (or fragments) regulate GRK2 transcription by exploiting one or more host cell-responsive (or that can be manipulated in vitro) regulatory sequences that is operably-linked to GRK2. "Operably-linked" indicates that a nucleotide sequence of interest is linked to regulatory sequences such that expression of the nucleotide sequence is achieved.

Vectors can be introduced in a variety of organisms and/or cells (Table 12). Alternatively, the vectors can be transcribed and translated in vitro, for example using T7 promoter regulatory sequences and T7 polymerase.

TABLE 12

Examples of hosts for cloning or expression

| Organisms | Examples |
|---|---|
| Prokaryotes | |
| Enterobacteriaceae | *E. coli* |
| | K 12 strain MM294 |
| | X1776 |
| | W3110 |
| | K5 772 |
| | *Enterobacter* |
| | *Erwinia* |
| | *Klebsiella* |
| | *Proteus* |
| | *Salmonella* (*S. tyhpimurium*) |
| | *Serratia* (*S. marcescans*) |
| | *Shigella* |
| | Bacilli (*B. subtilis* and *B. licheniformis*) |
| | *Pseudomonas* (*P. aeruginosa*) |
| | *Streptomyces* |
| Eukaryotes | |
| Yeasts | *Saccharomyces cerevisiae* |
| | *Schizosaccharomyces pombe* |
| | *Kluyveromyces* |
| | *K. lactis* MW98-8C, CBS683, CBS4574 |
| | *K. fragilis* |
| | *K. bulgaricus* |
| | *K. wickeramii* |
| | *K. waltii* |
| | *K. drosophilarum* |
| | *K. thermotolerans* |
| | *K. marxianus; yarrowia* |
| | *Pichia pastoris* |
| | *Candida* |
| | *Trichoderma reesia* |
| | *Neurospora crassa* |
| | *Torulopsis* |
| | *Rhodotorula* |
| | *Schwanniomyces* (*S. occidentalis*) |
| Filamentous Fungi | *Neurospora* |
| | *Penicillium* |
| | *Tolypocladium* |
| | *Aspergillus* (*A. nidulans* and *A. niger*) |
| Invertebrate cells | *Drosophila* S2 |
| | *Spodoptera* Sf9 |
| Vertebrate cells | Chinese Hamster Ovary (CHO) |
| | simian COS |
| | COS-7 |
| | HEK 293 |

Vector choice is dictated by the organism or cells being used and the desired fate of the vector. Vectors may replicate once in the target cells, or may be "suicide" vectors. In general, vectors comprise signal sequences, origins of replication, marker genes, enhancer elements, promoters, and transcription termination sequences. The choice of these elements depends on the organisms in which the vector will be used and are easily determined. Some of these elements may be conditional, such as an inducible or conditional promoter that is turned "on" when conditions are appropriate. Examples of inducible promoters include those that are tissue-specific, which relegate expression to certain cell types, steroid-responsive, or heat-shock reactive. Some bacterial repression systems, such as the lac operon, have been exploited in mammalian cells and transgenic animals. Vectors often use a selectable marker to facilitate identifying those cells that have incorporated the vector. Many selectable markers are well known in the art for the use with prokaryotes, usually antibiotic-resistance genes or the use of autotrophy and auxotrophy mutants.

Antisense and Sense GRK2 Oligonucleotides

Using antisense and sense GRK2 oligonucleotides can prevent GRK2 polypeptide expression. These oligonucleotides bind to target nucleic acid sequences, forming duplexes that block transcription or translation of the target sequence by enhancing degradation of the duplexes, terminating prematurely transcription or translation, or by other means.

Antisense or sense oligonucleotides are singe-stranded nucleic acids, either RNA or DNA, which can bind target GRK2 mRNA (sense) or GRK2 DNA (antisense) sequences. According to the present invention, antisense or sense oligonucleotides comprise a fragment of the GRK2 DNA coding region of at least about 14 nucleotides, preferably from about 14 to 30 nucleotides. In general, antisense RNA or DNA molecules can comprise at least 5, 10, 15, 20, 25, 30, 35, 40, 45, 50, 55, 60, 65, 70, 75, 80, 85, 90, 95, 100 bases in length or more. Methods to derive antisense or a sense oligonucleotides from a given cDNA sequence are well known in the art.

Modifications of antisense and sense oligonucleotides can augment their effectiveness. Modified sugar-phosphodiester bonds or other sugar linkages increase in vivo stability by conferring resistance to endogenous nucleases without disrupting binding specificity to target sequences. Other modifications can increase the affinities of the oligonucleotides for their targets, such as covalently linked organic moieties or poly-(L)-lysine. Other attachments modify binding specificities of the oligonucleotides for their targets, including metal complexes or intercalating (e.g., ellipticine) and alkylating agents.

Introduction of Antisense or Sense Oligonucleotides into Target Cells

To introduce antisense or sense oligonucleotides into target cells (cells containing the target nucleic acid sequence), any gene transfer method may be used and are well known to those of skill in the art. Examples of gene transfer methods include 1) biological, such as gene transfer vectors like Epstein-Barr virus or conjugating the exogenous DNA to a ligand-binding molecule, 2) physical, such as electroporation, and 3) chemical, such as $CaPO_4$ precipitation and oligonucleotide-lipid complexes.

The terms "host cell" and "recombinant host cell" are used interchangeably. Such terms refer not only to a particular subject cell but also to the progeny or potential progeny of such a cell. Because certain modifications may occur in succeeding generations due to either mutation or environmental influences, such progeny may not, in fact, be identical to the parent cell, but are still included within the scope of the term.

Methods of eukaryotic cell transfection and prokaryotic cell transformation are well known in the art. The choice of host cell will dictate the preferred technique for introducing the nucleic acid of interest. Table 13, which is not meant to be limiting, summarizes many of the known techniques in the art. Introduction of nucleic acids into an organism may also be done with ex vivo techniques that use an in vitro method of transfection, as well as established genetic techniques, if any, for that particular organism.

TABLE 13

Methods to introduce nucleic acid into cells

| Cells | Methods |
| --- | --- |
| Prokaryotes (bacteria) | Calcium chloride<br>Electroporation |
| Eukaryotes | Calcium phosphate transfection<br>Diethylaminoethyl (DEAE)-Dextran transfection<br>Electroporation |
| Mammalian cells | Cationic lipid reagent transfection<br>Retroviral<br>Polybrene<br>Microinjection<br>Protoplast fusion |
| Insect cells (in vitro) | Baculovirus systems |
| Yeast | Electroporation<br>Lithium acetate<br>Spheroplast fusion |
| Plant cells | *Agrobacterium* transformation<br>Biolistics (microprojectiles)<br>Electroporation (protoplasts)<br>Polyethylene glycol (PEG) treatment<br>Liposomes<br>in planta microinjection<br>Seed imbibition<br>Laser beam<br>Silicon carbide whiskers |

Vectors often use a selectable marker to facilitate identifying those cells that have incorporated the vector. Many selectable markers are well known in the art for the use with prokaryotes, usually antibiotic-resistance genes or the use of autotrophy and auxotrophy mutants. Table 14 lists often-used selectable markers for mammalian cell transfection.

TABLE 14

Useful selectable markers for eukaryote cell transfection

| Selectable Marker | Selection | Action |
| --- | --- | --- |
| Adenosine deaminase (ADA) | Media includes 9-β-D-xylofuranosyl adenine (Xyl-A) | Conversion of Xyl-A to Xyl-ATP, which incorporates into nucleic acids, killing cells. ADA detoxifies |

TABLE 14-continued

Useful selectable markers for eukaryote cell transfection

| Selectable Marker | Selection | Action |
|---|---|---|
| Dihydrofolate reductase (DHFR) | Methotrexate (MTX) and dialyzed serum (purine-free media) | MTX competitive inhibitor of DHFR. In absence of exogenous purines, cells require DHFR, a necessary enzyme in purine biosynthesis. |
| Aminoglycoside phosphotransferase ("APH", "neo", "G418") | G418 | G418, an aminoglycoside detoxified by APH, interferes with ribosomal function and consequently, translation. |
| Hygromycin-B-phosphotransferase (HPH) | hygromycin-B | Hygromycin-B, an aminocyclitol detoxified by HPH, disrupts protein translocation and promotes mistranslation. |
| Thymidine kinase (TK) | Forward selection (TK+): Media (HAT) incorporates aminopterin. Reverse selection (TK−): Media incorporates 5-bromodeoxyuridine (BrdU). | Forward: Aminopterin forces cells to synthesze dTTP from thymidine, a pathway requiring TK. Reverse: TK phosphorylates BrdU, which incorporates into nucleic acids, killing cells. |

A host cell of the invention, such as a prokaryotic or eukaryotic host cell in culture can be used to produce GRK2. Accordingly, the invention provides methods for producing GRK2 using the host cells of the invention. In one embodiment, the method comprises culturing the host cell of the invention (into which a recombinant expression vector encoding GRK2 has been introduced) in a suitable medium, such that GRK2 is produced. In another embodiment, the method further comprises isolating GRK2 from the medium or the host cell.

The invention provides an insulin sensitizing compound identified by any of the methods described above. In addition, the invention provides a kit comprising an insulin sensitizing compound identified by any of methods described above.

Kits

In various embodiments, the present invention can also involve kits. Such kits can include the compounds of the present invention and, in certain embodiments, instructions for administration. When supplied as a kit, different components of a compound formulation can be packaged in separate containers and admixed immediately before use. Such packaging of the components separately can, if desired, be presented in a pack or dispenser device which may contain one or more unit dosage forms containing the compound. The pack may, for example, comprise metal or plastic foil such as a blister pack. Such packaging of the components separately can also, in certain instances, permit long-term storage without losing activity of the components. In addition, if more than one route of administration is intended or more than one schedule for administration is intended, the different components can be packaged separately and not mixed prior to use. In various embodiments, the different components can be packaged in one combination for administration together.

Kits may also include reagents in separate containers such as, for example, sterile water or saline to be added to a lyophilized active component packaged separately. For example, sealed glass ampules may contain a lyophilized insulin sensitization compound and in a separate ampule, sterile water, sterile saline or sterile each of which has been packaged under a neutral non-reacting gas, such as nitrogen. Ampules may consist of any suitable material, such as glass, organic polymers, such as polycarbonate, polystyrene, ceramic, metal or any other material typically employed to hold reagents. Other examples of suitable containers include bottles that may be fabricated from similar substances as ampules, and envelopes that may consist of foil-lined interiors, such as aluminum or an alloy. Other containers include test tubes, vials, flasks, bottles, syringes, and the like. Containers may have a sterile access port, such as a bottle having a stopper that can be pierced by a hypodermic injection needle. Other containers may have two compartments that are separated by a readily removable membrane that upon removal permits the components to mix. Removable membranes may be glass, plastic, rubber, and the like.

In certain embodiments, kits can be supplied with instructional materials. Instructions may be printed on paper or other substrate, and/or may be supplied as an electronic-readable medium, such as a floppy disc, mini-CD-ROM, CD-ROM, DVD-ROM, Zip disc, videotape, audio tape, and the like. Detailed instructions may not be physically associated with the kit; instead, a user may be directed to an Internet web site specified by the manufacturer or distributor of the kit, or supplied as electronic mail.

EXAMPLES

Without further elaboration, it is believed that one skilled in the art can, using the preceding description, utilize the present invention to its fullest extent. The following specific examples are offered by way of illustration and not by way of limiting the remaining disclosure.

Example 1

GRK2 and Gαq/11

A. Materials

Mouse monoclonal anti-cdc42 antibody, rabbit polyclonal anti-p85 (N—SH2) and anti-IRS-1 antibodies, cdc42 assay kit and protein A agarose were purchased from Upstate Biotechnology Inc. (Lake Placid, N.Y.). Mouse monoclonal anti-phosphotyrosine (PY20) antibody was from Transduction Laboratories (Lexington, Ky.). Rabbit polyclonal anti-GLUT4 antibody was purchased from Chemicon International Inc. (Temecula, Calif.). Rabbit polyclonal anti-GRK2, anti-GRK3, anti-GRK5, anti-GRK6, anti-Gαq/11, and anti-cdc42 (P1) antibodies, and horseradish peroxidase-linked anti-rabbit and -mouse antibodies were from Santa Cruz Biotechnology (Santa Cruz, Calif.). Sheep IgG and fluorescein isothiocyanate (FITC)-conjugated and tetramethyl rhodamine isothiocyanate (TRITC)-conjugated anti-rabbit and anti-mouse IgG antibodies were from Jackson Immunoresearch Laboratories Inc. (West Grove, Pa.). SuperFECT was purchase from Qiagen (Valencia, Calif.). Oligofectamine was purchased from Invitrogen (Carlsbad, Calif.). SiRNA of GRK2 (sense: UGA CUU CAG UGU GCA UCG A dAdT (SEQ ID NO: 8), anti: U CGA UGC ACA CUG MG UCA dAdT (SEQ ID NO: 9)) and was purchased from Dharmacon (Lafayette, Colo.). Dulbecco's modified Eagle's medium (DMEM), Opti-MEM I, and fetal bovine serum (FBS) were purchased from Gibco Life Technologies (Grand Island, N.Y.). Plasmid vectors encoding wild type- and kinase deficient-(K220R) GRK2 were kindly provided by Dr. Robert J Lefkowitz (Duke University, NC). All radioisotopes were from ICN (Costa Mesa, Calif.). All other reagents were purchased from Sigma Chemical Co. (St. Louis, Mo.).

B. Construction of Deletion Mutant of GRK2

A deletion mutant of GRK2 which lacked RGS domain was constructed using PCR technique. Briefly, the 5'-terminus fragment of GRK2 upstream of RGS domain (upstream fragment; 159 bp) and the 3'-terminus fragment of GRK2 downstream of RGS domain (downstream fragment; 1543 bp) were separately generated by PCR. Antisense primer for the upstream fragment had a 15 bp sequence of the 5'-terminus of the downstream fragment in its 3'-terminus, while the sense primer for the downstream fragment had a 15 bp sequence of the 3'-terminus of the upstream fragment in its 5'-terminus. Then, these PCR products were mixed and PCR was performed again with 15 cycles, generating a sequence of GRK2 which lacked the RGS domain. The product of the second PCR with the size of interest was purified from an agarose gel using Gel Extraction Kit (Qiagen), and inserted into the SmaI site of pcDNA3.1 (Invitrogen).

C. Generation of Adenovirus Vectors

Adenoviruses were constructed using Adenovirus Expression Vector Kit (Takara, Japan) according to the manufacturer's instructions. Briefly, wild type- and kinase deficient-GRK2 were excised by digestion with PmeI and were inserted into the unique SwaI site of the full length adenovirus genome cloned in the cassette cosmid, pAxCAwt. Obtained recombinant cosmid and control cosmid pAxCAiLacZ containing a cDNA encoding β-galactosidase (LacZ) were co-transfected into human embryonic kidney 293 cells together with the adenovirus DNA-terminal protein complex digested at several sites by the calcium phosphate method using CellPhect Transfection Kit (Pharmacia). The recombinant adenoviruses were generated through homologous recombination. They were amplified in 293 cells and viral stock solutions with the viral titer >$10^8$ pfu/ml were prepared.

D. Cell Culture and Cell Treatment

3T3-L1 cells were cultured and differentiated. For adenovirus infection, 3T3-L1 adipocytes were transduced for 16 h in DME high glucose medium with 5% heat inactivated serum with 40 multiplicity of infection (m.o.i.) of either the recombinant adenovirus of wild type-GRK2 and kinase deficient-GRK2 or a control recombinant adenovirus of LacZ. Transduced cells were incubated for 48 h at 37° C. in 10% $CO_2$ and DME high glucose medium with 10% heat inactivated serum, followed by incubation in the starvation media required for the assays. The efficiency of adenovirus mediated gene transfer was above 90% as measured by histocytochemical staining of LacZ infected cells with β-galactosidase. Rat-1 fibroblasts over-expressing human insulin receptors (HIRc-B cells) were cultured in DME low glucose medium with 10% heat inactivated serum and 0.5% methotrexate in a 5% $CO_2$ environment at 37° C. Cultures were never allowed to be completely confluent.

E. Transfection of Plasmid Vectors

Transient transfection of plasmid vectors were performed with SuperFECT (Qiagen) in accordance with the manufacture's instructions. Cells were re-seeded in complete culture medium and incubated for 16 h, when the confluence of the cells was nearly 50-60%. Transfection reagent and vectors were removed 3 h after transfection. Cells were cultured in complete culture medium for 36 h, serum-starved for 16 h, and used for each assay.

F. 2-Deoxyglucose Uptake

Glucose uptake was measured. Forty-eight h after adenovirus infection, 3T3-L1 adipocytes were serum starved for 3 h, and the cells were stimulated with 17 nM insulin in KRP-Hepes buffer (10 mM Hepes pH 7.4, 131.2 mM NaCl, 4.7 mM KCl, 1.2 mM $MgSO_4$, 2.5 mM $CaCl_2$, 2.5 mM $NaH_2PO_4$) for 30 min at 37° C. Glucose uptake was determined in triplicate at each point after the addition of 2-[$^3$H] deoxyglucose (0.1 µCi, final concentration 0.1 mM) in KRP-Hepes buffer for 5 min at 37° C.

G. Transfection of siRNA

Transfection of GRK2 siRNA was performed using Oligofectamine (Invitrogen, CA) according to the manufacturer's instructions. Briefly, 3T3-L1 preadipocytes were reseeded in 6 well plates the day before transfection, and cultured for 24 h. On the day of transfection, siRNA and Oligofectamine were separately diluted in Opti-MEM I without serum, and incubated at room temperature for 10 min. They were mixed and incubated at room temperature for 20 min. The cells at ~40% confluence were washed once and serum free medium was added. The mixture of siRNA and Oligofectamine was overlaid onto the cells, which were then incubated for 4 h at 37° C. Growth medium containing 3 times the normal concentration of serum was added without removing the transfection mixture. Protein expression was examined by Western blotting 1 to 4 days after transfection.

H. Microinjection of Antibodies, siRNAs and Expression Vectors

Microinjection was carried out using a semiautomatic Eppendorf microinjection system. All reagents for microinjection were dissolved in microinjection buffer containing 5 mM sodium phosphate (pH 7.2), 100 mM KCl. Antibodies or control IgG at 5 mg/ml or 5 µM siRNAs mixed with FITC-Dextran were injected into the cytoplasm of the cells. Expression vectors at 0.1 mg/ml were directly injected into the nuclei of living cells. Protein expression was allowed to continue for 24 h.

The efficiency of siRNA under the microinjection was confirmed by RT-PCR method. Approximately 200 mature 3T3-L1 adipocytes in 3 µl complete medium were spotted on collagen-coated coverslips and incubated for 15 min in a humidified chamber, then filled with complete medium. The next day, all of the cells were microinjected with GRK2 or scrambled negative control siRNA. Forty-eight hrs after microinjection, total RNA was purified from injected cells using RNeasy mini kit (QIAGEN). The RT-PCR reaction was performed with a GRK2 or PP2A (as a control)-specific primer set using One-step RT-PCR kit (QIAGEN), according to the manufacturer's specification.

I. Immunostaining and Immunofluorescence Microscopy

Immunostaining of GLUT4 was performed. 3T3-L1 adipocytes were stimulated with various concentration of insulin for 20 min at 37° C. and were fixed in 3.7% formaldehyde in PBS for 10 min at room temperature. Following washing, the cells were permeabilized with 0.1% Triton X-100 in PBS for 10 min and blocked with 2% FCS in PBS for 10 min. The cells were then incubated with anti-GLUT4 antibody in PBS with 2% FCS overnight at 4° C. in antibody or siRNA injection studies. In nuclear injection studies, they were incubated with both anti-GLUT4 antibody and anti-6X-His-tag (for GRK2) or anti-HA-tag (for ERK1) antibody in PBS with 2% FCS overnight at 4° C. After washing, GLUT4 and either injected IgG, 6X-His-GRK2 or HA-ERK1 were stained with TRITC-conjugated donkey anti-rabbit IgG antibody and FITC-conjugated donkey anti-mouse or anti-sheep antibody, respectively, followed by the observation with an immunofluorescence microscope. In all counting experiments, the observer was blinded to the experimental condition of each coverslip.

J. Western Blotting

Serum-starved 3T3-L1 cells were stimulated with 17 nM insulin at 37° C. for various time periods as indicated in each experiment. The cells were lysed in solubilizing buffer containing 20 mM Tris, 1 mM EDTA, 140 mM NaCl, 1% Nonidet P-40 (NP-40), 1 mM $Na_3VO_4$, 1 mM PMSF, and 10 mM NaF, pH 7.5 for 15 min at 4° C. The cell lysates were centrifuged to remove insoluble materials. For Western blot analysis, whole cell lysates (20-50 μg protein) were denatured by boiling in Laemmli sample buffer containing 100 mM dithiothreitol and resolved by SDS-PAGE. Gels were transferred to polyvinylidene difluoride (PVDF) membrane (Immobilon-P, Millipore, Bedford, Mass.) using Transblot apparatus (Bio-Rad, Hercules, Calif.). For immunoblotting, membranes were blocked and probed with specific antibodies. Blots were then incubated with horseradish peroxidase-linked secondary antibodies followed by chemiluminescence detection, according to the manufacturer's instructions (Pierce Chemical Co., Rockford, Ill.).

K. PI3-Kinase Assay

3T3-L1 adipocytes were starved for 16 h and stimulated with insulin (17 nM) for 10 min, washed once with ice-cold PBS, lysed, and subjected to immunoprecipitation (300 to 500 μg total protein) with anti-IRS-1 antibody for 4 h at 4° C. Immunocomplexes were precipitated with protein A-plus agarose (Upstate Biotechnology Inc.; Lake Placid, N.Y.). The immunoprecipitates were washed twice with each following buffer: (i) PBS, containing 1% Nonidet-P40, 100 μM sodium orthovanadate, pH 7.4; (ii) 100 mM Tris, 0.5 M LiCl, 100 μM sodium orthovanadate, pH 7.4; and (iii) 10 mM Tris, 100 mM NaCl, 100 μM sodium orthovanadate, pH 7.4. The washed immunocomplexes were incubated with phosphatidylinositol for 5 min and then with [γ-$^{32}$P]ATP (3000 Ci/mmol) for 5 min at room temperature. Reactions were stopped with 20 μl of 8 N HCl, mixed with 160 μl of $CHCl_3$:methanol (1:1). Samples were centrifuged and the lower organic phase was applied to a silica gel thin-layer chromatography (TLC) plate which had been coated with 1% potassium oxalate. TLC plates were developed in $CHCl_3$:$CH_3OH$:$H_2O$:$NH_4OH$ (60:47:11.3:2), dried, and exposed to an X-ray film. PI3-kinase activity was quantitated by scanning the film using NIH Image.

L. cdc42 Assay

Cdc42 activity was measured according to the manufacturer's instructions (Upstate Biotechnology Inc.; Lake Placid, N.Y.). 3T3-L1 adipocytes were starved for 16 h and stimulated with 17 nM insulin for 1 min, washed once with ice-cold PBS and lysed with lysis buffer containing 25 mM HEPES (pH 7.5), 150 mM NaCl, 1% Igepal CA-630, 10 mM $MgCl_2$, 1 mM EDTA, 10% glycerol, 1 mM $Na_3VO_4$, 10 μg/ml aprotinin, 10 μg/ml leupeptin, and 25 mM NaF for 15 min at 4° C. Insoluble materials were removed by centrifugation. For a negative control, cell lysate was incubated with 1 mM GDP for 15 min at 30° C. Five μg PAK-1 agarose beads, which specifically bound to active cdc42, were added to the cell lysates and incubated for 1 h at 4° C. Agarose beads were washed with lysis buffer three times, boiled in 2× Laemmli sample buffer. Samples were resolved by SDS-PAGE and immunoblotted with anti-cdc42 antibody.

M. Statistical Analysis

Data were analyzed by Student's t test. p values <0.05 were considered significant.

N. Results

Insulin-Induced GLUT4 Translocation is Increased by Microinjection of GRK2 Antibody or siRNA, and Decreased by Overexpression of GRK2.

Using immunofluorescent staining to detect GLUT4 at the plasma membrane, the effects of GRK2 inhibition on insulin-stimulated GLUT4 translocation were measured. As shown in FIG. (A, D, E), for microinjection assay, 3T3-L1 adipocytes on coverslips were serum-starved for 4 h, and anti-GRK2 antibody, anti-GRK5 antibody, anti-GRK6 antibody, sheep IgG, GRK2 siRNA, or control siRNA was microinjected. For GRK2 overexpression assay, 3T3-L1 adipocytes on coverslips were infected with adenovirus expressing wild type- or kinase deficient-GRK2 or control LacZ. Forty-eight h after infection, these cells were serum-starved for 4 h. Cells were stimulated with 0.02 nM, 0.2 nM or 1.7 nM insulin for 20 min. GLUT4 was stained as described in the Examples section. The percentage of cells positive for GLUT4 translocation was calculated by counting at least 100 cells at each point. The data are mean ±S.E. from three independent experiments. In (B), siRNA of GRK2 (+) or control siRNA (−) was transfected in 3T3-L1 preadipocytes using Oligofectamine as described below. The indicated days after transfection, total cell lysates were prepared and analyzed by Western blotting using anti-GRK2 antibody as described in the Examples section. Representative blots are shown from two independent experiments. In (C), the efficiency of siRNA under the microinjection into 3T3-L1 adipocytes was confirmed by the mRNA quantification as described in the Examples section. All of 3T3-L1 adipocytes on coverslips (approximately 200 cells spotted on each coverslip) were microinjected with GRK2 or scrambled control (scramble) siRNA. Forty-eight hrs after microinjection, total RNA was purified and used for RT-PCR reaction with GRK2 or PP2A (Cont.) primer set. A representative image from two independent experiments is shown. S; size marker. In (F), 3T3-L1 adipocytes were infected with adenovirus expressing wild type —(WT) or kinase deficient-GRK2 (KD) or control LacZ (Control). Forty-eight h after infection, these cells were serum-starved for 3 h, stimulated with 17 nM insulin for 30 min, and [3H] 2-deoxy-glucose (2DOG) uptake was measured as described in the Examples section. The data are the mean ±S.E. from three independent experiments. Statistically significant differences versus control are indicated (*; P<0.05).

In the basal state, most cells displayed GLUT4 staining in the perinuclear region, while insulin treatment led to appearance of GLUT4 at the plasma membrane (FIGS. 1A, C and D). Microinjection of GRK2 antibody into 3T3-L1 adipocytes did not alter basal GLUT4 staining, but led to a 65% and 47% increase in GLUT4 translocation when cells were stimulated with 0.02 nM or 0.2 nM insulin, respectively, with no significant effect at 1.7 nM insulin concentration (FIG. 1A). The specificity of the GRK2 antibody was confirmed by Western blotting (data not shown), and microinjection of antibodies against GRK5 or GRK6 had no effect on GLUT4 localization. Thus, inhibition of endogenous GRK2 by antibody microinjection led to increased insulin sensitivity for stimulation of GLUT4 translocation.

To further support the results with the GRK2 antibody, siRNA against GRK2 were utilized. The efficiency of this siRNA at silencing GRK2 protein was demonstrated by Western blotting of cell lysates from 3T3-L1 preadipocytes that had been transfected with GRK2 siRNA. As shown in FIG. 1B, 1, 2 and 3 days post transfection, GRK2 protein was decreased by 64, 79 and 86%, respectively. Since transfection efficiency of this chemical reagent is not 100% (~85%), it is probable that almost complete inhibition occurred in the cells expressing the siRNA. When RNA is prepared from cover slips in which all of the cells are microinjected (~200 cells/coverslip) the resulting RT-PCR data show that the microinjected GRK2 siRNA "knock down" the GRK2 mRNA to undetectable levels (FIG. 1C). With the microinjection approach, only cells that contain this siRNA are assessed for GLUT4 translocation. As shown in FIG. 1D, insulin-stimulated GLUT4 translocation was increased by 55% at 0.02 nM insulin and by 48% at 0.2 nM insulin in GRK2 siRNA injected cells.

The effect of adenoviral vectors encoding wild type- (WT-) and kinase deficient- (KD-) (K220R) GRK2 on GLUT4 translocation was examined. Adenoviral mediated expression of either WT- or KD-GRK2 in 3T3-L1 adipocytes decreased insulin-stimulated GLUT4 translocation (FIG. 1E). The effects on 2-deoxyglucose (2-DOG) uptake were also determined (FIG. 1F), and WT- and KD-GRK2 inhibited insulin-stimulated 2-DOG uptake by 46% and 44%, respectively. Interestingly, the inhibitory effects of WT- and KD-GRK2 expression on GLUT4 translocation and 2-DOG uptake were quite comparable. Taken together, these results suggest that GRK2 is an endogenous inhibitor of insulin-induced GLUT4 translocation and glucose transport and that this inhibitory function does not involve the kinase activity of GRK2.

GRK2 does not Affect Insulin Receptor Tyrosine Phosphorylation or Activation of the IRS-1 Pathway.

To assess the mechanisms of GRK2-mediated inhibition of insulin-induced GLUT4 translocation and 2-DOG uptake, the role of GRK2 in insulin signaling was examined. 3T3-L1 adipocytes were infected with adenovirus expressing wild type- (WT) or kinase deficient-GRK2 (KD) or control LacZ (C). As shown in FIG. 2(A), forty-eight h after infection, these cells were serum-starved for 16 h, stimulated with 17 nM insulin for 5 min and lysed. Total cell lysates were analyzed by Western blotting using anti-insulin receptor (IR), anti-phosphotyrosine (PY20) or anti-GRK2 antibody as described in the Examples section. Representative blots are shown from three independent experiments. In (B), forty-eight h after infection, these cells were serum-starved for 16 h, stimulated with 17 nM insulin for 5 min (for IRS-1 and PY20 blots) or 10 min (for p85 blot) and lysed. Samples were immunoprecipitated with anti-IRS-1 antibody. Immunoprecipitates or total cell lysates were analyzed by Western blotting using anti-IRS-1, anti-phosphotyrosine (PY20), or anti-p85 antibody as described in the Examples section. Representative blots are shown from three independent experiments. In (C), forty-eight h after infection, these cells were serum-starved for 16 h, stimulated with 17 nM insulin for 10 min and lysed. Samples were immunoprecipitated with anti-IRS-1 antibody. PI3-kinase activity was measured as described in the Examples section. A representative film is shown and the graph represents the mean ±S.E. of three independent experiments.

As shown in FIG. 2A, adenoviral expression of WT-, or KD-GRK2 did not alter the expression level or tyrosine phosphorylation state of the insulin receptor. Additionally, the insulin receptor did not co-precipitate using anti-GRK2 antibody, either before or after insulin stimulation (data not shown). Expression of WT- or KD-GRK2 did not affect the expression level or insulin-induced tyrosine phosphorylation of IRS-1 and p85, the association of IRS-1 and p85, or IRS-1-associated PI3-kinase activity (FIG. 2B, C). Thus, the effects of GRK2 inhibition on insulin-stimulated glucose transport are independent of, or downstream of, the insulin receptor, IRS-1, and IRS-1-associated PI3-kinase.

GRK2 Directly Binds to Gαq/11 and Inhibits Insulin-Induced Activation of the Gαq/11 Pathway.

Figure 3:
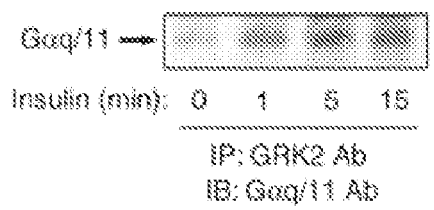
FIG. 3 depicts the effects of wild type- or kinase deficient GRK2 overexpression on Gαq/11-cdc42-PI3-kinase pathway in 3T3-L1 adipocytes.
Figure 3:
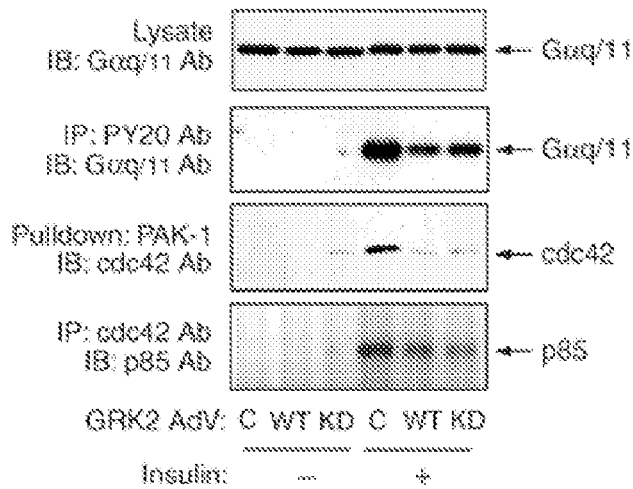
Figure 3:
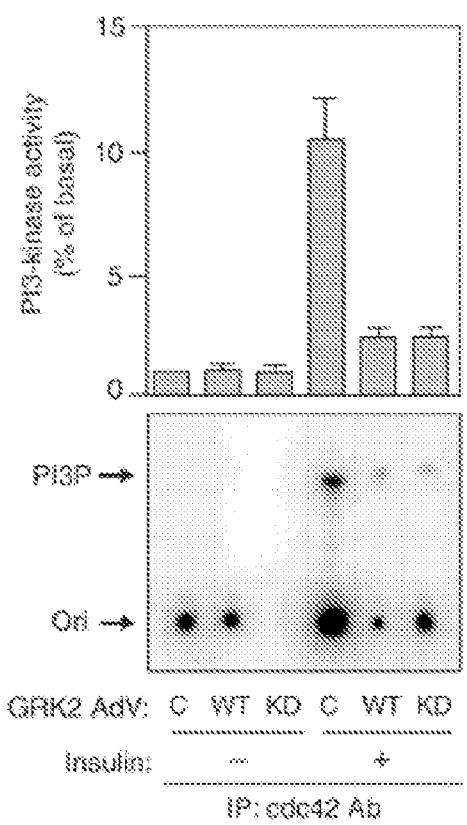

GLUT4 translocation involves insulin stimulation of Gαq/11, and because GRK2 is selective for Gαq/11, the association of endogenous GRK2 and Gαq/11 before and after insulin stimulation was examined. As shown in FIG. 3, (A) 3T3-L1 adipocytes were serum-starved for 16 h, stimulated with 17 nM insulin for the indicated time periods and lysed. Samples were immunoprecipitated with anti-GRK2 antibody. Immunoprecipitates were analyzed by Western blotting using anti-Gαq/11 antibody as described in the Examples section. Representative blot is shown from three independent experiments. In (B), 3T3-L1 adipocytes were infected with adenovirus expressing wild type- (WT) or kinase deficient-GRK2 (KD) or control LacZ (C). Forty-eight h after infection, these cells were serum-starved for 16 h, stimulated with 17 nM insulin for 1 min (for Gαq/11 blot) or 10 min (for p85 blot) and lysed. Samples were immunoprecipitated with anti-phosphotyrosine (PY20) or cdc42 antibody. Immunoprecipitates and total cell lysates were analyzed by Western blotting using anti-Gαq/11 or anti-p85 antibody as described in the present Examples. Cdc42 activity was measured as described in the Examples section. The cells were stimulated with insulin for 1 min. Samples were pulled down with GST-PAK-1 and were analyzed by Western blotting using anti-cdc42 antibody. Representative blots are shown from three independent experiments. In (C), 3T3-L1 adipocytes were infected with adenovirus expressing wild type —(WT) or kinase deficient-GRK2 (KD) or control LacZ (C). Forty-eight h after infection, these cells were serum-starved for 16 h, stimulated with 17 nM insulin for 10 min and lysed. Samples were immunoprecipitated with anti-cdc42 antibody. PI3-kinase activity was measured as described in the Examples section. A representative film is shown and the graph represents the mean ±S.E. of three independent experiments.

Association of endogenous GRK2 and Gαq/11 was low in the basal state and was markedly enhanced by insulin with a maximal response by 5 min (FIG. 3A). The role of GRK2 in the Gαq/11 signaling pathway by using adenoviral-mediated expression of WT- or KD-GRK2 was next assessed (FIG. 3B, C). Insulin treatment causes increased tyrosine phosphorylation of Gαq/11, cdc42 activation, association of cdc42 and p85, and enhanced cdc42-associated PI3-kinase activity. Interestingly, overexpression of either WT- or KD-GRK2 inhibited insulin-induced Gαq/11 tyrosine phosphorylation (FIG. 3B, second row). This result suggests that while insulin leads to Gαq/11 tyrosine phosphorylation, the Gαq/11 which associates with GRK2 cannot be phosphorylated. Similarly, events downstream of Gαq/11 signaling, including cdc42 activation (as measured by precipitation with PAK1-CBD beads (FIG. 3B, third row)), p85 co-precipitation with cdc42 antibody (FIG. 3B, fourth row), and insulin-induced, cdc42-associated PI3-kinase activity (FIG. 3C) were also inhibited. The expression level of Gαq/11, cdc42, or p85 was not altered in adenoviral GRK2-WT or -KD transfected cells. Together, these results indicate that decreased activation of the insulin-stimulated Gαq/11 pathway can, at least in part, explain the inhibition of insulin-stimulated glucose transport by GRK2, and that this inhibitory mechanism is independent of GRK2 kinase activity.

Structural Determinants of GRK Function on Insulin Signaling.

Figure 4:
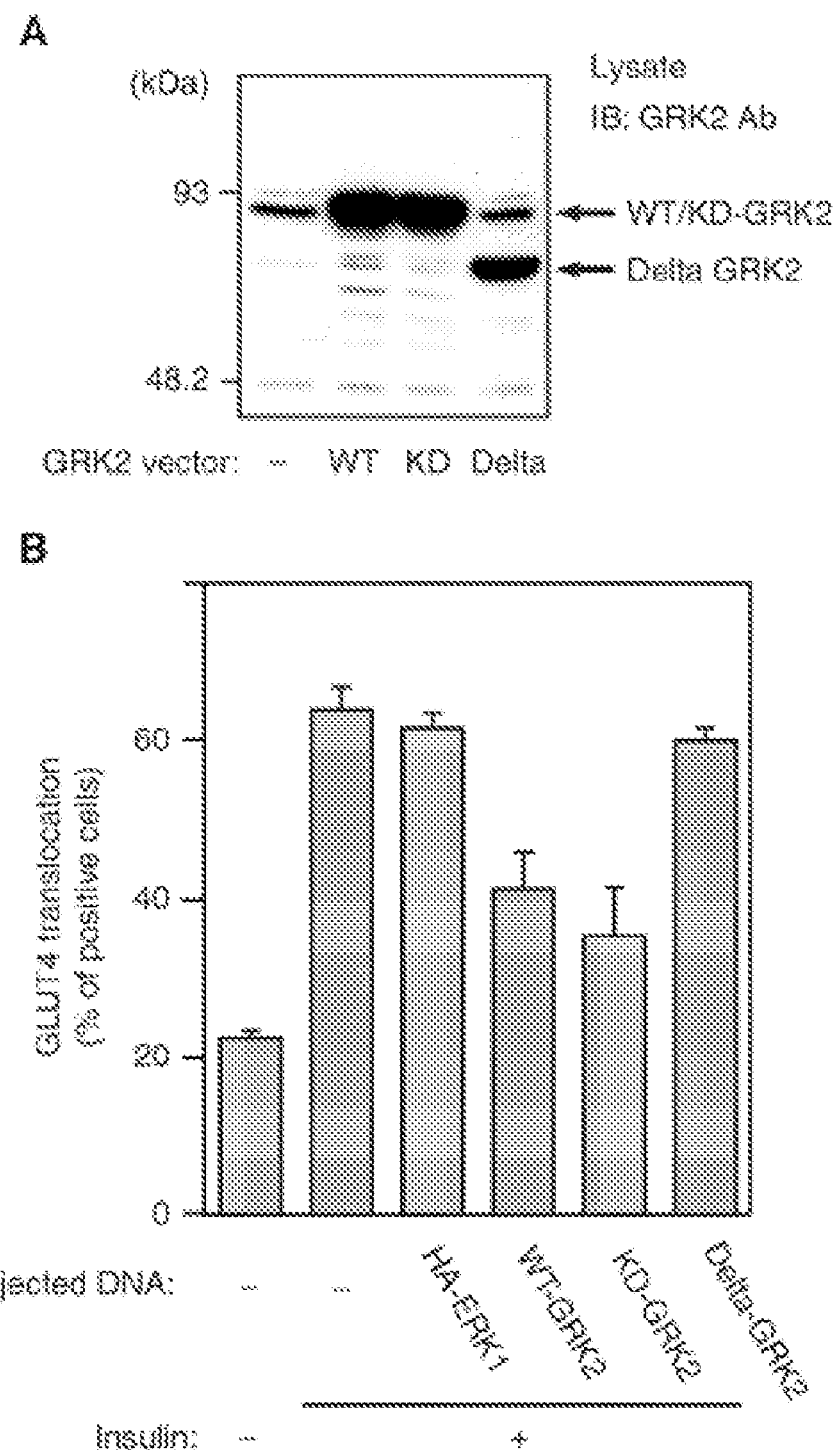
FIG. 4 depicts the effects of RGS domain of GRK2 on insulin-stimulated GLUT4 translocation in 3T3-L1 adipocytes.

Amino (N')-termini of GRKs contain sequence similarities to RGS domains of typical RGS proteins, and GRK2 can specifically recognize Gαq/11. Thus, the role of the RGS domain of GRK2 in insulin-stimulated GLUT4 translocation by constructing a GRK2 vector which lacks the RGS domain (delta-GRK2) was assessed. As shown in FIG. 4, (A) plasmid expression vectors of wild type- (WT-), kinase deficient- (KD-) or deletion mutant- (delta-) GRK2 were transfected in HIRc-B cells using SuperFECT as described in the Examples section. Forty-eight h after infection, these cells were lysed and total cell lysates were analyzed by Western blotting using anti-GRK2 antibody as described in the Examples section. These experiments were performed three times, and a representative result is shown. In (B), plasmid expression vectors of WT-GRK2, KD-GRK2, delta-GRK2 or control ERK1 (HA-ERK1) were microinjected into nuclei of 3T3-L1 adipocytes on coverslips. Twenty-four h after microinjection, 3T3-L1 adipocytes were serum starved for 4 h, and were stimulated with 1.7 nM insulin for 20 min. GLUT4 was stained as described in the Examples section. The cells expressing exogenous GRKs or ERK1 were detected by staining with anti-6X-His antibody or anti-HA antibody, respectively. The percentage of cells positive for GLUT4 translocation was calculated by counting at least 100 cells at each point. The data are mean ±S.E. from three independent experiments.

Western blot analysis using anti-GRK2 antibody revealed that delta-GRK2, as well as wild type- (WT-) and kinase deficient- (KD-)-GRK2, were comparably and well expressed after transfection of these vectors into HIRc-B cells (FIG. 4A). The effect of WT-, KD-, or delta-GRK2 on GLUT4 translocation was compared by microinjecting these vectors directly into the nuclei of 3T3-L1 adipocytes (FIG. 4B). Consistent with the effects of adenovirus infection on GLUT4 translocation and 2-DOG uptake (FIGS. 1E and F), overexpression of either WT- or KD-GRK2 by nuclear microinjection inhibited insulin-induced GLUT4 translocation. In contrast, overexpression of delta-GRK2 had no effect. As a negative control, a vector encoding WT-ERK1, which had no effect on GLUT4 translocation, was injected. This result suggests that the RGS domain of GRK2 is necessary for the inhibitory function of GRK2 on insulin-stimulated GLUT4 translocation, which is most likely a result of RGS domain binding to Gαq/11.

Figure 5:
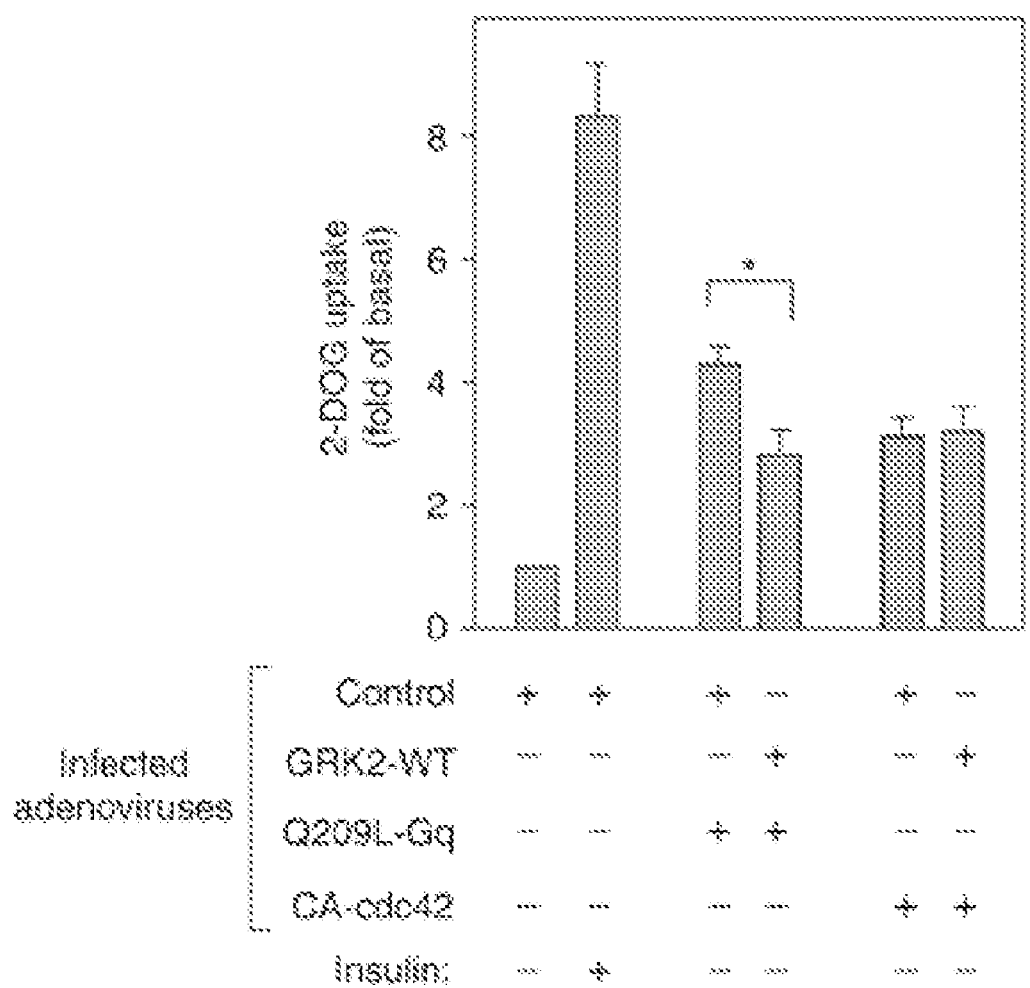
FIG. 5 depicts the effects of GRK2 on Q209L-Gq-induced 2-deoxyglucose uptake in 3T3-L1 adipocytes.

To further extend these findings, experiments were conducted with constitutively active (Q209L) Gαq. As shown in FIG. 5, 3T3-L1 adipocytes were co-infected with adenovirus expressing wild type-GRK2 (GRK2-WT), constitutively active Gq (Q209L-Gq), constitutively active cdc42 (CA-cdc42), and/or control LacZ (Control). Total number of multiplicity of infection (m.o.i.) was adjusted to 80 in each condition. Forty-eight h after infection, these cells were serum-starved for 3 h, stimulated with 17 nM insulin for 30 min, and [3H] 2-deoxy-glucose (2DOG) uptake was measured as described in the Examples section. The data are the mean ±S.E. from six independent experiments. Statistically significant differences versus control are indicated (*; P<0.05).

Expression of constitutively active Gαq (Q209L) leads to stimulation of glucose transport, as shown in FIG. 5. However, when adenoviruses containing GRK2-WT and Q209L-Gαq were simultaneously used to infect 3T3-L1 adipocytes, the expression of GRK2 inhibited the effect of Q209L-Gαq on glucose transport. cdc42 lies downstream of Gαq/11 in the insulin-induced glucose transport stimulatory pathway, and that constitutively active (CA) cdc42 can stimulate glucose transport when expressed in 3T3-L1 adipocytes. FIG. 5 shows that coexpression of GRK2 does not inhibit the stimulating effects of CA-cdc42. These results indicate that the ability of the GRK2 RGS domain to bind to Gαq underlies the mechanism of the inhibitory effect. Most likely, GRK2 binding to Gαq/11 affects a critical subcellular localization step, or prevents Gαq/11 from interacting with downstream effectors.

The compositions and methods of the invention are useful in attenuation of insulin resistance and/or restoration of insulin sensitivity, in a patient through GRK2 inhibition of the insulin signaling pathway leading to glucose transport stimulation, β2AR activation leading to recruitment of GRK2 to the plasma membrane, inhibiting the heterotrimeric G protein component, Gαq/11, in the regulation in insulin's metabolic actions in the patient's cells, expressing a phosphorylation resistant Gαq/11 in the patient's cells, or chemical inhibitors of GRK2, including small molecules, antisense molecules and siRNAs targeting GRK2. Such small chemicals may include RGS binding domain mimics, prepared by well known methods in the art, which allow binding to Gαq/11 without inhibiting the insulin induced phosphorylation of Gαq/11. Such small chemicals may be prepared and administered by well known methods in the art, more fully described below.

The in vitro methods of the invention are useful for screening of candidate compounds for those which have activity in the inhibition of the insulin signaling pathway. Such an in vitro screen is commercially useful in rapidly identifying potentially useful compounds, and eliminating ineffective compounds from further study.

Another use of the insulin signaling pathway antagonists of the invention is as a insulin signaling pathway inhibitor reagent in medical and biochemical research applications. For example, the insulin signaling pathway antagonists of the invention could be used as a molecular probe to determine if a phenomenon observed either in vitro or in vivo is mediated by insulin signaling pathway. Such compositions could be siRNAs against GRK2 or any other target capable of inhibiting the insulin signaling pathway. Such siRNAs may be designed according to the following section. Other small molecules which substantially mimic the function of GRK2 binding to Gαq/11, such as through RGS domain binding, may also be useful in the present invention.

Example 2

GRK2 and ET-1

A. Materials

Mouse monoclonal anti-cdc42 antibody, rabbit polyclonal anti-p85 (N—SH2), anti-phospho-IRS-1-against Ser307, and anti-IRS-1 antibodies, cdc42 assay kit and protein A agarose were purchased from Upstate Biotechnology Inc. (Lake Placid, N.Y.). Rabbit polyclonal anti-phospho-IRS-1-against Ser612 and -636 antibodies were from Cell Signaling Technology (Beverly, Mass.). Mouse monoclonal anti-phosphotyrosine (PY20) antibody was from Transduction Laboratories (Lexington, Ky.). Rabbit polyclonal anti-GLUT4 antibody was purchased from Chemicon International Inc. (Temecula, Calif.). Rabbit polyclonal anti-GRK2, anti-GRK3, anti-GRK5, anti-GRK6, anti-Gαq/11, and anti-cdc42 (P1) antibodies, and horseradish peroxidase-linked anti-rabbit and -mouse antibodies were from Santa Cruz Biotechnology (Santa Cruz, Calif.). Sheep IgG and fluorescein isothiocyanate (FITC)-conjugated and tetramethyl rhodamine isothiocyanate (TRITC)-conjugated anti-rabbit and anti-mouse IgG antibodies were from Jackson Immunoresearch Laboratories Inc. (West Grove, Pa.). siRNA against GRK2 is described above. Dulbecco's modified Eagle's medium (DMEM) and fetal bovine serum (FBS) were purchased from Life Technologies (Grand Island, N.Y.). Plasmid vectors encoding wild type and kinase deficient (K220R) GRK2 were kindly provided by Robert J. Lefkowitz (Duke University, NC). Radioisotope was from ICN (Costa Mesa, Calif.). All other reagents were purchased from Sigma Chemical Co. (St. Louis, Mo.).

B. Generation of Adenovirus Vectors

Adenoviruses were constructed using Adenovirus Expression Vector Kit (Takara, Japan) according to the manufacturer's instructions. The recombinant adenoviruses were amplified in 293 cells and viral stock solutions with the viral titer >$10^8$ pfu/mi were prepared.

C. Cell Culture and Cell Treatment

3T3-L1 cells were cultured and differentiated. Differentiated 3T3-L1 adipocytes (day 14 after differentiation) were incubated with 10 nM endothelin-1 for 24 h before some assays. For adenovirus infection, 3T3-L1 adipocytes (day 11 after differentiation) were transduced for 16 h in DME high glucose medium with 5% heat inactivated serum at a multiplicity of infection (m.o.i.) of 40 with either the recombinant adenovirus of wild type-GRK2 or kinase deficient-GRK2 or a LacZ-control. Transduced cells were incubated for 48 h at 37° C. in 10% $CO_2$ and DME high glucose medium with 10% heat inactivated serum, followed by incubation in starvation media. The efficiency of adenovirus mediated gene transfer was above 90% as measured by histocytochemical staining of LacZ-infected cells with β-galactosidase (data not shown).

D. Microinjection of Antibody or siRNA

Microinjection was carried out using a semiautomatic Eppendorf microinjection system. Antibodies for microinjection were concentrated and dissolved at 5 mg/ml in microinjection buffer containing 5 mM sodium phosphate (pH 7.2), 100 mM KCl. Antibodies or control IgG at 5 mg/ml or 5 μM siRNA mixed with FITC-dextran were injected into the cytoplasm of 3T3-L1 adipocytes (day 12-14 after differentiation) for GLUT4 ring assay. For the analysis of cell surface GLUT4-HA-epitope staining, HA-GLUT4-GFP expression vector DNA (0.1 mg/ml) was mixed together with 5 μM siRNA in microinjection buffer, and injected into the cell nucleus (day 10 after differentiation).

E. Immunostaining and Immunofluorescence Microscopy

Immunostaining of endogenous GLUT4 (ring assay) was performed. 3T3-L1 adipocytes were stimulated with insulin for 20 min at 37° C. and were fixed in 3.7% formaldehyde in PBS (phosphate-buffered saline) for 10 min at room temperature. Following washing, the cells were permeabilized with 0.1% Triton X-100 in PBS for 10 min and blocked with 2% FCS in PBS for 10 min. The cells were then incubated with anti-GLUT4 antibody in PBS with 2% FCS overnight at 4° C. After washing, GLUT4 and injected IgG were detected by incubation with TRITC-conjugated donkey anti-rabbit IgG antibody and FITC-conjugated donkey anti-mouse or anti-sheep antibody, respectively, followed by observation under an immunofluorescence microscope. In all counting experiments, the observer was blinded to the experimental condition of each coverslip.

For the quantitative analysis of exogenous HA-GLUT4-GFP membrane fusion, an expression vector encoding HA-GLUT4-GFP was microinjected. The expression vector DNA (0.1 mg/ml) was mixed together with siRNA (5 μM), and microinjected into the cell nucleus of 3T3-L1 adipocytes (day 10). Twenty-four hours after microinjection, the cells were then treated with or without ET-1 for 24 h, including 4 h starvation, and stimulated with or without insulin for 20 min. Fixed cells were stained with anti-HA monoclonal antibody (Covance, Calif.) without permeabilization for 30 min at 37° C. Cells were then washed and stained with a secondary Cy3-conjugated anti-mouse antibody. GFP fluorescent-positive cells were imaged on a Nikon TE300 inverted microscope. Images were captured and analyzed using Simple PCI software and a Hamamatsu Orca 12 bit CCD camera (C-Imaging Systems, PA). GLUT4 translocation and fusion with the plasma membrane was quantitated by taking the ratio of Cy3 (HA) to GFP (total) fluorescence. This measurement provides the ratio of the HA-GLUT4-GFP that has fused with the plasma membrane to the total amount of HA-GLUT4-GFP expressed in the cell, as described previously (20).

F. Western Blotting

Serum-starved 3T3-L1 adipocytes were stimulated with 17 nM insulin at 37° C. for various time periods as indicated in each experiment. The cells were lysed in solubilizing buffer containing 20 mM Tris, 1 mM EDTA, 140 mM NaCl, 1% Nonidet P-40 (NP-40), 1 mM $Na_3VO_4$, 1 mM PMSF, and 10 mM NaF, pH 7.5 for 15 min at 4° C. The cell lysates were centrifuged to remove insoluble materials. For western blot analysis, whole cell lysates (20-50 μg protein) were denatured by boiling in Laemmli sample buffer containing 100 mM dithiothreitol and resolved by SDS-PAGE. Gels were transferred to polyvinylidene difluoride (PVDF) membrane (Immobilon-P, Millipore, Bedford, Mass.) using Transblot apparatus (Bio-Rad, Hercules, Calif.). For immunoblotting, membranes were blocked and probed with specific antibodies. Blots were then incubated with horseradish peroxidase-linked secondary antibodies followed by chemiluminescence detection, according to the manufacturer's instructions (Pierce Chemical Co., Rockford, Ill.).

G. PI3-Kinase Assay

3T3-L1 adipocytes were starved for 16 h and stimulated with insulin (17 nM) for 10 min, washed once with ice-cold PBS, lysed, and subjected to immunoprecipitation (300 to 500 μg total protein) with anti-cdc42 or anti-IRS-1 antibody for 4 h at 4° C. Immunocomplexes were precipitated with protein A-plus agarose (Upstate Biotechnology Inc.; Lake Placid, N.Y.). The immunoprecipitates were washed three times with each of the following buffers: (i) PBS, containing 1% Nonidet-P40, 100 μM sodium orthovanadate, pH 7.4; (ii) 100 mM Tris, 0.5 M LiCl, 100 μM sodium orthovanadate, pH 7.4; and (iii) 10 mM Tris, 100 mM NaCl, 100 μM sodium orthovanadate, pH 7.4. The washed immunocomplexes were incubated with phosphatidylinositol for 5 min and then with [$\gamma$-$^{32}$P]ATP (3000 Ci/mmol) for 5 min at room temperature. Reactions were stopped with 20 μl of 8 N HCl, and mixed with 160 μl of $CHCl_3$:methanol (1:1). Samples were centrifuged and the lower organic phase was applied to a silica gel thin-layer chromatography (TLC) plate which had been coated with 1% potassium oxalate. TLC plates were developed in $CHCl_3$:$CH_3OH$:$H_2O$:$NH_4OH$ (60:47:11.3:2), dried, and exposed to an X-ray film. PI3-kinase activity was quantitated by scanning and analyzing the film using NIH Image.

H. cdc42 Assay

Cdc42 activity was measured according to the manufacturer's instructions (Upstate Biotechnology Inc.; Lake Placid, N.Y.). 3T3-L1 adipocytes were starved for 16 h and stimulated with 17 nM insulin or 10 nM endothelin-1 for 1 min, washed once with ice-cold PBS and lysed with lysis buffer containing 25 mM HEPES (pH 7.5), 150 mM NaCl, 1% Igepal CA-630, 10 mM $MgCl_2$, 1 mM EDTA, 10% glycerol, 1 mM Na$_3$VO$_4$, 10 µg/ml aprotinin, 10 µg/ml leupeptin, and 25 mM NaF for 15 min at 4° C. Insoluble materials were removed by centrifugation. For a negative control, cell lysate was incubated with 1 mM GDP for 15 min at 30° C. Five µg PAK-1 agarose beads, which specifically bind to active cdc42, were added to the cell lysates and incubated for 1 h at 4° C. Agarose beads were washed with lysis buffer three times, and boiled in 2× Laemmli sample buffer. Samples were resolved by SDS-PAGE and immunoblotted with anti-cdc42 antibody.

1. Statistical Analysis

Data were analyzed by Student's t test. p values <0.05 were considered significant.

J. Results

Microinjection of GRK2 Antibody or siRNA Blocks ET-1-Induced Insulin Resistance

Figure 7:
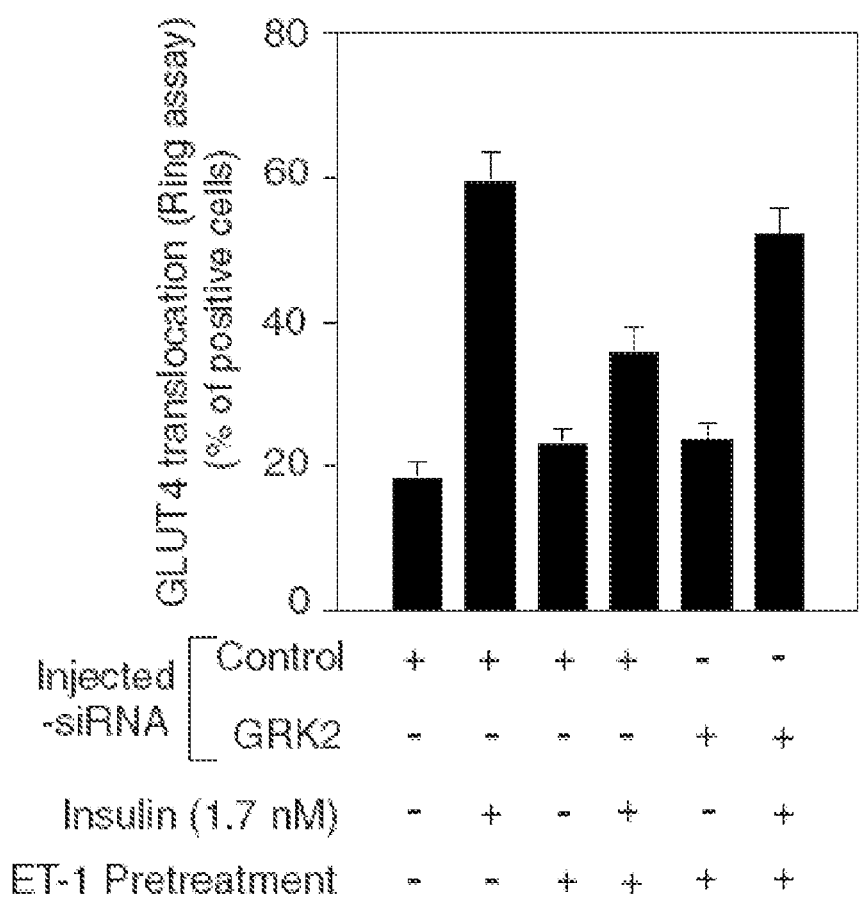
FIG. 7 depicts the effects of microinjection of anti-GRK2-siRNA on GLUT4 translocation in 3T3-L1 adipocytes.
Figure 8:
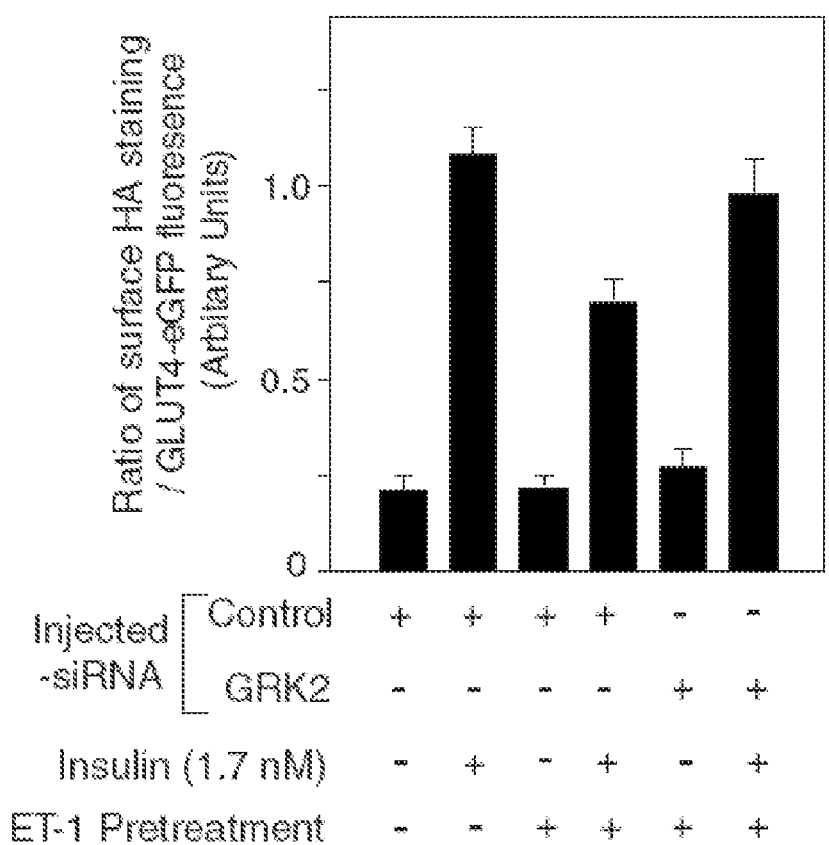
FIG. 8 is another depiction of the effects of microinjection of anti-GRK2-siRNA on GLUT4 translocation in 3T3-L1 adipocytes.

It is well established that GRK2 facilitates ET-1 signaling, and we have recently demonstrated that GRK2 can also function as a negative regulator of insulin action. Since chronic ET-1 treatment inhibits insulin-induced glucose transport, the role of GRK2 in ET-1-induced insulin resistance was investigated. Insulin-stimulated GLUT4 translocation was quantitated utilizing two different methods. First, GLUT4 translocation was assessed by immunofluorescent staining of endogenous GLUT4. In FIG. 6, 3T3-L1 adipocytes on coverslips were treated with or without 10 nM endothelin-1 (ET-1) for 24 h, after microinjection with anti-GRK2 antibody or control IgG. In FIG. 7, 48 h after microinjection with siRNA against GRK2 or scrambled siRNA (Control), 3T3-L1 adipocytes were treated with or without 10 nM endothelin-1 (ET-1) for 24 h. including 4 h serum-starvation. Cells were then stimulated with 1.7 nM insulin for 20 min. GLUT4 was immunostained as described under "Experimental Procedures". The percentage of cells positive for GLUT4 translocation (Ring assay) was calculated by counting at least 100 cells per condition. The data are the mean ±S.E. from three independent experiments. In FIG. 8, 24 h after nuclear microinjection of siRNA against GRK2 or scrambled siRNA (Control) together with HA-GLUT4-GFP expression vector, 3T3-L1 adipocytes were then pretreated with or without 10 nM endothelin-1 (ET-1) for 24 h, including 4 h serum-starvation. Cells were stimulated with 17 nM insulin for 20 min. The cell-surface HA-tag of exogenous HA-GLUT4-GFP was immunostained as described herein in the Examples. The ratio of HA staining/GLUT4-GFP fluorescence was measured by C-Imaging Systems on at least 40 cells per condition.

Figure 9:
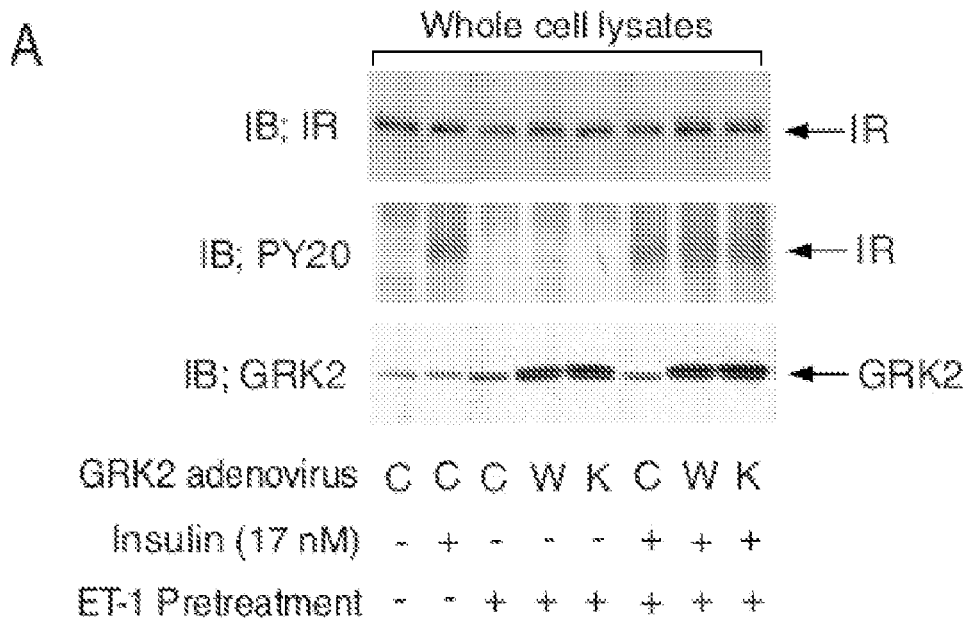
FIG. 9 depicts the effects of wild type- or kinase deficient-GRK2 overexpression on insulin receptor phosphorylation in 3T3-L1 adipocytes.
Figure 9:
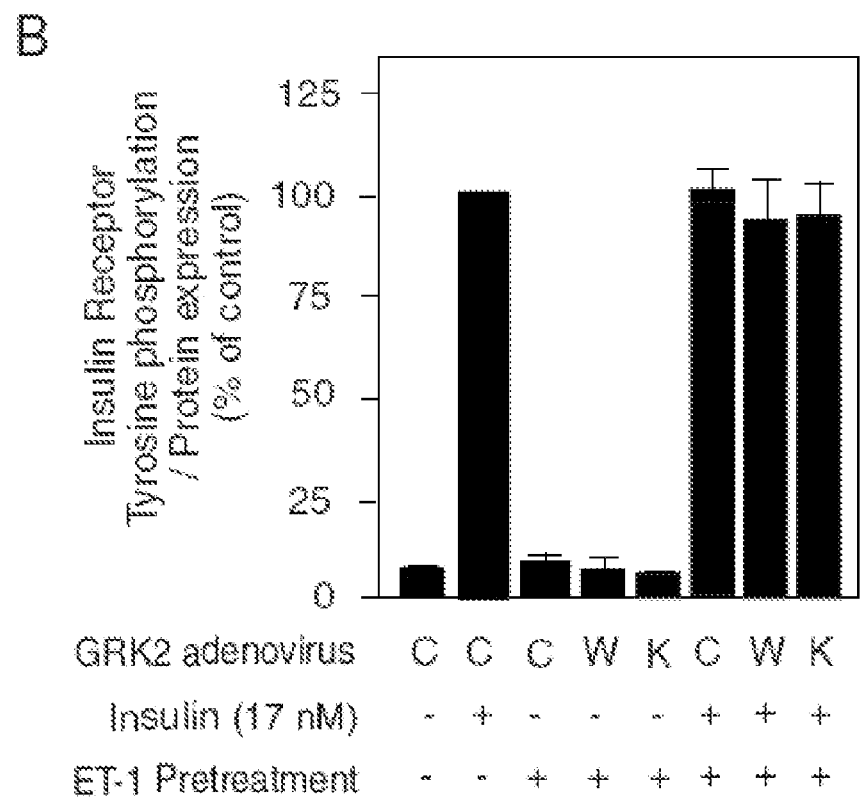

In the basal state, most of the cells displayed staining of GLUT4 in the perinuclear region, while 63% of the cells displayed GLUT4 translocation to the plasma membrane after 1.7 nM insulin stimulation (FIG. 6). When cells were pretreated with 10 nM ET-1 for 24 h, the effect of insulin was inhibited by 65%. Microinjection of GRK2 antibody or GRK2 siRNA into the ET-1 treated cells largely rescued them from the ET-1-mediated decrease in GLUT4 translocation (FIG. 6, 7). Microinjection of GRK5 or GRK6 antibody did not alter insulin-induced GLUT4 translocation, either in the absence or presence of ET-1 treatment (data not shown). Secondly, an expression vector encoding HA-GLUT4-GFP was microinjected. As the HA-tag is located in the first extracellular loop of GLUT4, this construct allowed monitoring of the fusion of GLUT4 in the plasma membrane in non-permeabilized cells by using an HA-directed antibody. At the same time, total expression of the GLUT4 construct is monitored by measuring total GFP fluorescence in individual cells. With this method, the ratio of cell surface HA staining to total GFP fluorescence provides a quantitative measure of GLUT4 translocation on a single cell bases. Both siRNA and HA-GLUT4-GFP expression vector were microinjected together into the cell nucleus of 3T3-L1 adipocytes. GFP fluorescence-positive cells were then analyzed by immunofluorescent microscopy to quantitate the ratio of cell surface HA-staining to total GLUT4-GFP fluorescence, as described herein. As can be seen in FIG. 9, insulin-stimulated GLUT4 translocation was inhibited by chronic ET-1 treatment and this effect was prevented by injection of GRK2 siRNA. Thus, both methods used to quantitate GLUT4 translocation yielded comparable results.

GRK2 does not Affect Insulin Receptor Tyrosine Phosphorylation

To assess the involvement of GRK2 in ET-1-induced insulin resistance, the role of GRK2 in insulin signaling was examined (FIG. 9). In FIG. 9, 3T3-L1 adipocytes were infected with adenovirus encoding LacZ control (C), wild type- (W) or kinase deficient-GRK2 (K). 24 h after infection, these cells were treated with or without 10 nM endothelin-1 (ET-1) for 24 h, serum-starved for 16 h, stimulated with 17 nM insulin for 5 min and lysed. Total cell lysates were analyzed by Western blotting using anti-insulin receptor (IR), anti-phosphotyrosine (PY20) or anti-GRK2 antibody, as described herein in the Examples. Representative blots are shown from three independent experiments. In panel (B), the signal intensities were scanned and quantitated using NIH image software. The ratio of tyrosine phosphorylation signal (middle panel in A)/insulin receptor protein level (top panel in A) was calculated and shown. The data are mean ±S.E. from three independent experiments.

To accomplish examination of the role of GRK2 in insulin signaling, adenoviruses containing wild type (WT) or kinase deficient (KD)-GRK2 were prepared. In FIG. 10, 3T3-L1 adipocytes were infected with adenovirus expressing wild type- (W) or kinase deficient-GRK2 (K) or control LacZ (C). 24 h after infection, these cells were treated with or without 10 nM endothelin-1 (ET-1) for 24 h, serum-starved for 16 h, stimulated with 17 nM insulin for 10 min, and lysed. Samples were immunoprecipitated with anti-cdc42 antibody or control IgG (negative control; NC). PI3-kinase activity was measured as described in "Experimental Procedures". A representative film is shown and the graph represents the mean ±S.E. of three independent experiments. In FIG. 11, 3T3-L1 adipocytes were serum-starved for 16 h, stimulated with 17 nM insulin or 10 nM endothelin-1 for the indicated time periods and lysed. Samples were immunoprecipitated with anti-GRK2 antibody or control IgG (negative control; NC). Immunoprecipitates and total cell lysate (TCL) were analyzed by Western blotting using anti-Gαq/11 antibody as described under "Experimental Procedures". A representative blot is shown from three independent experiments. (C) 3T3-L1 adipocytes were infected with adenovirus expressing wild type- (W) or kinase deficient-GRK2 (K) or control LacZ (C). 24 h after infection, these cells were serum-starved for 16 h, stimulated with 10 nM endothelin-1 (ET-1) or 17 nM insulin for 1 min, and lysed. Samples were immunoprecipitated with anti-phosphotyrosine (PY20) or control IgG (NC), and were analyzed by Western blotting using anti-Gαq/11 antibody, as described under "Experimental Procedures". A representative blot is shown from three independent experiments.

As shown in FIGS. 10 and 11, adenovirus-mediated expression of either WT- or KD-GRK2 had no effect on insulin receptor expression level or tyrosine phosphorylation in the ET-1 treated cells. Additionally, the insulin receptor was not immunoprecipitated using anti-GRK2 antibody (data not shown).

GRK2 Directly Binds to Gαq/11 and Inhibits Insulin-Induced Activation of the Gαq/11 Pathway Before and After ET-1 Treatment.

Chronic ET-1 treatment leads to insulin resistance associated with decreased tyrosine phosphorylation of IRS-1 and Gαq/11. Thus, the role of GRK2 in the Gαq/11 pathway during ET-1 administration was assessed. Insulin treatment leads to increased tyrosine phosphorylation of Gαq/11, cdc42 activation, and association of cdc42 and PI3-kinase. As shown in FIG. 10, insulin-stimulated cdc42-associated PI3-kinase activity was inhibited by 24 h ET-1 treatment. Overexpression of either WT- or KD-GRK2 further suppressed cdc42-associated PI3-kinase activity, indicating that GRK2 can function to inhibit Gαq/11 and cdc42 activities. Since the inhibitory effects of these two adenoviruses are comparable, it is unlikely that GRK2 kinase activity is required for the inhibition of the Gαq/11 pathway after ET-1 treatment. The expression level of Gαq/11, cdc42 or p85 was not altered by ET-1 treatment and/or overexpression of WT- or KD-GRK2 (data not shown).

To further assess the mechanisms of inhibition of Gαq/11 by GRK2, the association of endogenous GRK2 and Gαq/11 before and after insulin or ET-1 stimulation was measured (FIG. 11). Association of endogenous GRK2 and Gαq/11 was not detected in the basal state, but was markedly enhanced by either ET-1 or insulin with a maximal response at 5 min, and decreased to basal levels by 60 min. As seen in FIG. 11 (bottom panel), both WT- and KD-GRK2 overexpression inhibited Gαq/11 tyrosine phosphorylation stimulated by ET-1 or insulin. These results suggest that GRK2 inhibits the activation of Gαq/11 and its downstream actions through a direct association of GRK2 and Gαq/11, independent of GRK2 kinase activity.

Figure 12:
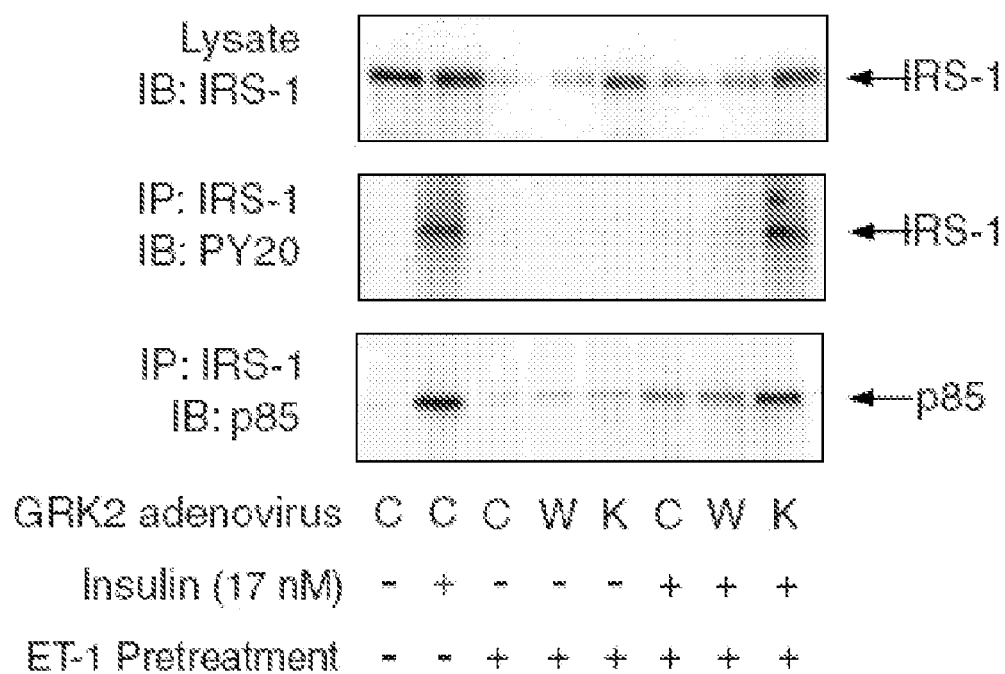
FIG. 12 depicts the effects of wild type- or kinase deficient-GRK2 overexpression on IRS-1-PI3-kinase pathway in 3T3-L1 adipocytes.
Figure 13:
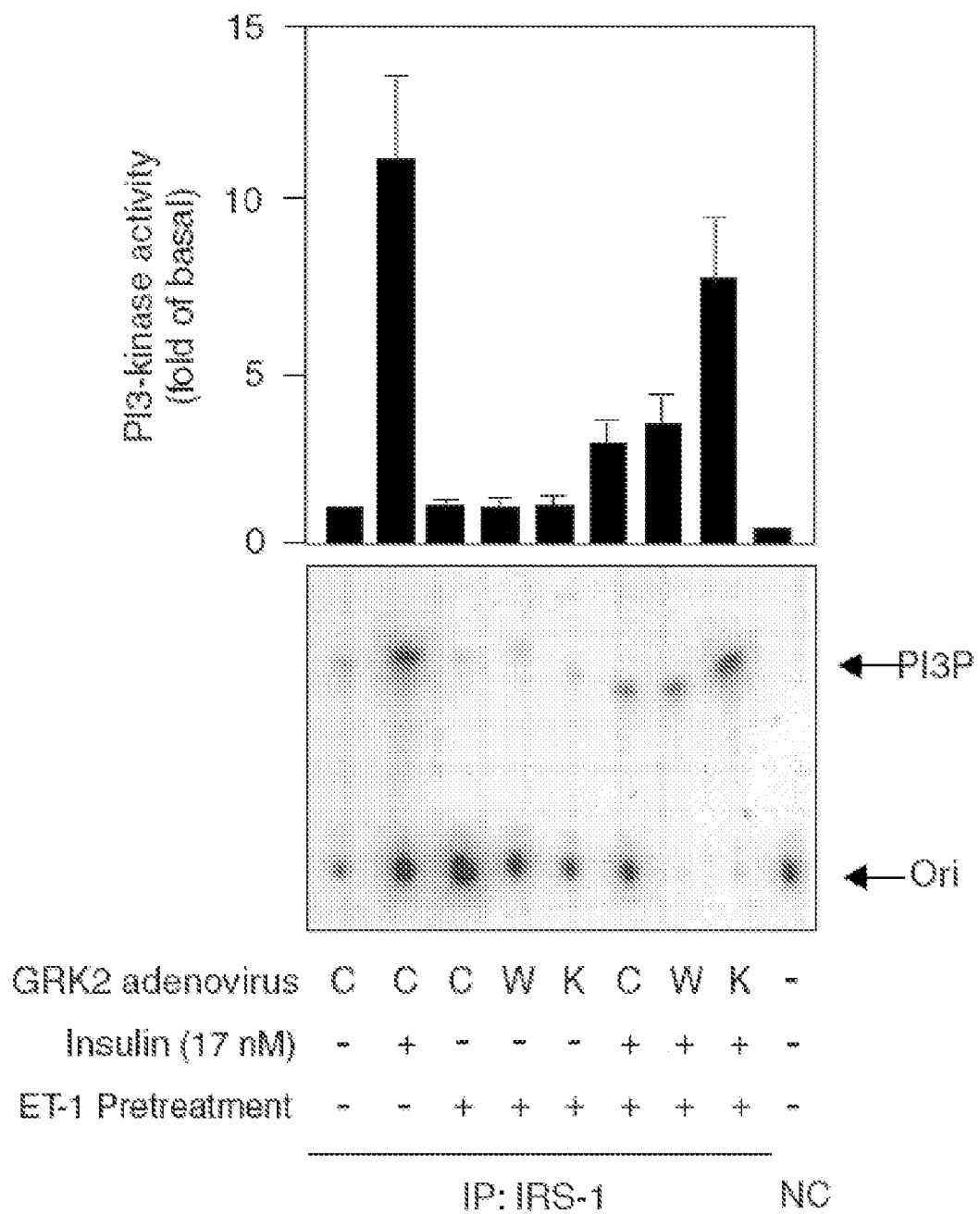
FIG. 13 is another depiction of the effects of wild type- or kinase deficient-GRK2 overexpression on IRS-1-PI3-kinase pathway in 3T3-L1 adipocytes.

GRK2 is Involved in ET-1-Stimulated Serine Phosphorylation of IRS-1 and Degradation of IRS-1 Protein The effect of WT- or KD-GRK2 expression on the IRS-1 pathway in the presence of chronic ET-1 treatment was measured (FIG. 12, 13). In FIG. 12, 3T3-L1 adipocytes were infected with adenovirus expressing wild type- (W) or kinase deficient-GRK2 (K) or control LacZ (C). Twenty-four h after infection, these cells were treated with or without 10 nM endothelin-1 (ET-1) for 24 h, serum-starved for 16 h, stimulated with 17 nM insulin for 5 min (for IRS-1 and PY20 blots) or 10 min (for p85 blot), and lysed. Samples were then immunoprecipitated with anti-IRS-1 antibody. Immunoprecipitates and total cell lysates were analyzed by Western blotting using anti-IRS-1, anti-phosphotyrosine (PY20), or anti-p85 antibody as described herein in the Examples. In FIG. 13, 3T3-L1 adipocytes were infected with adenovirus expressing wild type- (W) or kinase deficient-GRK2 (K) or control LacZ (C). 24 h after infection, these cells were treated with or without 10 nM endothelin-1 (ET-1) for 24 h, serum-starved for 16 h, stimulated with 17 nM insulin for 10 min, and lysed. Samples were immunoprecipitated with or without (negative control; NC) anti-IRS-1 antibody. PI3-kinase activity was measured as described in "Experimental Procedures". The graph represents the mean ±S.E. of three independent experiments.

Figure 14:
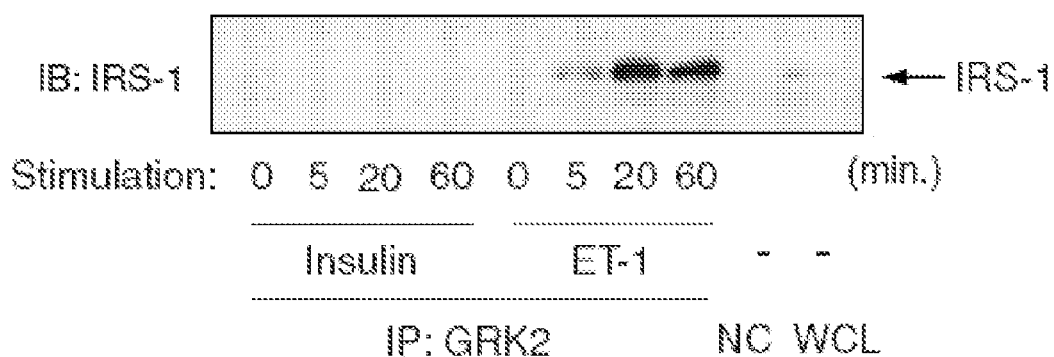
FIG. 14 is another depiction of the effects of wild type- or kinase deficient-GRK2 overexpression on IRS-1-PI3-kinase pathway in 3T3-L1 adipocytes.
Figure 14:
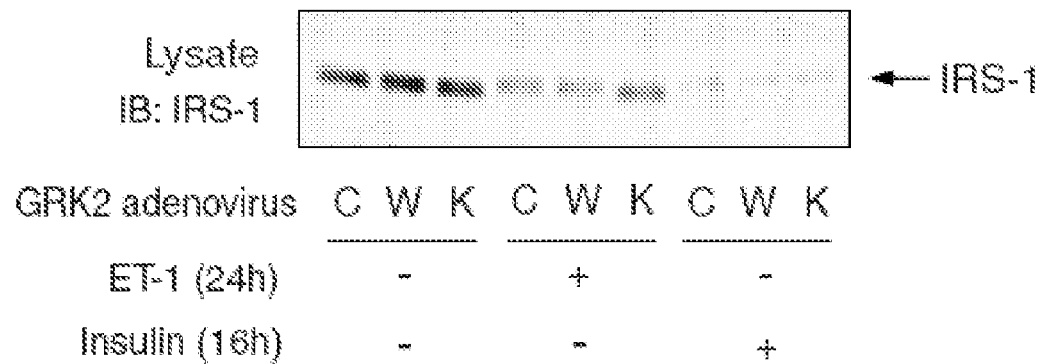

Chronic ET-1 treatment leads to degradation of IRS-1, inhibition of insulin-stimulated IRS-1 tyrosine phosphorylation, and decreased association of IRS-1 and p85. Overexpression of WT-GRK2 had no effect on these alterations in the IRS-1 pathway caused by chronic ET-1 treatment. In contrast, overexpression of KD-GRK2 inhibited ET-1-induced IRS-1 degradation, suggesting that the kinase activity of GRK2 is involved in this process. Similarly, KD-GRK2 rescued the chronic ET-1-induced inhibition of IRS-1 tyrosine phosphorylation (FIG. 12) and PI3-kinase association (FIG. 13). The association of endogenous GRK2 with IRS-1 before and after insulin or ET-1 stimulation was assessed (FIG. 14). In FIG. 14, 3T3-L1 adipocytes were serum-starved for 16 h, stimulated with 17 nM insulin or 10 nM endothelin-1 (ET-1) for the indicated time periods, and lysed. Samples were immunoprecipitated with anti-GRK2 antibody or control IgG (negative control; NC). Immunoprecipitates and total cell lysate (TCL) were analyzed by Western blotting using anti-IRS-1 as described in the Examples herein. (D) 3T3-L1 adipocytes were infected with adenovirus expressing wild type- (W) or kinase deficient-GRK2 (K) or control LacZ (C). Twenty-four h after infection, these cells were treated with 10 nM endothelin-1 (ET-1) for 24 h or 17 nM insulin for 16 h, and lysed. Total cell lysates were analyzed by Western blotting using anti-IRS-1 antibody as described herein in the Examples. In all cases, representative images are shown from three independent experiments.

Binding of endogenous GRK2 and IRS-1 was not detected in the basal state, but was markedly enhanced following ET-1 treatment. Insulin treatment did not induce the association of these proteins. GRK2 involvement in IRS-1 degradation following chronic insulin treatment was then examined (FIG. 14 (bottom panel)). Insulin treatment for 16 h, as well as ET-1 treatment for 24 h, caused IRS-1 degradation. While overexpression of KD-GRK2 inhibited ET-1-induced IRS-1 degradation, it did not inhibit insulin-induced IRS-1 degradation.

Figure 15:
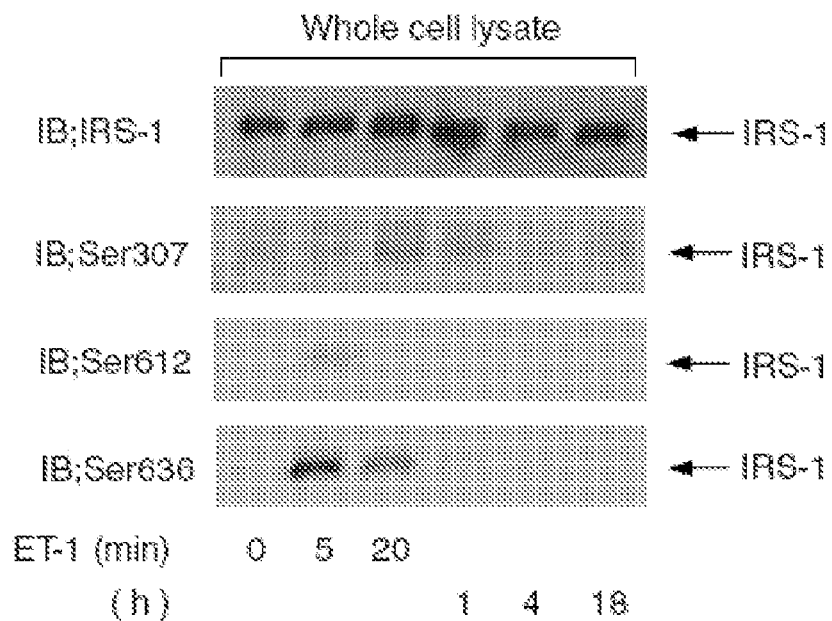
FIG. 15 depicts the effects of wild type- or kinase deficient-GRK2 overexpression on ET-1-induced serine phosphorylation of IRS-1.
Figure 15:
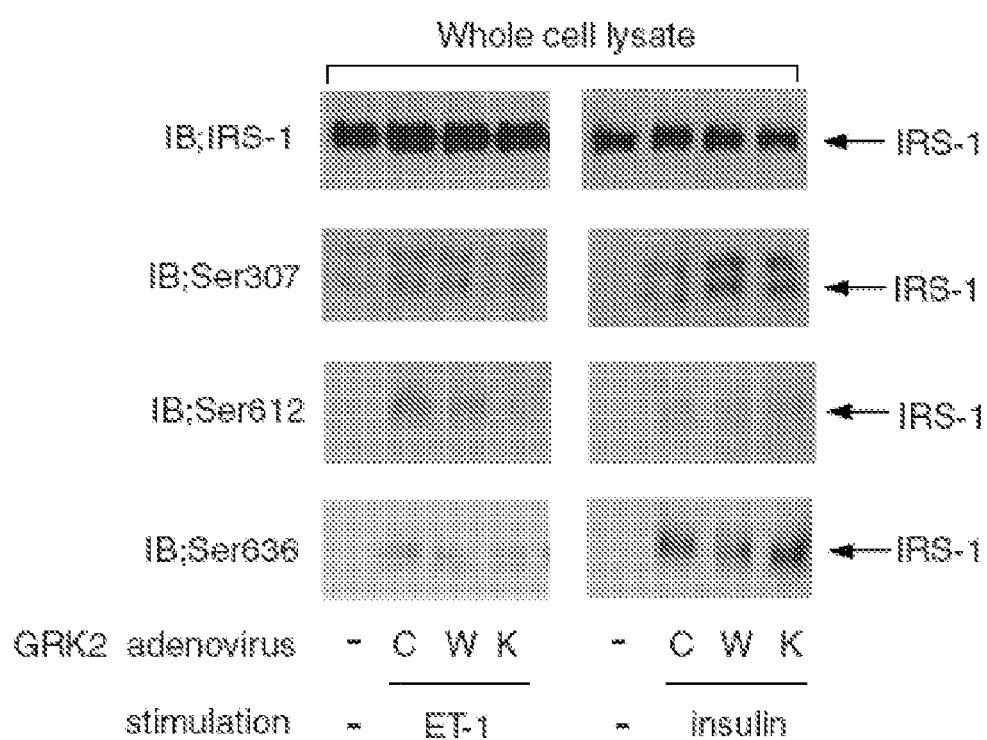
Figure 16:
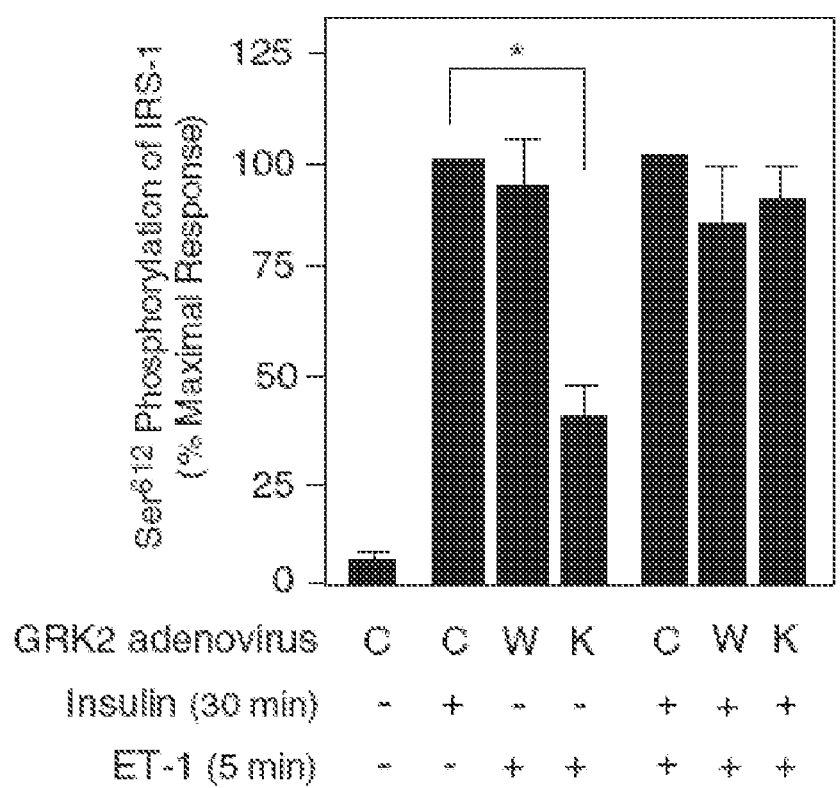
FIG. 16 is another depiction of the effects of wild type- or kinase deficient-GRK2 overexpression on ET-1-induced serine phosphorylation of IRS-1.

Serine phosphoryation can lead to decreased IRS-1 tyrosine phosphorylation, as well as IRS-1 degradation. To further investigate how GRK2 enhances IRS-1 degradation, the serine phosphorylation of IRS-1 after ET-1 treatment using phospho-specific IRS-1 antibodies against Ser 307, Ser 612 and Ser 636 were investigated. ET-1 treatment clearly enhanced the serine phosphorylation of IRS-1 on these three residues. Interestingly, as shown in FIG. 15, the time course of Ser 307 and Ser 612/636 phosphorylation were different, i.e., the former reached a maximal response at 20 min to 1 h, whereas, the latter was maximal 5 min after ET-1 treatment. These results suggest the possibility that different serine kinases are involved in the phosphorylation of Ser 307 versus Ser 612/636 (FIG. 15). In FIG. 15, (top panel) 3T3-L1 adipocytes were serum-starved for 16 h, stimulated with 10 nM endothelin-1 for the indicated time periods and lysed. Total cell lysate were analyzed by Western blotting using anti-phospho-specific IRS-1 antibody against serine 307, 612, and 636, as described under "Experimental Procedures". A representative blot is shown from three independent experiments. In the bottom panel, 3T3-L1 adipocytes were infected with adenovirus expressing wild type- (W) or kinase deficient-GRK2 (K) or control LacZ (C). Twenty-four h after infection, these cells were serum-starved for 16 h, stimulated with 10 nM endothelin-1 (ET-1) or 17 nM insulin for 5 min, and lysed. Whole cell lysates were analyzed by Western blotting using anti-phospho-specific IRS-1 antibody against serine 307, 612, and 636. Representative blots are shown from three independent experiments. In FIG. 16, The signal intensity of IRS-1 Ser612-phosphorylation was scanned and quantitated using NIH image software. The data are the mean ±S.E. from three independent experiments.

The effects of wild type- or kinase deficient-GRK2 on IRS-1 serine phosphorylation were next examined. Serine phosphorylation of IRS-1 at Ser 612/636 after 5 min ET-1 treatment was inhibited by KD-GRK2 expression, but not by WT-GRK2. Serine phosphorylation at Ser 307 after 20 min ET-1 treatment was not inhibited by either KD- or WT-GRK2, suggesting that GRK2 is involved in the phosphorylation of serine 612/636, but not serine 307. In contrast, neither of the GRK2 constructs had any effect on insulin-induced IRS-1 serine phosphorylation.

Other Embodiments

The detailed description set-forth above is provided to aid those skilled in the art in practicing the present invention. However, the invention described and claimed herein is not to be limited in scope by the specific embodiments herein disclosed because these embodiments are intended as illustration of several aspects of the invention. Any equivalent embodiments are intended to be within the scope of this invention. Indeed, various modifications of the invention in addition to those shown and described herein will become apparent to those skilled in the art from the foregoing description which do not depart from the spirit or scope of the present inventive discovery. Such modifications are also intended to fall within the scope of the appended claims.

References Cited

All publications, patents, patent applications and other references cited in this application are incorporated herein by reference in their entirety for all purposes to the same extent as if each individual publication, patent, patent application or other reference was specifically and individually indicated to be incorporated by reference in its entirety for all purposes. Citation of a reference herein shall not be construed as an admission that such is prior art to the present invention. Specifically intended to be within the scope of the present invention, and incorporated herein by reference in its entirety, is the following publication: Usui I, Imamura T, Satoh H, Huang J, Babendure J L, Hupfeld C J, Olefsky J M. GRK2 is an endogenous protein inhibitor of the insulin signaling pathway for glucose transport stimulation. EMBO J. 2004 Jul. 21; 23(14):2821-9.

What is claimed is:

1. A method of identifying a candidate insulin sensitizing compound, the method comprising:
   (a) contacting a GRK2 molecule with Gαq/11 to form an assay mixture, wherein the GRK2 molecule is GRK2 or biologically-active fragment of GRK2 that has an inhibitory action on insulin signaling,
   (b) contacting the assay mixture with a test compound, and
   (c) determining the ability of the GRK2 molecule to preferentially bind to Gαq/11, wherein determining comprises (i) incubating the assay mixture in (b) under conditions conducive to formation of a binding complex of the GRK2 molecule and Gαq/11; (ii) removing unbound components from the assay mixture; and (iii) determining the amount of complex formed,
   wherein an interaction of the test compound with GRK2 to decrease binding of Gαq/11 with GRK2 compared to binding in absence of the test compound indicates that the test compound is an insulin sensitizing compound.

2. A method according to claim 1, wherein the GRK2 molecule is immobilized to a substrate.

3. A method according to claim 1, wherein the Gαq/11 is immobilized to a substrate.

4. A method according to claim 1, wherein determining the amount of complex formed employs immunodetection or enzyme-linked detection.

5. A method of identifying a candidate insulin sensitizing compound, the method comprising:
   (a) immobilizing a GRK2 molecule, wherein the GRK2 molecule is GRK2 or a biologically-active fragment of GRK2 that has an inhibitory action on insulin signaling;
   (b) contacting the immobilized GRK2 molecule with Gαq/11 and a test compound to form an assay mixture;
   (c) incubating the assay mixture under conditions conducive to forming an immobilized binding complex of the GRK2 molecule and Gαq/11;
   (d) removing unbound components from the assay mixture; and
   (e) determining the amount of immobilized complex formed,
   wherein an interaction of the test compound with the immobilized GRK2 to decrease binding of Gαq/11 with the immobilized GRK2 compared to binding in absence of the test compound indicates that the test compound is an insulin sensitizing compound.

6. A method according to claim 5, wherein determining employs immunodetection or enzyme-linked detection.

7. A method of identifying a candidate insulin sensitizing compound, the method comprising:
(a) immobilizing Gαq/11 to a substrate;
(b) contacting the immobilized Gαq/11 with a GRK2 molecule, wherein the GRK2 molecule is GRK2 or a biologically-active fragment of GRK2 that has an inhibitory action on insulin signaling and a test compound to form an assay mixture;
(c) incubating the assay mixture under conditions conducive to forming an immobilized binding complex of the GRK2 molecule and Gαq/11;
(d) removing unbound components from the assay mixture; and
(e) determining the amount of immobilized complex formed,
wherein an interaction of the test compound with the immobilized Gαq/11 to decrease binding of GRK2 with the immobilized Gαq/11 compared to binding in absence of the test compound indicates that the test compound is an insulin sensitizing compound.

8. A method according to claim 7, wherein determining employs immunodetection or enzyme-linked detection.

* * * * *